US011519713B2

(12) United States Patent
Hendon et al.

(10) Patent No.: US 11,519,713 B2
(45) Date of Patent: Dec. 6, 2022

(54) SYSTEM, METHOD, COMPUTER-ACCESSIBLE MEDIUM, AND APPARATUS FACILITATING ULTRA-HIGH RESOLUTION OPTICAL COHERENCE TOMOGRAPHY FOR AUTOMATED DETECTION OF DISEASES

(71) Applicant: The Trustees of Columbia University in the City of New York, New York, NY (US)

(72) Inventors: Christine Hendon, Bronx, NY (US); Richard Ha, White Plains, NY (US); Diana Mojahed, New York, NY (US); Hanina Hibshoosh, New York, NY (US); James McLean, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 17/162,720

(22) Filed: Jan. 29, 2021

(65) Prior Publication Data
US 2021/0239450 A1 Aug. 5, 2021

Related U.S. Application Data

(60) Provisional application No. 62/968,436, filed on Jan. 31, 2020.

(51) Int. Cl.
*G01B 11/02* (2006.01)
*G01B 9/02091* (2022.01)
(Continued)

(52) U.S. Cl.
CPC .......... *G01B 9/02091* (2013.01); *A61B 3/102* (2013.01); *H01L 33/0045* (2013.01)

(58) Field of Classification Search
CPC ................ G01B 9/02091; G01B 9/02044; A61B 3/102; H01L 33/0045
See application file for complete search history.

(56) References Cited

U.S. PATENT DOCUMENTS

| 2013/0169971 A1* | 7/2013 | Brown | G01B 9/02063 356/479 |
| 2015/0230708 A1* | 8/2015 | Wang | A61B 5/0066 600/425 |
| 2018/0242847 A1* | 8/2018 | Boppart | A61B 5/7257 |

OTHER PUBLICATIONS

Liu X, Kang Ju. Sparse OCT: Optimizing compressed sensing in spectral domain optical coherence tomography. Proc SPIE Int Soc Opt Eng. 2011;7904:874058. doi:10.1117/12.874058 (Year: 2011).*

(Continued)

*Primary Examiner* — Tarifur R Chowdhury
*Assistant Examiner* — Jonathon Cook
(74) *Attorney, Agent, or Firm* — Hunton Andrews Kurth LLP

(57) ABSTRACT

An exemplary system for generating an image(s) of a sample(s) can include, for example, an imaging arrangement that can include a superluminescent diode (SLD) configured to generate a radiation(s) to be provided to the sample(s), and a spectrometer configured to (i) sample an A-line sampling rate of at least about 200 kHz, (ii) receive a resultant radiation from the sample(s) based on the sampling rate, and (iii) generate information based on the resultant radiation, and a computer hardware arrangement configured to generate the image(s) of the sample(s) based on the information received from the spectrometer. The imaging arrangement can be an interferometric imaging arrangement, which can be an optical coherence tomography imaging (OCT) arrangement. The computer hardware arrangement can be further configured to facilitate a plurality of b-scan (Continued)

acquisitions of the sample(s) and facilitate the b-scan acquisitions in order to generate the image(s).

17 Claims, 27 Drawing Sheets

(51) Int. Cl.
    *H01L 33/00*     (2010.01)
    *A61B 3/10*     (2006.01)

(56) References Cited

OTHER PUBLICATIONS

V. Srinivasan et al. "Noninvasive Volumetric Imaging and Morphometry of the Rodent Retina with High-Speed, Ultrahigh-Resolution Optical Coherence Tomography," Invest Ophthalmol Vis Sci. Dec. 2006 ; 47(12): 5522-5528.
"Biomedical Engineering Reference," Optical Coherence Tomography: Technical Aspects—Biomedical Optical Imaging Technologies: Design and Applications, p. 176, May 2022.
W. Wieser, W. Draxinger, T. Klein, S. Karpf, T. Pfeiffer, and R. Huber, "High definition live 3d-oct in vivo: design and evaluation of a 4d oct engine with 1 gvoxel/s," Biomed. Opt. Express 5, 2963-2977 (2014).
Y. Ling, X. Yao, U. A. Gamm, E. Arteaga-Solis, C. W. Emala, M. A. Choma, and C. P. Hendon, "Ex vivo visualization of human ciliated epithelium and quantitative analysis of induced flow dynamics by using optical coherence tomography," Lasers Surg. Med. 49, 270-279 (2017).
J. P. McLean, Y. Ling, and C. P. Hendon, "Frequency-constrained robust principal component analysis: a sparse representation approach to segmentation of dynamic features in optical coherence tomography imaging," Opt. Express 25, 25819-25830 (2017).
T. H. Lye, K. P. Vincent, A. D. McCulloch, and C. P. Hendon, "Tissue-Specific Optical Mapping Models of Swine Atria Informed by Optical Coherence Tomography," Biophys. J. 114, 1477-1489 (2018).
J. P. McLean, S. Fang, G. Gallos, K. M. Myers, and C. P. Hendon, "Three-dimensional collagen fiber mapping and tractography of human uterine tissue using OCT," Biomed. Opt. Express 11, 5518 (2020).
J. P. Kolb, W. Draxinger, J. Klee, T. Pfeiffer, M. Eibl, T. Klein, W. Wieser, and R. Huber, "Correction: Live video rate volumetric OCT imaging of the retina with multi-MHz A-scan rates," PLoS One 14, e0220829 (2019).
Y. Chen, Y.-J. Hong, S. Makita, and Y. Yasuno, "Three-dimensional eye motion correction by lissajous scan optical coherence tomography," Biomed. Opt. Express 8, 1783-1802 (2017).
D. L. Donoho and M. Elad, "Optimally sparse representation in general (nonorthogonal) dictionaries via 1 minimization," Proc. Natl. Acad. Sci. 100, 2197-2202 (2003).
H. Jung, K. Sung, K. S. Nayak, E. Y. Kim, and J. C. Ye, "K-t FOCUSS: A general compressed sensing framework for high resolution dynamic MRI," Magn. Reson. Medicine 61, 103-116 (2009).
R. Otazo, E. Candès, and D. K. Sodickson, "Low-rank plus sparse matrix decomposition for accelerated dynamic MRI with separation of background and dynamic components," Magn. Reson. Medicine 73, 1125-1136 (2015).
M. Lustig, D. Donoho, and J. M. Pauly, "Sparse MRI: The application of compressed sensing for rapid MR imaging," Magn. Reson. Medicine 58, 1182-1195 (2007).
X. Liu and J. U. Kang, "Compressive SD-OCT: the application of compressed sensing in spectral domain optical coherence tomography," Opt. Express 18, 22010 (2010).
D. Xu, N. Vaswani, Y. Huang, and J. U. Kang, "Modified compressive sensing optical coherence tomography with noise reduction," Opt. Lett. 37, 4209 (2012).
N. Zhang, T. Huo, C. Wang, T. Chen, J.-g. Zheng, and P. Xue, "Compressed sensing with linear-in-wavenumber sampling in spectral-domain optical coherence tomography," Opt. Lett. 37, 3075 (2012).
D. Xu, Y. Huang, and J. U. Kang, "Compressive sensing with dispersion compensation on non-linear wavenumber sampled spectral domain optical coherence tomography," Biomed. Opt. Express 4, 1519 (2013).
Y. Ling, W. Meiniel, R. Singh-Moon, E. Angelini, J.-C. Olivo-Marin, and C. P. Hendon, "Compressed sensing-enabled phase-sensitive swept-source optical coherence tomography," Opt. Express 27, 855 (2019).
E. Lebed, P. J. Mackenzie, M. V. Sarunic, and F. M. Beg, "Rapid Volumetric OCT Image Acquisition Using Compressive Sampling," Opt. Express 18, 21003 (2010).
D. Xu, Y. Huang, and J. U. Kang, "Real-time compressive sensing spectral domain optical coherence tomography," Opt. Lett. 39, 76 (2014).
D. Xu, Y. Huang, and J. U. Kang, "GPU-accelerated non-uniform fast Fourier transform-based compressive sensing spectral domain optical coherence tomography," Opt. Express 22, 14871 (2014).
D. Xu, Y. Huang, and J. U. Kang, "Volumetric (3D) compressive sensing spectral domain optical coherence tomography," Biomed. Opt. Express 5, 3921 (2014).
S. Schwartz, C. Liu, A. Wong, D. A. Clausi, P. Fieguth, and K. Bizheva, "Energy-guided learning approach to compressive FD-OCT," Opt. Express 21, 329 (2013).
L. Fang, S. Li, R. P. McNabb, Q. Nie, A. N. Kuo, C. A. Toth, J. A. Izatt, and S. Farsiu, "Fast acquisition and reconstruction of optical coherence tomography images via sparse representation," IEEE Transactions on Med. Imaging 32, 2034-2049 (2013).
S. Oshery, Z. Shiz, and W. Zhuy, "Low dimensional manifold model for image processing," SIAM J. on Imaging Sci. 10, 1669-1690 (2017).
E. J. Candès, X. Li, Y. Ma, and J. Wright, "Robust principal component analysis?" J. ACM 58, 1-37 (2011).
I. Daubechies, M. Defrise, and C. De Mol, "An iterative thresholding algorithm for linear inverse problems with a sparsity constraint," Commun. on Pure Appl. Math. 57, 1413-1457 (2004).
S. Boyd, "Distributed Optimization and Statistical Learning via the Alternating Direction Method of Multipliers," Foundations Trends Mach. Learn. 3, 1-122 (2010).
A. Majumdar, R. K. Ward, and T. Aboulnasr, "Compressed sensing based real-time dynamic MRI reconstruction," IEEE Transactions on Med. Imaging 31, 2253-2266 (2012).
Y.-W. Wen, M. K. Ng, and W.-K. Ching, "Iterative Algorithms Based on Decoupling of Deblurring and Denoising for Image Restoration," SIAM J. on Sci. Comput. 30, 2655-2674 (2008).
E. M. Eksioglu, "Decoupled Algorithm for MRI Reconstruction Using Nonlocal Block Matching Model: BM3D-MRI," J. Math. Imaging Vis. 56, 430-440 (2016).
J. Yang and Y. Zhang, "Alternating Direction Algorithms for l1-Problems in Compressive Sensing," SIAM J. on Sci. Comput. 33, 250-278 (2011).
J. Yang, Y. Zhang, and W. Yin, "A fast alternating direction method for TVL1-L2 signal reconstruction from partial Fourier data," IEEE J. on Sel. Top. Signal Process. 4, 288-297 (2010).
Y. Gan, D. Tsay, S. B. Amir, C. C. Marboe, and C. P. Hendon, "Automated classification of optical coherence tomography images of human atrial tissue," J. Biomed. Opt. 21, 101407 (2016).
S. Farsiu, S. J. Chiu, R. V. O'Connell, F. A. Folgar, E. Yuan, J. A. Izatt, and C. A. Toth, "Quantitative classification of eyes with and without intermediate age-related macular degeneration using optical coherence tomography," Ophthalmology 121, 162-172 (2014).
J. P. McLean, Y. Gan, T. H. Lye, D. Qu, H. H. Lu, and C. P. Hendon, "High-speed collagen fiber modeling and orientation quantification for optical coherence tomography imaging," Opt. Express 27, 14457-14471 (2019).
D. Qu, P. J. Chuang, S. Prateepchinda, P. S. Balasubramanian, X. Yao, S. B. Doty, C. P. Hendon, and H. H. Lu, "Micro- and Ultrastructural Characterization of Age-Related Changes at the Anterior Cruciate Ligament-to-Bone Insertion," ACS Biomater. Sci. & Eng. 3, 2806-2814 (2017).

(56) References Cited

OTHER PUBLICATIONS

D. Mojahed, R. S. Ha, P. Chang, Y. Gan, X. Yao, B. Angelini, H. Hibshoosh, B. Taback, and C. P. Hendon, "Fully Automated Postlumpectomy Breast Margin Assessment Utilizing Convolutional Neural Network Based Optical Coherence Tomography Image Classification Method," Acad. Radiol. 27, e81-e86 (2020).

Z. Wang, A. C. Bovik, H. R. Sheikh, and E. P. Simoncelli, "Image quality assessment: From error visibility to structural similarity," IEEE Transactions on Image Process. 13, 600-612 (2004).

Z. Wang, E. Simoncelli, and A. Bovik, "Multiscale structural similarity for image quality assessment," in the Thrity-Seventh Asilomar Conference on Signals, Systems & Computers, 2003, vol. 2 (IEEE, 2016), pp. 1398-1402.

W. Liao, J. Hsieh, C. Wang, W. Zhang, S. Ai, Z. Peng, Z. Chen, B. He, X. Zhang, N. Zhang, B. Tang, and P. Xue, "Compressed sensing spectral domain optical coherence tomography with a hardware sparse-sampled camera," Opt. Lett. 44, 2955 (2019).

J. Wang, Y. Hu, and J. Wu, "Three-dimensional endoscopic OCT using sparse sampling with a miniature magnetic-driven scanning probe," Appl. Opt. 57, 10056 (2018).

Y. Gan, T. H. Lye, C. C. Marboe, and C. P. Hendon, "Characterization of the human myocardium by optical coherence tomography," J. Biophotonics pp. 1-10 (2019).

C. P. Hendon, T. H. Lye, X. Yao, Y. Gan, and C. C. Marboe, "Optical coherence tomography imaging of cardiac substrates," Quant. Imaging Medicine Surgery; Publ. Ahead Print 9, 882-904 (2019).

J. Mavadia-Shukla, P. Fathi, W. Liang, S. Wu, C. Sears, and X. Li, "High-speed, ultrahigh-resolution distal scanning oct endoscopy at 800 nm for in vivo imaging of colon tumorigenesis on murine models," Biomed. Opt. Express 9, 3731-3739 (2018).

W. Yuan, D. Chen, R. Sarabia-Estrada, H. Guerrero-Cazares, D. Li, A. Quiñones-Hinojosa, and X. Li, "Theranostic OCT microneedle for fast ultrahigh-resolution deep-brain imaging and efficient laser ablation in vivo," Sci. Adv. 6, 1-10 (2020).

L. M. Peterson, M. W. Jenkins, S. Gu, L. Barwick, M. Watanabe, and A. M. Rollins, "4D shear stress maps of the developing heart using Doppler optical coherence tomography," Biomed. Opt. Express 3, 3022 (2012).

K. K. Chu, D. Mojahed, C. M. Fernandez, Y. Li, L. Liu, E. J. Wilsterman, B. Diephuis, S. E. Birket, H. Bowers, G. Martin Solomon, B. S. Schuster, J. Hanes, S. M. Rowe, and G. J. Tearney, "Particle-Tracking Microrheology Using Micro-Optical Coherence Tomography," Biophys. J. 111, 1053-1063 (2016).

T. Tang, E. Deniz, M. K. Khokha, and H. D. Tagare, "Gaussian process post-processing for particle tracking velocimetry," Biomed. Opt. Express 10, 3196 (2019).

E. V. Gubarkova, A. A. Sovetsky, V. Y. Zaitsev, A. L. Matveyev, D. A. Vorontsov, M. A. Sirotkina, L. A. Matveev, A. A. Plekhanov, N. P. Pavlova, S. S. Kuznetsov, A. Y. Vorontsov, E. V. Zagaynova, and N. D. Gladkova, "Oct-elastography-based optical biopsy for breast cancer delineation and express assessment of morphological/molecular subtypes," Biomed. Opt. Express 10, 2244-2263 (2019).

B. F. Kennedy, X. Liang, S. G. Adie, D. K. Gerstmann, B. C. Quirk, S. A. Boppart, and D. D. Sampson, "In vivo three-dimensional optical coherence elastography," Opt. Express 19, 6623 (2011).

K. V. Larin and D. D. Sampson, "Optical coherence elastography—oct at work in tissue biomechanics [invited]," Biomed. Opt. Express 8, 1172-1202 (2017).

Y. He, Y. Qu, J. C. Jing, and Z. Chen, "Characterization of oviduct ciliary beat frequency using real time phase resolved doppler spectrally encoded interferometric microscopy," Biomed. Opt. Express 10, 5650-5659 (2019).

H. M. Leung, M. L. Wang, H. Osman, E. Abouei, C. MacAulay, M. Follen, J. A. Gardecki, and G. J. Tearney, "Imaging Intracellular Motion with Dynamic Micro-Optical Coherence Tomography," Biomed. Opt. Express 11, 2768-2778 (2020).

S. Bhat, I. V. Larina, K. V. Larin, M. E. Dickinson, and M. Liebling, "4D reconstruction of the beating embryonic heart from two orthogonal sets of parallel optical coherence tomography slice-sequences," IEEE Transactions on Med. Imaging 32, 578-588 (2013).

X. Zhao, X. Fu, C. Blumenthal, Y. T. Wang, M. W. Jenkins, C. Snyder, M. Arruda, and A. M. Rollins, "Integrated rfa/psoct catheter for real-time guidance of cardiac radio-frequency ablation," Biomed. Opt. Express 9, 6400-6411 (2018).

X. Yu, R. P. Singh-Moon, and C. P. Hendon, "Real-time assessment of catheter contact and orientation using an integrated optical coherence tomography cardiac ablation catheter," Appl. Opt. 58, 3823-3829 (2019).

C. P. Fleming, H. Wang, K. J. Quan, and A. M. Rollins, "Real-time monitoring of cardiac radio-frequency ablation lesion formation using an optical coherence tomography forward-imaging catheter," J. Biomed. Opt. 15, 1-3 (2010).

* cited by examiner

| Specimen | Imaging Time (Single Side) | Imaging Time (Double Side) |
|---|---|---|
| Cassette (L = 2cm) Tissue Block | 41 seconds | 1.4 min |
| Lumpectomy (L = 5cm) Central Sagittal Slice | 1.2 min | 2.4 min |
| Mastectomy (L = 10cm) Central Sagittal Slice | 4.8 min | 9.6 min |
| Large Mastectomy (L = 20cm) Central Sagittal Slice | 12 min | 24 min |

Figure 6

| % of A-Lines | Sample Type | Full Resolution Interval | # Full Res B-Scans | # Sampled A-lines /Patch | N Undersamples (B-Scan) | Compression Rate | Relative Error |
|---|---|---|---|---|---|---|---|
| 25 | Uniform | 10 | 80 | 8 | 102400 | 0.325 | 0.2742 |
|  | Stagger | 50 | 16 | 8 | 102400 | 0.265 | 0.281 |
|  | Uniform | 10 | 80 | 8 | 102400 | 0.325 | 0.2961 |
|  |  | 50 | 16 | 8 | 102400 | 0.265 | 0.3172 |
|  | Random | 10 | 80 | 8 | 102400 | 0.325 | 0.2747 |
|  |  | 50 | 16 | 8 | 102400 | 0.265 | 0.3452 |
| 50 | Uniform | 10 | 80 | 16 | 204800 | 0.55 | 0.213 |
|  | Stagger | 50 | 16 | 16 | 204800 | 0.51 | 0.2146 |
|  | Uniform | 10 | 80 | 16 | 204800 | 0.55 | 0.2395 |
|  |  | 50 | 16 | 16 | 204800 | 0.51 | 0.2541 |
|  | Random | 10 | 80 | 16 | 204800 | 0.55 | 0.2042 |
|  |  | 50 | 16 | 16 | 204800 | 0.51 | 0.2053 |

Figure 22

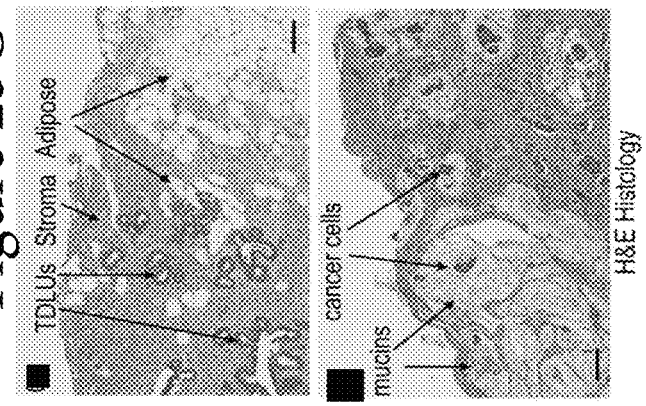
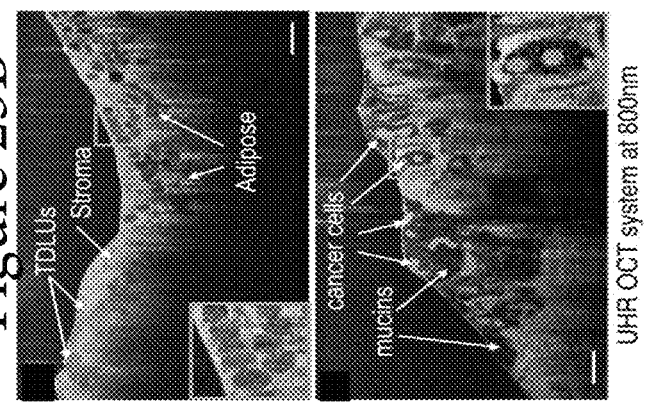
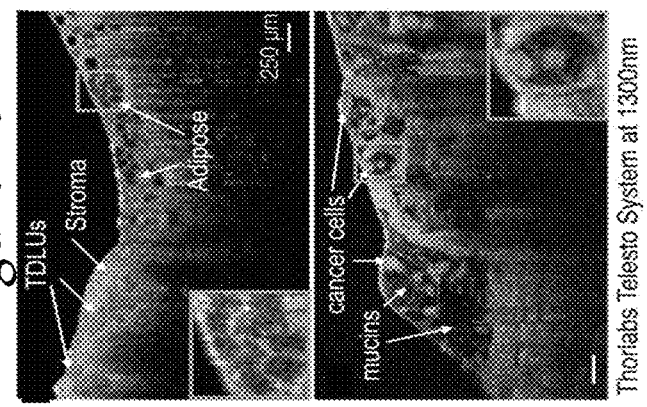
Figure 23A  Figure 23B  Figure 23C
Figure 23D  Figure 23E  Figure 23F

SYSTEM, METHOD, COMPUTER-ACCESSIBLE MEDIUM, AND APPARATUS FACILITATING ULTRA-HIGH RESOLUTION OPTICAL COHERENCE TOMOGRAPHY FOR AUTOMATED DETECTION OF DISEASES

CROSS-REFERENCE TO RELATED APPLICATION(S)

This application relates to and claims priority from U.S. Patent Application No. 62/968,436, filed on Jan. 31, 2020, the entire disclosure of which is incorporated herein by reference.

STATEMENT REGARDING FEDERALLY SPONSORED RESEARCH

This invention was made with government support under Grant Nos. 4DP2HL127776-02, and 1DP2HL127776-01 awarded by the National Institutes of Health. The government has certain rights in the invention.

FIELD OF THE DISCLOSURE

The present disclosure relates generally to optical coherence tomography ("OCT"), and more specifically, to exemplary embodiments of exemplary systems, methods, computer-accessible medium, and apparatuses facilitating an ultra-high resolution optical coherence tomography for an automated detection of one or more diseases.

BACKGROUND INFORMATION

Breast cancer is the most common cancer in women in the United States, and it is anticipated to rise with the aging of the population. Women who are diagnosed with early-stage breast cancer typically undergo breast-conserving surgery, lumpectomy, involving local removal of the breast tumor and the surrounding tumor-free margin. In particular, the excised specimen has to be oriented and inked to determine the margin status should they be positive, serially sliced, grossly examined, sampled and histopathologically reviewed by a pathologist to detect and characterize the underlying pathology. This process can be laborious, and given the frequent discordance between gross features and microscopic findings, it can require a submission of a substantial portion of the lumpectomy, often its entirety. Thus, pathology laboratories and breast pathologists face a large workload and an expensive process. Thus, there is an urgent clinical need for a technology that can aid in more accurately selecting tissues for further analysis, which can reduce cost and workload and increase pathologists' efficiency.

An important feature of OCT is that it can facilitate a capture of three-dimensional images at micron resolution over a larger field of view than what is possible using traditional microscopy. As a result, a typical OCT image volume can contain over 100 million pixels of information. The data requirements of OCT imaging experiments requiring time-lapse imaging (e.g., both 2-D and 3-D in time) (see, e.g., References 1-3), mosaic imaging (see, e.g., References 4-5), or real-time acquisition (see, e.g., Reference 6) can meet or exceed the data through-put capabilities of image acquisition hardware. In some cases, this may prohibit the experiment or require specialized solutions for handling and storing terabytes of data. Long acquisition times can also affect image quality through motion artifacts, particularly for in-vivo imaging. (See, e.g., Reference 7).

Compressed Sensing ("CS") is a procedure in sparse representations that can reconstruct highly undersampled images at full resolution with high accuracy under some assumptions, most notably that the reconstructed signal is sparse in some basis. (See, e.g., Reference 8). For a known undersampling pattern, the problem can be modeled as a linear relationship y=Ax where y is the observed and undersampled signal, x is the sparse, fully sampled signal, and the sensing matrix A provides a mapping between x and y. Though this problem is under-determined, the signal x can be recovered using convex optimization.

CS has revolutionized imaging fields like Mill by decreasing image acquisition time and data storage needs by up to 90%. (See, e.g., References 9-11). CS has also been applied to OCT imaging. Generally, CS-OCT methods aim to either reconstruct the raw interferogram and other hardware-specific signals or the processed OCT signal as an image. The first set of methods have shown great success (see, e.g., References 12-16), although they could not be adapted to existing OCT systems because they operate at the hardware level. CS reconstruction of OCT volumes by modifying the scanning pattern to omit full b-scans and a-lines in a random pattern has been examined. (See, e.g., Reference 17). Other studies have investigated 3-D CS-OCT by undersampling and reconstructing both the raw interferogram and the image volume in a multi-procedure reconstruction process. (See, e.g., Reference 18). They demonstrated that their method can be accelerated using massive GPU parallelization and used in real-time. (See, e.g., References 19 and 20). Other methods have used learning-based approaches to achieve high-accuracy CS reconstruction when the sample type is known. (See, e.g., References 21 and 22). While highly successful, the sample types demonstrated were limited and the approaches were designed specifically for image reconstruction rather than 3-D volumes. Without an appropriate training set, these methods cannot be readily applied to new samples, which makes wide-spread adoption challenging.

Other studies have demonstrated successful 3-D OCT reconstruction. However, the approaches of these studies do not take advantage of structure in the OCT volume, which can be a powerful tool for improving reconstruction accuracy. (See, e.g., References 23 and 24). Furthermore, existing studies of CS-OCT demonstrate successful reconstruction of undersampled images but lack demonstration using more than a few samples with complex tissue structure.

Thus, it may be beneficial to provide exemplary systems, methods, computer-accessible medium and apparatuses providing an ultra-high resolution optical coherence tomography for automated detection of diseases, which can overcome at least some of the deficiencies described herein above.

SUMMARY OF EXEMPLARY EMBODIMENTS

An exemplary system for generating an image(s) of a sample(s) can include, for example, an imaging arrangement that can include a superluminescent diode (SLD) configured to generate a radiation(s) to be provided to the sample(s), and a spectrometer configured to (i) sample an A-line sampling rate of at least about 200 kHz, (ii) receive a resultant radiation from the sample(s) based on the sampling rate, and (iii) generate information based on the resultant radiation, and a computer hardware arrangement configured to generate the image(s) of the sample(s) based on the information received from the spectrometer. The imaging arrangement can be an interferometric imaging arrangement, which can be an optical coherence tomography imaging (OCT) arrangement. The computer hardware arrangement can be further configured to facilitate a plurality of b-scan acquisitions of the sample(s) and facilitate the b-scan acquisitions in order to generate the image(s).

In some exemplary embodiments of the present disclosure, the computer hardware arrangement can be configured to sample the b-scan acquisitions using an A-line staggering procedure and a full-resolution b-scan(s). The computer hardware arrangement can be further configured to extract a plurality of first features from a b-scan of the sample(s), extract a plurality of second features from an en face scan of the sample(s), and generate the image(s) by ensembling the first features and the second features. The spectrometer can have an a-line sampling rate of at least about 250 kHZ. The SLD can be a multiplexed SLD. The SLD can have (i) a central wavelength of about 850 nm, and (ii) a bandwidth of about 100 nm 3 db. The spectrometer can have (i) a bandwidth of about 180 nm, and (ii) a spectral resolution of less than about 0.09 nm.

In certain exemplary embodiments of the present disclosure, the imaging arrangement can comprise (i) an axial resolution of about 5.5 and/or (ii) a lateral resolution of about 5.5 μm. The imaging arrangement can provide a field of view of at least about 10 cm by 10 cm. The computer hardware arrangement can be further configured to analyze the image(s) using a deep learning procedure. The computer arrangement can be further configured to train the deep learning procedure using (i) a plurality of b-scans of a plurality of further samples, or (ii) a plurality of en face images of the plurality of further samples. A motorized scanning stage can be included, which can be configured to move in at least two dimensions, where the motorized scanning stage can be configured to receive the sample thereon(s). The computer hardware arrangement can be configured to generate the image(s) using a compressed sensing procedure.

Additionally, an exemplary method for generating an image(s) of a sample(s) can comprise, for example, generating a radiation(s) using a superluminescent diode (SLD), and providing the radiation to the sample. Using a spectrometer, sampling a resultant radiation received from the tissue(s), that can be based on the radiation(s), at a rate of at least about 200 kHZ. Information that is based on the sampled resultant radiation can be provided, and the image(s) can be generated based on the information. The sampling of the resultant radiation can include sampling the resultant radiation at a rate of at least about 250 kHZ. The SLD can be a multiplexed SLD. The generating of the image(s) can include generating the image(s) using a compressed sensing procedure.

These and other objects, features and advantages of the exemplary embodiments of the present disclosure will become apparent upon reading the following detailed description of the exemplary embodiments of the present disclosure, when taken in conjunction with the appended claims.

BRIEF DESCRIPTION OF THE DRAWINGS

Further objects, features and advantages of the present disclosure will become apparent from the following detailed description taken in conjunction with the accompanying Figure(s) showing illustrative embodiments of the present disclosure, in which:

FIG. 6 is an exemplary table illustrating imaging time for the exemplary optical coherence tomography system according to an exemplary embodiment of the present disclosure;

FIG. 22 is an exemplary table illustrating quantitative summary of the effects of a-line sampling, staggering, and the full-resolution interval on compression and relative error according to an exemplary embodiment of the present disclosure;

FIGS. 23A and 23D are exemplary images generated using a conventional OCT system;

FIGS. 23B and 23E are exemplary images generated using the exemplary ultra-high speed OCT system according to an exemplary embodiment of the present disclosure;

FIG. 23C is an exemplary histopathological correlation for FIGS. 23A and 23D;

FIG. 23F is an exemplary histopathological correlation for FIGS. 23B and 23E according to an exemplary embodiment of the present disclosure;

Figure 1:
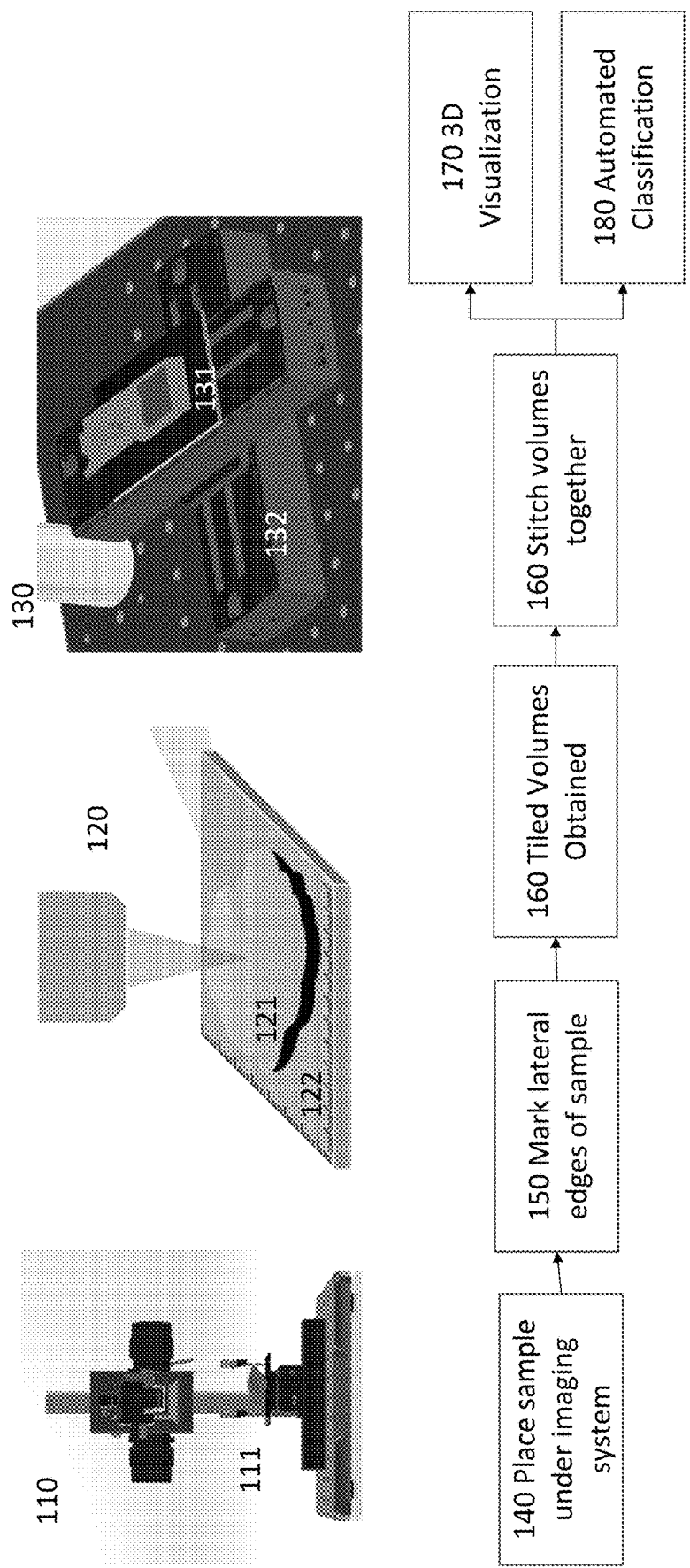
FIG. 1 is a set of exemplary system and flow diagrams provided for implementing a large field-of-view optical coherence tomography system according to an exemplary embodiment of the present disclosure.

Throughout the drawings, the same reference numerals and characters, unless otherwise stated, are used to denote like features, elements, components or portions of the illustrated embodiments. Moreover, while the present disclosure will now be described in detail with reference to the figures, it is done so in connection with the illustrative embodiments and is not limited by the particular embodiments illustrated in the figures and the appended claims.

DETAILED DESCRIPTION OF EXEMPLARY EMBODIMENTS

Indications of breast disease include a myriad of breast lesions that, to date, have only been partially characterized by OCT. While larger OCT datasets than any previous work can be generate, the diversity of breast lesions means that there may not be sufficient data to adequately characterize every disease entity which can be of diagnostic interest. As discussed herein, it can be also important for pathologists to be able to identify regions of breast tissue samples which do not contain any diagnostic indicators, because triaging such regions of non-interest in a step-wise manner can increase the efficiency of the pathology workflow. Early phase of a correlation between findings from OCT and histopathology, and detection of such regions of non-interest (e.g., adipose tissue, normal breast ducts and lobules and fibrous tissue), utilizes fewer lesion recognition criteria and can be more accurate than detection of regions which contain heterogeneous diagnostic indicators.

The exemplary system, method, and computer-accessible medium can facilitate automatic removal of non-suspicious tissue from further analysis via histological processing and immunohistochemistry, substantially improving on prior methods for sample selection in pathological histologic processing of breast resections such as gross analysis, prior clip location and conventional radiology. Real time, high-resolution OCT imaging of fresh or fixed tissue adapted to the setting of a pathology suite can be beneficial, especially for, but not limited to, breast diseases. The comprehensive scanning with OCT of breast plates from serially sectioned lumpectomies or mastectomies can facilitate for more accurate determination of regions which do not warrant further histological processing, substantially increasing accuracy and reducing block submission. This can result in reduced gross room work, histology laboratory processing cost/effort, and pathologist review time while maintaining if not increasing accuracy.

While the exemplary data show that the exemplary system can acquire OCT-generated images with the high speed needed for integration into pathology workflows, the time needed to analyze these images can pose a bottleneck. An exemplary automated procedure analysis according to an exemplary embodiment of the present disclosure can increase the speed of interpretation while also increasing its reliability. A recent multi-reader clinical review that was performed showed that, while human experts can successfully use OCT-generated images to distinguish normal breast parenchyma from pathologic conditions, such manual image interpretation showed inter-observer variability and variation in performance depending on the medical specialty. Manual interpretation can be slow to perform, and substantial time may needed to train readers. Thus, the exemplary system, method, and computer-accessible medium according to exemplary embodiment(s) of the present disclosure can incorporate an automated image analysis to improve diagnostic accuracy with lower inter-observer variability and faster speeds, which can increase the clinical impact of OCT and make it more suitable for clinical use.

The exemplary system, method, and computer-accessible medium, utilizing automated analysis of OCT-generated images, can enhance detection of breast cancer. Polarization-sensitive ("PS") OCT ("PS-OCT"), a variant of OCT, can differentiate healthy fibro-adipose tissue, healthy stroma, and invasive ductal carcinoma ("DC") with an accuracy of 89.4% using the coefficient of variation, and PS retardation and degree of polarization uniformity ("DOPU"). Swept-source optical coherence tomography has been used to perform volumetric analysis of breast cancer using machine learning, with a support-vector-machine-based classifier trained on 10 different features derived from A-lines, texture, and the phase map from OCT intensity and phase images.

Ultra high-resolution ("UHR") OCT-generated images can qualitatively facilitate a better visualization of detailed features in different regions of breast tissue as compared to standard OCT. Using regional features derived from OCT-generated images, an automated classification procedure can be generated based on a relevance vector machine to differentiate hollow-structured adipose tissue against solid tissue, and differentiate solid tissue as stroma or IDC. Tissue classification using UHR OCT-generated images can facilitate superior performance on differentiation of adipose and IDC in breast tissue compared with the images produced by the non-UHR 1300 nm system, with 6.5 µm axial resolution. Using UHR OCT-generated images, increased accuracy can be shown compared to images derived from a system with 6.5 um axial resolution, with a sensitivity of 94% and specificity of 93% for adipose delineation and a sensitivity of 89% and specificity of 71% for identifying IDC against normal fibrous stroma.

The exemplary system, method, and computer-accessible medium according to exemplary embodiment(s) of the present disclosure can be used in, e.g., (i) breast disease detection including breast needle core biopsy guidance and on site pathological assessment at radiology imprint cytology, (i) breast needle core biopsy assessment in pathology to suggest possible diagnoses prior to histologic review, (ii) intra-operative margin assessment in breast conserving surgery (e.g., lumpectomies) to reduce the rate of re-excisions based on positive margins, (iv) intra-operative sentinel lymph node assessment, and/or (v) enhancement of a tissue banking yield by increasing the probability of region of interest identification, as well as to other organs and diseases.

The exemplary approach to image breast specimens within the pathology suite during grossing can expand beyond prior analysis of the margins of whole lumpectomy samples. Improved guidance of sampling where gross/microscopic correlation can be poor can be provided, which can lead to extensive "random sampling" and high workload and inefficiencies in diagnostic pathology. The exemplary system, method, and computer-accessible medium can provide, e.g., (i) a clinical application of region of interest selection in the grossing process along with initially defining regions of non-interest as a way to reduce block submission and increase efficiencies, (ii) a deployment of a high resolution, high speed, and large field of view OCT imaging system specifically designed to meet clinical needs in pathology, (iii) for a study of a large variety of breast lesions to identify the UHR-OCT representation of the full spectrum of disease indicators encountered clinically, and (iv) for a development of automated image analysis using artificial intelligence ("AI"). The exemplary system, method and computer-accessible medium according to exemplary embodiment(s) of the present disclosure can facilitate high speed and high resolution imaging by OCT, in combination with automated image analysis, and can aid the diagnostic pathology process by the more efficient elimination of sample regions unlikely to contribute to disease diagnosis.

Exemplary Clinical Application within Pathology Instead of Margin Assessment

OCT evaluation in the breast realm so far has been confined to real time intra-operative margin assessment designed to reduce margin re-excisions in breast conserving surgery setting (e.g., lumpectomies) and intra-operative sentinel lymph node assessment. Due to limitations in resolution, speed and the size of field of view of OCT systems and methods, the technology has not been routinely clinically adopted in this setting. The exemplary UHR-OCT system and method according to exemplary embodiment(s) of the present disclosure overcomes these limitations. Unlike regions of diagnostic interest, lesion recognition criteria for regions of non-interest have been reliably defined due to their more limited complexity. Immediate clinical benefits can be provided by the exemplary system, method, and computer-accessible medium by making the diagnostic process more efficient while also laying the groundwork for a fully automated diagnostic system, because the deployment of the exemplary technology to aid with sample selection can then incidentally generate large image datasets utilized to fully characterize diagnostic indicators by OCT.

Exemplary High Resolution, High Speed, Large FOV, OCT Imaging System

The wide field of view and high speed of the exemplary UHR-OCT system and method according to exemplary embodiment(s) of the present disclosure can overcome the problems that prevent integration of currently available commercial systems into the pathology workflow. The exemplary UHR OCT systems and methods according to exemplary embodiment(s) of the present disclosure can be beneficial for pathological evaluation of breast tissue because it can provide both higher resolution and better contrast to profile inner tissue structures at a cellular level. The exemplary OCT systems and methods being commercialized for breast imaging (e.g., mainly for the application of margins) can use a light source centered at 1300 nm. For example, 800 nm spectral window, which can provide higher axial resolution and increased contrast, and can be used to obtain images of breast specimens that can be easier to interpret by computer procedures and human readers.

Exemplary Automated Analysis

Exemplary deep learning procedures can be used to automate image analysis to: (i) identify areas of non-interest that do not need to be processed and (ii) areas of interest. Unlike prior OCT image analysis methods, exemplary procedures can be used with a high negative predicative value, therefore identifying non-interest areas with high accuracy. By identifying non-interest areas, the workload within the pathology suite can be reduced by identifying which areas of the lumpectomy should not be sent for further histopathological processing.

Exemplary Methodology

A sample size of 100 cases and appropriately 3,000 breast tissue blocks can be used, as each lumpectomy can be expected to contribute 20-30 blocks. The Cohen's kappa statistic can be used to quantify the agreement between OCT and histology in identifying positive results. A Kappa value of 0.4 can indicate moderate agreement and a value of 0.9 indicates almost perfect agreement. When the frequencies of positive and non-positive results are 0.3 and 0.7, the expected value of the lower bounds of the 95% confidence interval with different sample sizes and anticipated kappa values are presented in Table 1. The kappa statistic can also be used to quantify the agreement between OCT and histology in identifying negative results. When the frequencies of negative and non-negative results are 0.5 and 0.5, the expected value of the lower bounds of the 95% confidence interval with different sample sizes and anticipated kappa values are presented in Table 2 below.

The Cohen's kappa statistic can be used to quantify the agreement between OCT and histology in identifying positive results. A Kappa value of 0.4 can indicate moderate agreement and a value of 0.9 indicates almost perfect agreement. As the true value of kappa can be unknown, the calculation for a range of kappa values are shown. It can be assumed that assume there are 24 blocks per patients on average and the blocks can be independent with each patient. When the frequencies of non-interest and interest results can be 0.382 and 0.618, the expected value of the lower bounds of the 95% confidence interval with sample size of 200 blocks and anticipated kappa values are shown in Table 2. With 50 patients/4 blocks per patient, the expected value of the lower bounds of the 95% confidence interval are also shown in Table 2. Training can include 2 OCT image volumes plus digitized and classified histology slides from the first 50 patients imaged using the exemplary UHR OCT system, yielding a total of 100 training volumes with corresponding histology. After training, each reader can be provided with a blinded testing module of 200 OCT volumes randomly selected from the next 50 patients, and required to score each volume as interest (e.g., score 1) or non-interest (e.g., score 0), where interest and non-interest are defined in Table 1.

The kappa statistic can also be used to quantify agreement on three categories. When the frequencies of positive, ambiguous and negative results are (e.g., 0.3, 0.2, 0.5). The expected lower bounds are provided in Table 3 below. The OCT-generated images with histology agreement can be selected and used for training and testing of the exemplary convolutional neural network (CNN) procedure as described below. As shown in Table 3 the kappa statistic can also be used to quantify agreement on five categories, which include 0.382,0.079,0.053,0.381,0.105. The expected value of the lower bounds of the 95% confidence interval with different sample sizes and anticipated kappa values are also shown in Table 3.

Exemplary OCT Imaging System. Both high speed and high resolution can be utilized for this pathology application. It has been observed that peak variance intensity at high speeds can be significantly higher for supercontinuum lasers than superluminescent diodes. This can facilitate an exemplary system with poor signal to noise ratio, when imaging at fast speeds. Therefore, the exemplary system can include an InPhenix INP-860552047 multiplexed superluminescent diode with about 850 nm central wavelength (plus or minus about 10%) and about a 100 nm 3 dB bandwidth (plus or minus about 10%) and about a 7.5 mW output power (plus or minus about 10%).

The exemplary wavelength can be in the range of about 700 nm (plus or minus about 10%)–1400 nm (plus or minus about 10%). The exemplary system, method, and computer-accessible medium can utilize the near infrared spectrum in order to avoid water absorption to facilitate larger penetration depth. An image penetration of about 1 mm can be utilized needed, to facilitate that the OCT imaging volume can correspond to the histology images (e.g., as tissue blocks are routinely shaved to be flat before generating a histology slide.) Once the center wavelength can be chosen, an axial resolution under 5 microns can be beneficial. However, a larger axial resolution too, for example, up to about 10 um (plus or minus about 10%) can be used. The accuracy can decrease as compared to sub-5 microns. Higher axial resolution (e.g., sub-5-micron) can be beneficial when classifying samples into risk classes. Imaging at longer wavelengths can facilitate a larger penetration depth, but the scattering contrast can be lower. A wavelength range of 800 nm (plus or minus about 10%) to about 900 nm (plus or minus about 10%) can provide beneficial image penetration and scattering contrast for applications in pathology. The minimum speed that can be feasible, is what can facilitate OCT imaging of a 25 block case in under 30 minutes for single sided imaging. A minimum speed to fit within the clinical workflow can be around 80 kHz (plus or minus about 10%)–100 kHz (plus or minus about 10%). A reduction in acquisition rate can be possible by reducing the sampling density of the images and thus facilitating the exemplary classification as interest/no interest or within risk classes.

A high-speed spectrometer (e.g., Cobra-S 800, Wasatch Photonics) can be used to measure the interference signal with a maximum A-line rate of about 250 kHz (plus or minus about 10%), about a 180 nm bandwidth (plus or minus about 10%), and about <0.09 nm spectral resolution (plus or minus about 10%). The axial resolution and lateral resolutions of the system was measured to be about 5.5 µm (plus or minus about 10%) in air. The signal-to-noise ratio ("SNR") of the system was 95 dB, and the 10 dB sensitivity roll-off was 1.1 µm. The field of view can be about 10 cm by 10 cm.

Exemplary OCT Imaging Protocol. The exemplary OCT system and method according to exemplary embodiment(s) of the present disclosure can be provided within the pathology suite, and can be used to image primarily formalin-fixed and occasionally fresh unfixed tissues after they have been placed in blocks by physician's assistants on the basis of existing clinical selection criteria. Multiple 3D OCT volumetric images can be acquired on both the top and bottom sides of the specimen blocks. In addition, whole slices can be imaged covering both sides of the entire surface area of the slices. For the UHS OCT system, OCT volumes can be taken at 250 kHz linerate. Each volume can cover 3 mm-by-3 mm-by-2 mm in space, with an acquisition time of 2.56 seconds per volume. To scan one surface of a tissue cassette of average size 2.5 cm×2.5 cm, it can take approximately 1 minute. The scan time for an average of 20 cassettes per case, with double sided OCT imaging needing approximately 43 minutes. If the time needed for OCT imaging can be determined to be an issue, sampling density requirements can be reduced, as needed, to maintain a high predictive value.

Exemplary Histology Retrieval and Annotation

Exemplary Histological Analysis. Histological processing of breast specimens can follow standard clinical procedures, and may not be altered due to optical coherence tomography imaging analysis and interpretation. Tissue grossing can be carried out by a physician assistant in the Pathology Department. Following standard procedures for specimen orientation, margin inking, and serial slicing, each slice from the lumpectomy specimen can be examined and fixed with formalin. Areas of interest and additional random sections can be submitted into cassettes, processed and paraffin embedded to generate tissue blocks as per standard of care protocol. At least one H&E section can be generated from each block.

Exemplary Pathological Annotations: Every histologic section (e.g., corresponding to a block) can be reviewed by a breast pathologists, and annotated individually with respect to the presence of any and all of the 25 key histologic lesions (e.g., assigned a numerical value as per Table 1). Each block and corresponding H&E slide can be annotated for the histology class or classes present, which can be also assigned a numerical value. If there can be a need to further annotate a class, for example to describe size, free text in comment can be used. If the class was not initially given a definition, it can be added at a later time, or an existing class with comment can be used, if appropriate. The extent of the histology class can be qualitatively annotated with F=focal, M=multifocal, D=diffuse extensive.

TABLE 3-continued

Cohen's kappa analysis to determine further sample size

| 150/3600 | Targeted K | | | | | |
|---|---|---|---|---|---|---|
| (patients/blocks) | 0.4 | 0.5 | 0.6 | 0.7 | 0.8 | 0.9 |
| 0 vs 1 vs 2 vs 3 vs other | 0.380 | 0.481 | 0.582 | 0.683 | 0.785 | 0.889 |

Exemplary Pathological Information: The histologic lesions identified through the pathological annotation of each H&E block can be used to establish the ground truth for the classification of each corresponding OCT block image. These exemplary classifications can be performed by human experts and the deep learning procedure described herein. Two OCT classification procedures can be used: (i) a binary "call" that the image does or does not contain regions of interest, and (ii) a more granular five-class "call" procedure of the global risk classification of the features present in the

TABLE 1

Histology class definition/(risk category) and OCT image class annotation number

| OCT Labels | No-interest | Interest | | | |
|---|---|---|---|---|---|
| Binary Analysis OCT Labels Risk Analysis | 0 = No Increased Risk | 1 = Mild Increased Risk | 2 = Moderate Increased Risk | 3 = High risk (carcinoma in situ or invasive) | Other |
| Histology Labels | 1. Fibrous tissue 2. Cicatrix 3. Adipose 4. Fat necrosis 5. Ducts and lobules 6. Cystic change up to minimally proliferative 7. Cystic and papillary apocrine metaplasia | 8. Proliferative systic change 9. Intraductal papilloma 10. Radial scar 11. Fibroadenoma 12. Proliferative cystic change | 13. Proliferative cystic change with atypia 14. Atypical lobular hyperplasia | 15. Ductal carcinoma in situ 16. Lobular carcinoma in situ 17. Invasive ductal carcinoma NOS 18. Invasive ductal carcinoma special type(in note place type) 19. Invasive lobular carcinoma Phyliodes tumor 20. Calcifications (high risk if associated with carcinoma) | 21. Clip site other than classical 21. Clip site other than classical cicatrix(e.g. Hydromark) 22. Inflammation 23. Biopsy changes 24. Calcifications 25. Other(in note) (assign based on risk level) |

TABLE 2

Cohen's kappa analysis to determine sample size

| | Targeted Kappa | | | | | |
|---|---|---|---|---|---|---|
| Patients/Blocks | 0.4 | 0.5 | 0.6 | 0.7 | 0.8 | 0.9 |
| 50/200 | 0.286 | 0.39 | 0.496 | 0.604 | 0.716 | 0.833 |

TABLE 3

Cohen's kappa analysis to determine further sample size

| 150/3600 | Targeted K | | | | | |
|---|---|---|---|---|---|---|
| (patients/blocks) | 0.4 | 0.5 | 0.6 | 0.7 | 0.8 | 0.9 |
| interest vs no interest | 0.373 | 0.475 | 0.577 | 0.679 | 0.782 | 0.886 | image (e.g., 0=none, 1=mild, 2=moderate, 3=high, and other=a variety of entities of interest.

As shown in Table 1, for the region of interest classification, non-interest can be defined as histology class 1-7 (e.g., mostly risk category 0 but including histology class 7(1)). For the global risk classification, category 0 can represent no increased risk lesion, including non to minimally proliferative cystic change; category 1 can represent mild increased risk lesions including proliferative cystic change, radial scars, and benign neoplasms like intraductal papilloma or fibroadenoma; category 2 can be moderate increased risk, including atypical ductal/lobular hyperplasia ("ADH/ALH") as well as classical LCIS; and category 3, high risk, can be any ductal carcinoma in situ or invasive carcinoma. In addition, the "other" category including biopsy site changes, inflammatory lesions, calcifications and clip site can be included in the region of interest despite not being associated with increased risk as they represent lesions that can be targeted for removal and at time mark the radiographic lesion and define the excision site to be removed. For example, the highest risk lesion per slide can determine the global category. Any lesion not fitting these classifications can be annotated separately.

Exemplary Labeling OCT En Face Images and Generation of Database. Each OCT-generated stitched volume corresponding to a sample specimen within a cassette can be labeled based on the corresponding H&E labels outlined in Table 1. An en face image representing the volume can be chosen, which can be in the same plane (e.g., x-y) as the H&E slide. Each en face OCT-generated image can be given image level labels as opposed to pixels being individually labeled. It can be estimated that approximately 40% of blocks can be of the non interest category, and that mild, moderate and high risk categories represent approximately 20%, 10%, 25%, respectively; 5% can be expected to fall in the other category.

The exemplary OCT imaging protocol can be incorporated into a workflow of pathology grossing. In an exemplary study, OCT-generated imaging of image tissue specimens within the pathology suite was shown directly after surgery.

Exemplary Fresh fixed vs. unfixed tissue. Most prior studies of OCT imaging of breast specimens, including the exemplary studies, were conducted on fresh, un-fixed specimens. Within this study, to fit within the pathology workflow can image specimens that have been fixed from 6 to 72 hours. The exemplary OCT imaging shows that the features of breast tissue can be similar between fresh and formalin fixed breast tissue, and a slight increase in image penetration within formalin fixed specimens was observed.

Exemplary Multi-Reader Study. A database was created from 65 surgically excised breast specimens acquired and imaged at two sites (e.g., site one including 19 patients and site two including 16 patients). After imaging, the tissue samples underwent histological processing and annotation, which established the ground truth that the database contained 16 malignancies (e.g., eight invasive ductal carcinomas; four DCIS; four mixed invasive ductal carcinomas and DCIS). The OCT-generated images were paired with the corresponding histology slides to form 90 cases. Eight readers (e.g., two pathologists, two surgeons, three radiologists, and a research scientist) were trained to recognize the OCT features of suspicious or non-suspicious tissues with 70% accuracy in a training set of 30 cases, which needed an average of 3.4 hours. Results from the evaluation of the remaining 50 cases showed that trained human experts were able to use OCT-generated images to identify suspicious breast tissue with 82-94% accuracy, sensitivity, and specificity. However, such evaluation was time consuming (e.g., utilizing an average of 1.9 hours for the 50 cases) and subject to inter-rater variability. Radiologists achieved the highest accuracy, probably because the grey scale OCT-generated images used in this study were similar to the grey scale ultrasound images they typically use in breast imaging.

In contrast to the manual review described above, the exemplary UHR OCT-generated images described herein can facilitate a similar advantage to pathologists, who can be used to working with images with cellular level resolution, and that the deep learning procedure described below to classify images with similar accuracy, but greater speed and less variability, than humans.

As described herein, the combination of higher resolution images and images presented in the same orientation as standard histology, with a large field of view (e.g., 4 cm×4 cm) surface area, can facilitate easier training of readers and a higher accuracy compared to the prior multi-reader study (e.g., 82-94%).

Exemplary Use of AI for the Classification of OCT-Generated Images

The application of AI image recognition procedures to provide automated high-throughput analysis of radiological images has had a profound impact on the field, and the extremely large image datasets produced by OCT systems and methods can be appropriate for this big-data approach. The exemplary system, method, and computer-accessible medium according to exemplary embodiment(s) of the present disclosure can utilize deep learning to recognize cancerous tissue, which can also be adapted to recognize other features, which can further guide and increase the efficiency of subsequent pathological examination.

The exemplary system, method, and computer-accessible medium, using an automated procedure, can facilitate a reduction in UHR-OCT image interpretation time, and an increase in accuracy, compared to trained human readers. Thus, high negative predictive value can be facilitated. To avoid the challenges and time needed for pixel by pixel manual labeling, a weakly-supervised deep learning procedure can be utilized, which can be given for the entire image. Areas under the curve above 0.98 can be achieved using a weakly supervised approach to evaluate clinical-grade computational pathology on prostate cancer, basal cell carcinoma, and metastatic axillary lymph nodes. Weakly supervised deep learning can have an advantage over conventional fully supervised learning facilitating pathologists to exclude 65-75% of slides while retaining 100% sensitivity. Similarly, improvements to the exemplary deep learning procedure can be facilitated by fine tuning the exemplary procedure using a weakly supervised approach.

Exemplary Results

The exemplary CNN procedure according to exemplary embodiment(s) of the present disclosure described herein can illustrate the use of deep learning for classifying OCT-generated images of breast specimens. De-identified human breast tissues from mastectomy and breast reduction specimens were excised from patients. The specimens included both normal tissues and non-neoplastic tissues, and were not needed for diagnosis by the Department of Pathology. A total of 82 specimens from 49 patients were used in this protocol, including normal tissue specimens derived from normal breast reduction (e.g., n=40) and pathological tissue specimens from mastectomy (e.g., n=42), with an average size of 1.2 cm$^2$. A custom UHR-OCT system with an axial resolution of 2.7 μm and a lateral resolution of 5.5 μm was used. The exemplary procedure used an A-scan-based classification procedure and the CNN was implemented using an 11-layer architecture consisting of serial 3×3 convolution kernels. Four tissue types were classified, including adipose, stroma, ductal carcinoma in situ ("DCIS"), and invasive ductal carcinoma ("IDC"). The mean five-fold validation F1 score was highest for IDC (e.g., 0.89, mean standard deviation, ±0.09) followed by adipose (e.g., 0.79±0.17), stroma (e.g., 0.74±0.18), and DCIS (e.g., 0.65±0.15). Additional binary classification of cancer (e.g., DCIS and IDC) versus non-cancer (e.g., adipose and stroma) evaluation was performed yielding a higher diagnostic performance of 94% accuracy, 96% sensitivity, and 92% specificity. As shown herein, an exemplary CNN based procedure can be used to accurately distinguish cancerous regions in OCT-generated images.

Exemplary Deep Learning Procedure

An exemplary weakly supervised deep learning procedure can be used to classify image volumes of breast specimens into a binary classification of 0 (e.g., non-interest) and 1 (e.g., of interest). The exemplary deep learning procedure can be used to classify images into five risk categories: (e.g., 0: no risk, a region of non-interest; 1: mild increased risk; 2: moderate risk; 3: carcinoma in situ or invasive, 4 other as outlined in Table 1). Using a weakly supervised approach, a Densenet-121 network can be utilized. This network can maintain simplicity while utilizing modern dense blocks which enhance gradient propagation through very deep neural networks. Previous studies have successfully used DenseNet for classification of OCT-generated images of retinal disease pathological cystoid fluid in the retina can implement a DenseNet for classification of pathology risk factor in OCT-generated images. A beneficial parameter for choosing an exemplary network can be computational efficiency, given the fact that the exemplary network can be run in a clinical setting and efficiency of the exemplary platform can be critical. Briefly, skipped connections were introduced with the exemplary Resnet architecture in order to promote gradient propagation in deep networks. These connections facilitated gradients to skip over intermediate layers of a residual block during the back propagation, facilitating small updates to travel through very deep networks without vanishing or exploding. Dense blocks can be used, but instead of only bypassing a single residual block at a time, gradient updates can bypass any number of dense blocks, facilitating a direct connection between deepest and shallowest parts of the network. This can be performed by duplicating feature maps of every layer to every deeper layer.

According to an exemplary embodiment of the present disclosure, many or all OCT-generated images can be pre-processed prior to inputting to the network. The dataset can be derived from one two-dimensional ("2D") image in the x-y plane (e.g., en face image) that corresponds to histology for each tissue block. Each en face image can be divided into overlapping tiles of size 512×512 pixels. The images can be intensity normalized by dividing by the maximum value within the volume. This can facilitate all the images, regardless of variability in scanning parameters, to all occupy the same limits of signal between 0 and 1.

The exemplary DenseNet Architecture can include a 2D dense block using 3×3 convolutions. Within each composition layer, a pre-activation batch norm, ReLU, and 3×3 convolution can be formed to produce output feature maps with increasing number of channels. Between contiguous block layers, 1×1 convolution followed by 2×2 average pooling can be used to reduce feature map size and improve computation efficiency. Several instances of each network can be trained, which can be analogous to multiple human experts reviewing and voting on image labels to further improve performance. Each instance can have different weight initializations and a different order of inputs. The exemplary classification result can be determined by averaging the probabilities estimated by these five models. The loss function can be softmax cross entropy for the multi-class decision. Initial learning rate can be $10^{-5}$ and learning rate can be decayed in a step-wise fashion during training. The exemplary model can be trained in Tensorflow using the Adam optimizer using 1 NVIDIA Titan Xp GPU on a Linux work station with 15 GB RAM, 946 GB disk space, Intel Xeon Silver 4110 CPU.

The corresponding stitched OCT-generated en face image that can be matched to the histology image for the block can be given the same image based labels that appear within the histology report. For the purpose of image classification, the image can be classified based off the highest risk feature within the image.

Exemplary Statistical Analysis

OCT-generated images generated from 3000 blocks can be tested. The ratio of training, validation and testing sets will be 70:20:10. A binary classification task (e.g., interest vs. non-interest) can be performed, followed by a more granular analysis of the accuracy of OCT-based "calls" on a per histology class and risk category basis, as determined by the histopathological gold standard, and evaluate sensitivity and specificity. The exemplary classification procedure can be performed on the testing set and evaluated for accuracy for each risk category. The accuracy and inter-rater reliability of OCT-based classification of breast samples in all histology classes and risk categories, not merely those qualifying as non-interest, can be determined.

The exemplary procedure utilized for binary classification (e.g., interest vs. non-interest) can perform better than the procedure developed for a five-fold classification by risk category, because it may not be known, a priori, how many examples of each category can be present in the exemplary training and validation sets. Successful demonstration of a binary classification procedure can be directly relevant to the exemplary planned use case of OCT image-guided triage of regions unlikely to contribute diagnostic information, while the exploratory results from the risk classification procedure can aid in the evaluation of the cost-benefit ratio of this exemplary approach.

Various modifications can be implemented if the exemplary deep learning procedure's diagnostic performance can be significantly inferior to the human diagnostic performance. A supervised approach can be used with manual annotation of the OCT image's region of interest to generate the training data. This approach can provide superior diagnostic performance. Different exemplary neural networks can also be evaluate including Resnet, to determine the optimal network for the OCT-generated images. In addition, an ensembling network can be utilized, taking advantage of the 3D nature of the exemplary OCT image datasets. This can extend the exemplary network to take in both B-scans and en-face images to improve classification.

Using the exemplary system, method, and computer-accessible medium, an analysis of blocks eliminated from further analysis by a binary classification result determined by human interpretation and deep learning procedure can be analyzed. Additional analysis can be performed for five category classification results determined by the exemplary deep learning procedure.

Exemplary benefits of the exemplary system, method, and computer-accessible medium can be calculated by the average absolute and average relative number of blocks that were classified as non interest in the entire cohort. For example, the absolute number of blocks eliminated by OCT (e.g., "called" as non interest) in each case can be summarized, and the average number of blocks eliminated in the entire cohort can be analyzed. The relative rate of block elimination per case can be determined by dividing the number of blocks eliminated by the total number of blocks, and calculating the average number of blocks eliminated in the cohort. Estimates of dollar savings can be provided for gross room and laboratory processing and pathology review time per case and on average for entire cohort. Estimates of processing savings can be based on 2019 Medicare reimbursement of technical cost for a lumpectomy processing of $186.68 and given approximately 30 blocks per lumpectomy, the cost per block can be estimated to be $6.22 and the pathology review time to be 0.5 min/slide.

Cost can be assessed by two methods the absolute and relative average number of "non-interest" blocks that was classified incorrectly on a per case basis and on the entire cohort basis, can be determined. The histology most commonly associated with errors can be summarized. Specifically, the absolute number of blocks classified incorrectly (e.g., classified as non interest on OCT but containing pathology of interest on histology) can be summarized per case and on average for the cohort. Also, the relative number of blocks classified incorrectly can be calculated by dividing the number of incorrect classifications by the total number of blocks classified as non-interest, both per case and on average in the cohort.

Exemplary Case level analysis. On a per case basis, the impact of block elimination relative to the entire case on diagnosis, grade, tumor size, and margin status to determine overall whether the exemplary OCT procedure has produced meaningful clinical impact can be determined. By determining diagnosis, grade, stage, and margin status based on non-eliminated slides and comparing the results to the whole case including all slides, a determination can be made as to which of these parameters were impacted by the OCT non-interest calls and how meaningful the impact is. Impactful changes can be defined as a change in basic diagnosis (e.g., no cancer, in situ versus invasive carcinoma), a meaningful change in size (e.g., defined as a change from one pT stage category to another, e.g. pT1a to pT1b), a meaningful change in grade (e.g., defined as a change from grade 1 to 2 or 3), or a meaningful margin change (e.g., from positive or negative status). Summary data across all cases/cohort can also be provided. The above analysis can provide a clear picture of the benefits of utilizing OCT and the cost so it can be assessed objectively.

Exemplary Results

The exemplary system, method, and computer-accessible medium according to exemplary embodiment(s) of the present disclosure can impact clinical workload/flow by automating a key procedure in the gross breast tissue evaluation and facilitating pathologists to focus on the samples and regions most in need of analysis, cutting processing cost and pathologist review time. Deployment of high-speed, high-resolution OCT into routine clinical process can generate a large database of OCT-generated images of breast tissue and corresponding annotated H&E images of slides which can be used to drive further improvements in automated breast diseases/cancer detection. A 30% reduction in tissue blocks submission may not be associated with a significant error rate.

Exemplary Mechanism of Action, Modality, and Target

A high throughput technology for imaging lumpectomy samples that can accurately determine regions for further analysis or elimination can improve the process described herein, likely resulting in substantial cost and time savings in the laboratory and by pathologists. OCT is an ideal tool to develop for use within the pathology lab. OCT's exemplary resolution (1-10 µm) and exemplary penetration (e.g., 1-2 mm in tissue) bridge the gap between conventional bench-top microscopy and clinical high-resolution imaging tools such as ultrasound ("US"). Thanks to its high-speed and widefield imaging capability, OCT has been implemented in intraoperative settings as well as handheld probes and needle catheters to enable ex vivo and in vivo assessment of tumor margins. The exemplary system, method, and computer-accessible medium can utilize OCT to identify regions where further histological processing is unlikely to contribute to diagnostic and clinical decisions.

In an exemplary step-wise manner, the exemplary OCT systems and methods can triage the pathology specimen classifying normal or significant findings to prioritize pathologist's work load with initial attention on the suspicious tissue. The suspicious tissue can be further analyzed via histological processing and immunohistochemistry, facilitating the pathologists to focus their attention on the suspicious tissue enabling efficiency. The exemplary UHS-OCT system and method can be integrated into the pathologist workflow. Specifically, two potential places in the histology workflow have been identified as suitable for not interrupting current clinical practice: imaging fresh lumpectomy slices in cassettes, or imaging the sections during or after the fixation process.

The exemplary approach, according to an exemplary embodiment of the present disclosure, can be to image breast specimens within the pathology suite during grossing, and not merely whole lumpectomy specimens surface for margin. Such exemplary application can shift current clinical practice by addressing the need for image based guidance of sampling where gross/microscopic correlation may be poor, which leads to a high workload within diagnostic pathology. Utilizing the exemplary embodiments of the present disclosure, it is possible to effectuate (i) the clinical application for improved pathology grossing/processing instead of margin assessment, (ii) high resolution, high speed, and large surface area OCT imaging system, and (iii) automated AI based analysis. Within such exemplary embodiments, it can be possible to indicate that high speed and high resolution imaging by OCT, in combination with automated image analysis, can assist the diagnostic pathology process by identification of high probability region of interest and elimination of non-contributory regions.

Exemplary Clinical Application within Pathology Instead of Margin Assessment

The exemplary OCT evaluation in the breast realm so far has largely been in real time intra-operative margin assessment designed to reduce margin re-excisions in breast conserving surgery setting (lumpectomies) and to a lesser extent intra-operative sentinel lymph node assessment. These applications may be limited by the image penetration of OCT.

Real time high resolution fresh or fixed tissue OCT imaging can be adapted to a pathology suite setting can enhance the entire work flow of the diagnostic workup, especially but not limited to, of breast diseases and have significant impact on the accuracy and cost effectiveness of the entire process, well beyond past areas of interrogation. Assessment of breast resections (e.g., lumpectomies to mastectomies): identification of regions of interest for pathological histologic processing as a means of identifying regions of interest beyond what is suggested by gross analysis, prior clip location and conventional radiology. The comprehensive scanning with OCT of breast plates from serially sectioned lumpectomies or mastectomies, according to exemplary embodiments of the present disclosure, can facilitate a more accurate determination of high suspicion region beyond gross analysis and clip placement-substantially increasing accuracy and reducing block submission. This can result in reduced gross room work, histology laboratory processing cost/work and pathologist review time while maintaining if not increasing accuracy. In addition, OCT imaging has a higher image penetration than a typical histology slice. Therefore, a greater volume of the tissue can be evaluated by OCT to aid in the selection of sites for processing and also the number of levels, according to exemplary embodiments of the present disclosure.

Exemplary High Resolution, High Speed, Large FOV, OCT Imaging System

UHR OCT can categorize OCT systems and methods with axial resolution lower than 5 μm in air. UHR OCT can be beneficial for pathological evaluation of breast tissue because it can provide both higher resolution and better contrast to profile the inner tissue structures at a cellular level. OCT systems being commercialized for breast imaging (e.g., mainly for the application of margins) generally use light source centered at 1300 nm. With the exemplary embodiments of the present disclosure, it can be possible to obtain images of breast specimens that can be easier to interpret by computer procedures and human readers by imaging within the 800 nm spectral window, which provides higher axial resolution and increased contrast.

Exemplary deep learning procedures can be used, according to exemplary embodiments of the present disclosure, to automate image analysis to (i) identify normal areas that do not need to be processed and (ii) suspicious areas. Exemplary procedures can be used with a high negative predicative value, therefore identifying normal areas with high accuracy. This exemplary approach can be a different approach from most OCT image analysis methods. By identifying normal areas, it can be possible to reduce the workload within the pathology suite, by providing feedback on which areas of the lumpectomy should not be sent for further histopathological processing. This can result in, for example, a 30-50% workload reduction.

FIG. 1 shows a set of an exemplary system and an exemplary flow diagram of the use of a large field-of-view optical coherence tomography system according to an exemplary embodiment of the present disclosure. As shown in FIG. 1, large field of view OCT can be facilitated by tiling and stitching together multiple volumes. At procedure 140, samples can be placed under the OCT sample arm 110. Exemplary embodiments of samples can include whole surgical specimens 111, sections of surgical specimens 121, and/or regions of interest 131 placed within a cassettes, as well as others. At procedure 150, the required imaging field of view for the samples (e.g., samples 111, 121 or 131) can be determined by identifying the rough size utilizing markings 122 on the sample holder. At procedure 160, a linear translation stage 132 can be used to move the sample under the sample arms 110 and 120 to obtain tiled volumes. Automated z-axis translation can be performed for samples that have large topology such as sample 111. At procedure 160, automated stitching can be used to generate large mosaic 3D OCT datasets of the sample. At procedure 170, the stitched volume can be 170 or sent to an automated classification procedure at procedure 180.

Figure 2:
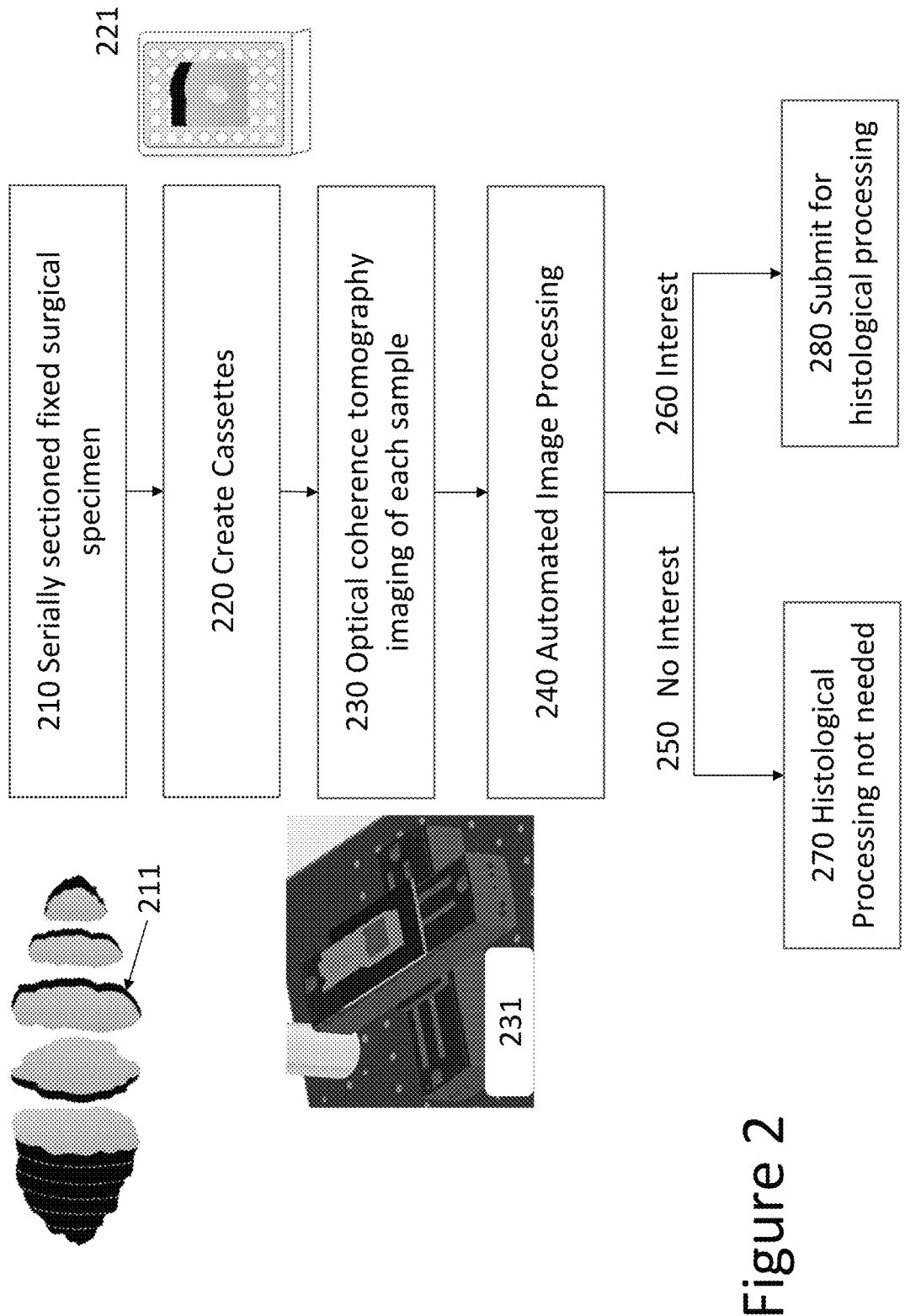
FIG. 2 is an exemplary flow diagram illustrating a clinical application of the exemplary optical coherence tomography system according to an exemplary embodiment of the present disclosure.

FIG. 2 illustrates an exemplary flow diagram providing the clinical application of the exemplary optical coherence tomography system according to an exemplary embodiment of the present disclosure. For example, at procedure 210, surgical sections can be serially sectioned to produce slices or bread loafs 211. Regions that can be selected for histological process follow standard of care to produce cassettes 221 at procedure 220. Samples can be formalin fixed within the cassettes. At procedure 230, cassettes can be opened and placed under the OCT scanner 231 for volumetric imaging. Then, the 3D OCT data set can be transmitted into an automated processing procedure at procedure 240. The automated processing procedure can classify the cassette as having tissue not of interest 250 or tissue of interest 260. Identification of blocks of non-interest to narrow selection to suspicious blocks using OCT can reduce histopathological workload, since these cassettes do not need histological processing at procedure 270. A reduction in workload can occur by identifying areas that are not of interest and do not need to be processed further by histology. At procedure 280, cassettes determined to be of interest can be submitted for histological processing.

Figure 3:
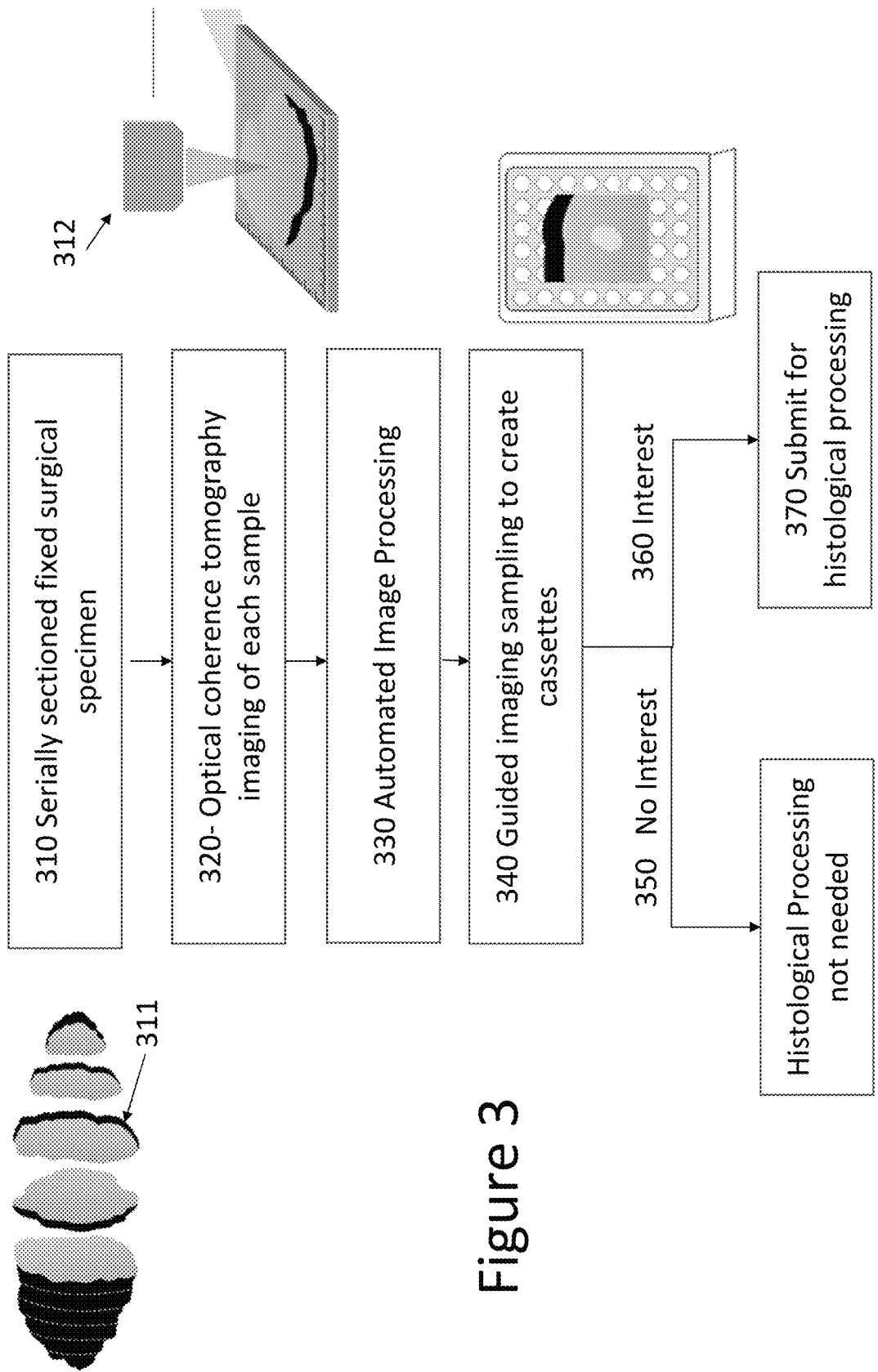
FIG. 3 is an exemplary flow diagram illustrating the clinical application of the exemplary optical coherence tomography system to identify regions of non-interest according to an exemplary embodiment of the present disclosure.

FIG. 3 shows an exemplary flow diagram illustrating the clinical application of the exemplary optical coherence tomography system to identify regions of non-interest according to an exemplary embodiment of the present disclosure. The identification of regions of non-interest can be used to guide selection of suspicious areas to be processed further by histology. At procedure 310, whole serial sections 311 of fixed surgical specimens can be sectioned, which can be imaged by OCT 312 at procedure 320. Regions of interest can be identified as having suspicious areas that can be made into blocks for automated processing at procedure 330. At procedure 340, guided imaging sampling can be used to create various cassettes in order to identify areas of non-interest 350 and areas of interest 260. Areas of non-interest 350 do not need histological processing. Areas of interest 360 can be histologically processed at procedure 380 using OCT.

Figure 4:
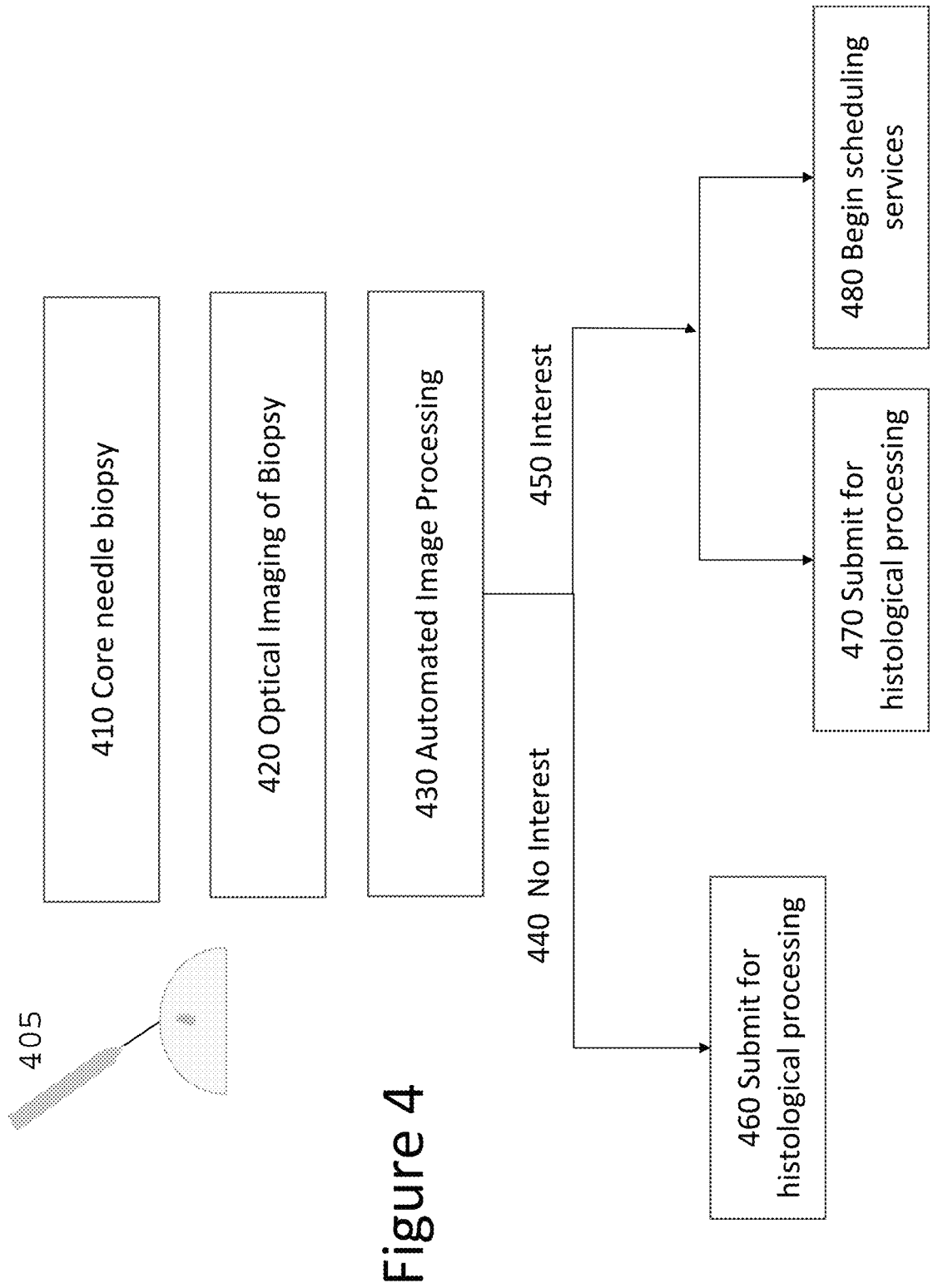
FIG. 4 is an exemplary flow diagram illustrating the clinical application of the exemplary optical coherence tomography system to rapidly assess breast core biopsy specimens according to an exemplary embodiment of the present disclosure.

FIG. 4 shows an exemplary flow diagram illustrating the clinical application of the exemplary optical coherence tomography system to rapidly assess breast core biopsy specimens according to an exemplary embodiment of the present disclosure. A core needle biopsy specimen 405 can be obtained at procedure 410. Rapid assessment of biopsy specimen 410 using OCT can be performed at procedure 420. A rapid diagnosis (e.g., less than about 10 minutes) can be provided to patients using automated image processing at procedure 430, thereby reducing patient anxiety, which is in contrast to standard turnaround time, which can be. Automated image processing at procedure 430 can identify areas of no interest 440 and areas of interest 450. Areas of interest 450 can be submitted for histological processing at procedure 470, and services for the patient can be scheduled at procedure 480.

Figure 5:
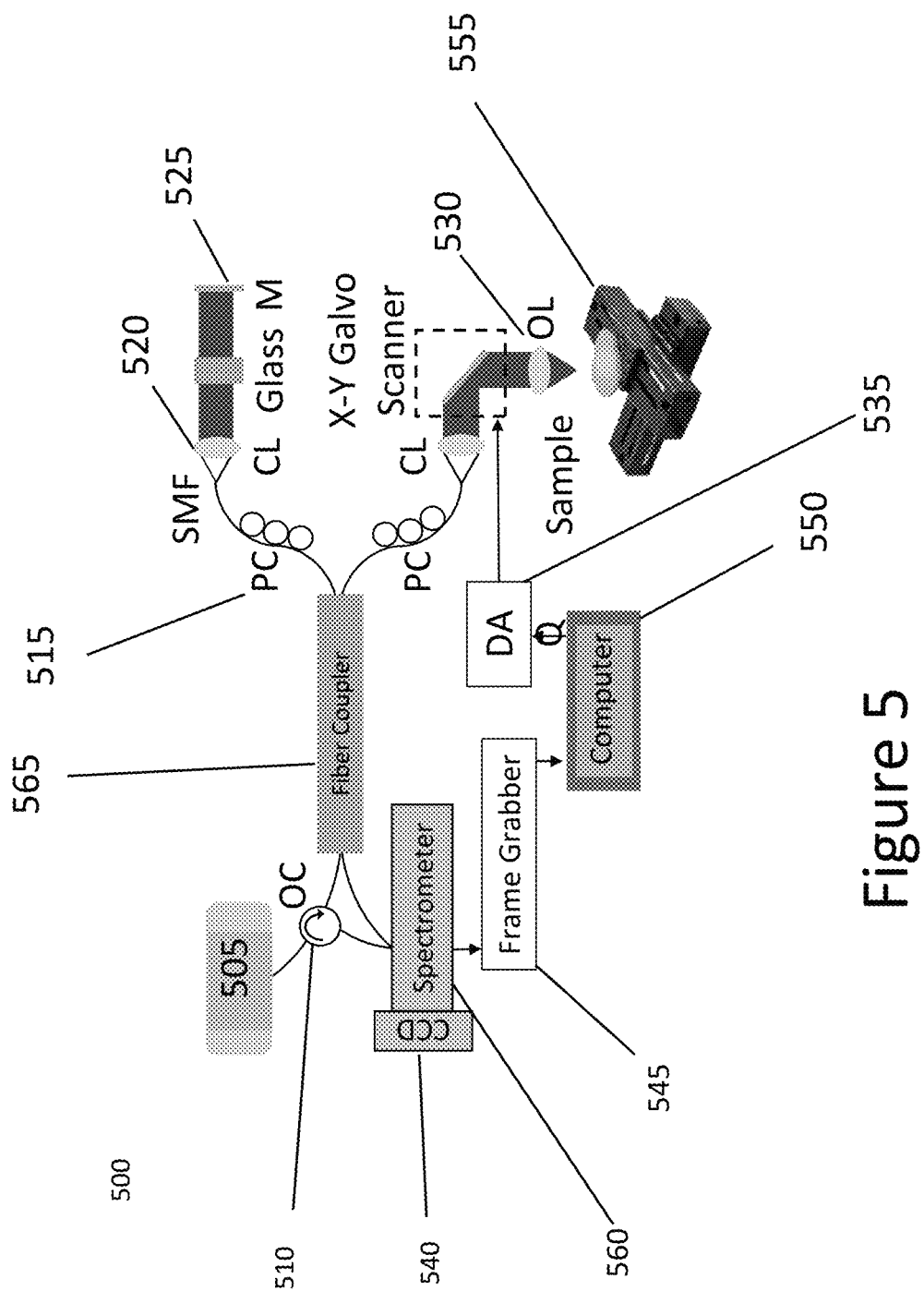
FIG. 5 is an exemplary diagram of the exemplary optical coherence tomography system according to an exemplary embodiment of the present disclosure.

FIG. 5 illustrates an exemplary diagram of the exemplary optical coherence tomography system 500 according to an exemplary embodiment of the present disclosure. Imaging within a clinical environment can be facilitated using an exemplary ultrahigh speed and ultra-high resolution OCT system that can facilitate imaging of a large field of view ("FOV"). Light source 505 can be a supercontinuum laser ("SLD") or a multiplexed SLD. The exemplary OCT system can also include an optical circulator ("OC") 510, polarization controller ("PC") 515, collimation lens ("CL") 520, mirror 525, objective lens ("OL") 530, data acquisition circuit and/or device ("DAQ") 535, and charge-coupled device ("CCD") 540. A frame grabber 545 can receive one or more frames from CCD 540 and provide it to computing device 550. The exemplary OCT system can facilitate a large FOV. A motorized 2D scanning stage 555 can provide up to 10 cm×10 cm range. The exemplary. An ultrahigh speed spectrometer 560 (e.g., a Wasatch spectrometer) can facilitate an A-line rate of 250 kHz and an imaging range of 2 mm. In addition, time-domain, spectral domain, swept source, polarization sensitive, phase sensitive, or elastography based OCT systems can be used as well. Exemplary SLD 505 can be a multiplexed superluminescent diode with 850 nm central wavelength and 100 nm 3 dB bandwidth and 7.5 mW output power. A high-speed spectrometer (Cobra-S 800, Wasatch Photonics) can be used to measure the interference signal with a maximum A-line rate of at least about 200 kHZ (plus or minus about 10%), or at least about 250 kHz (plus or minus about 10%), a 180 nm bandwidth (plus or minus about 10%), and less than about 0.09 nm spectral resolution (plus or minus about 10%).

As shown in FIG. 5, light from the SLD 505 can be provided to OC 510 and then to fiber coupler 565, where it can be split into sample and reference arms. The sample can be placed on sample stage 555, to facilitate the large FOV, as shown in FIG. 1. Reflected light from the sample and reference can combine and interfere within the fiber coupler 565. The interference single can travel through a third port of OC 510 to spectrometer 560. The spectral interferogram can be recorded onto computing device 545 using frame grabber 545.

FIG. 6 shows an exemplary table illustrating imaging time for the exemplary optical coherence tomography system according to an exemplary embodiment of the present disclosure. For the exemplary UHS OCT system and method according to exemplary embodiment(s) of the present disclosure, OCT volumes can be taken at 250 kHz linerate. Each volume can cover about 3 mm-by-3 mm-by-2 mm in space (plus or minus about 10%), with an acquisition time of about 2.56 seconds per volume. To scan one surface of a tissue cassette of average size 2 cm×2 cm, it can take approximately 41 seconds. The scan time for an average of 25 cassettes per case, single sided OCT imaging can be approximately 17 minutes.

Figure 7:
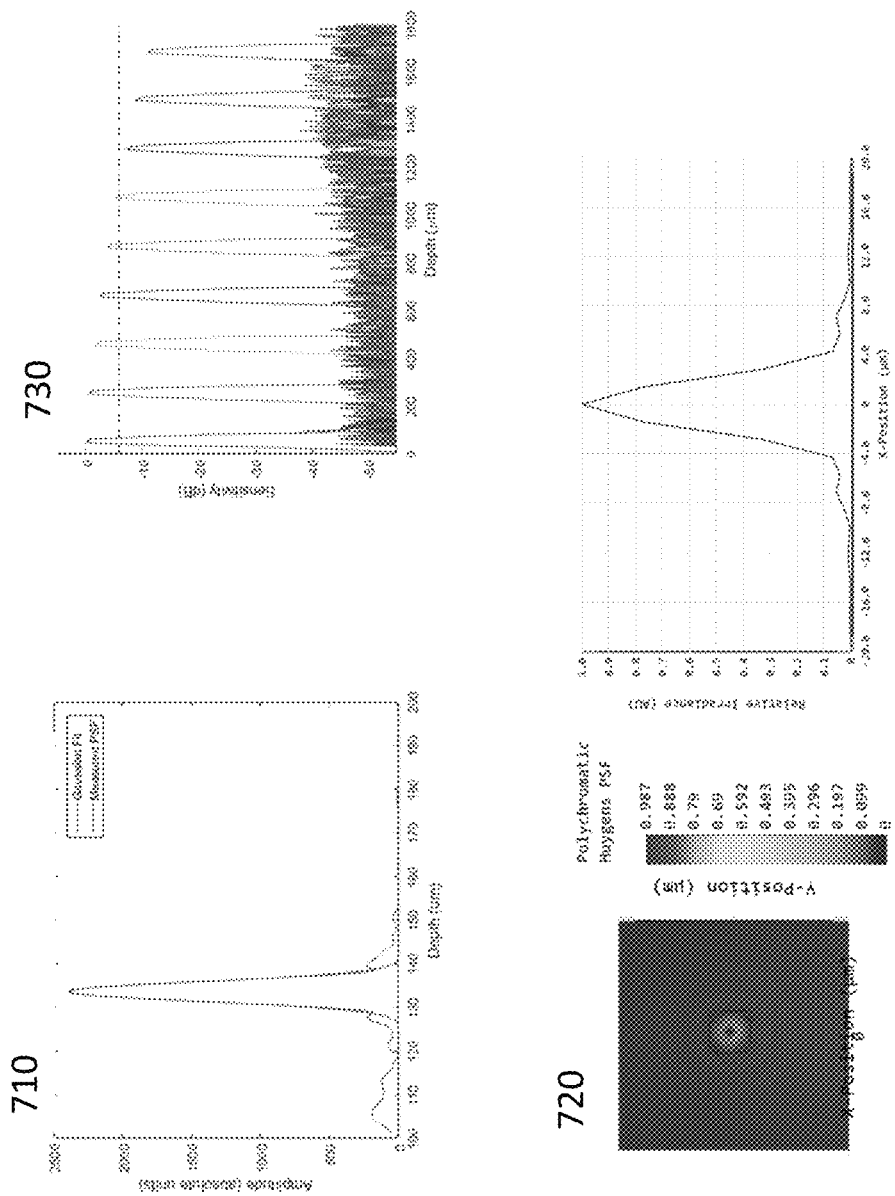
FIG. 7 is a set of graphs illustrating exemplary system specifications for the exemplary optical coherence tomography system shown in FIG. 5 according to an exemplary embodiment of the present disclosure.

FIG. 7 shows a set of graphs illustrating exemplary system specifications for the exemplary optical coherence tomography system provided in FIG. 5 according to an exemplary embodiment of the present disclosure. Graph 710 shows the axial resolution, and image and associated graph 720 shows the lateral resolutions of the system that was measured to be 5.5 μm in air. Graph 730 shows the signal-to-noise ratio ("SNR") of the system was 95 dB, and the 10 dB sensitivity roll-off was 1.1 mm.

Figure 8:
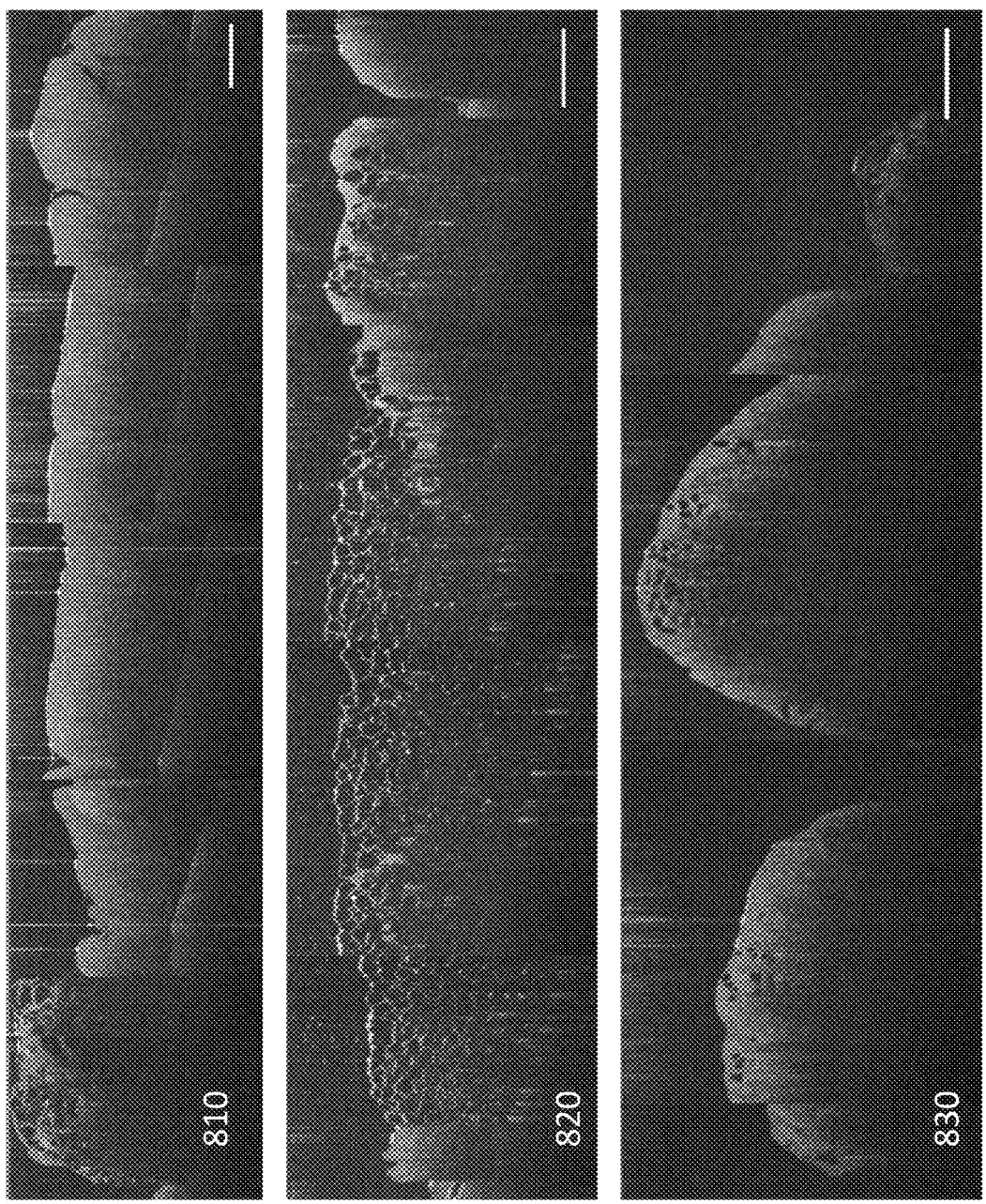
FIG. 8 is a set of exemplary stitched three-dimensional images of human breast core biopsies according to an exemplary embodiment of the present disclosure.

FIG. 8 shows a set of exemplary stitched three-dimensional images of human breast core biopsies according to an exemplary embodiment of the present disclosure, which were taken using the system shown in FIG. 5. Exemplary images 810, 820, and 830 are stitched B-scans from three different patients.

Figure 9:
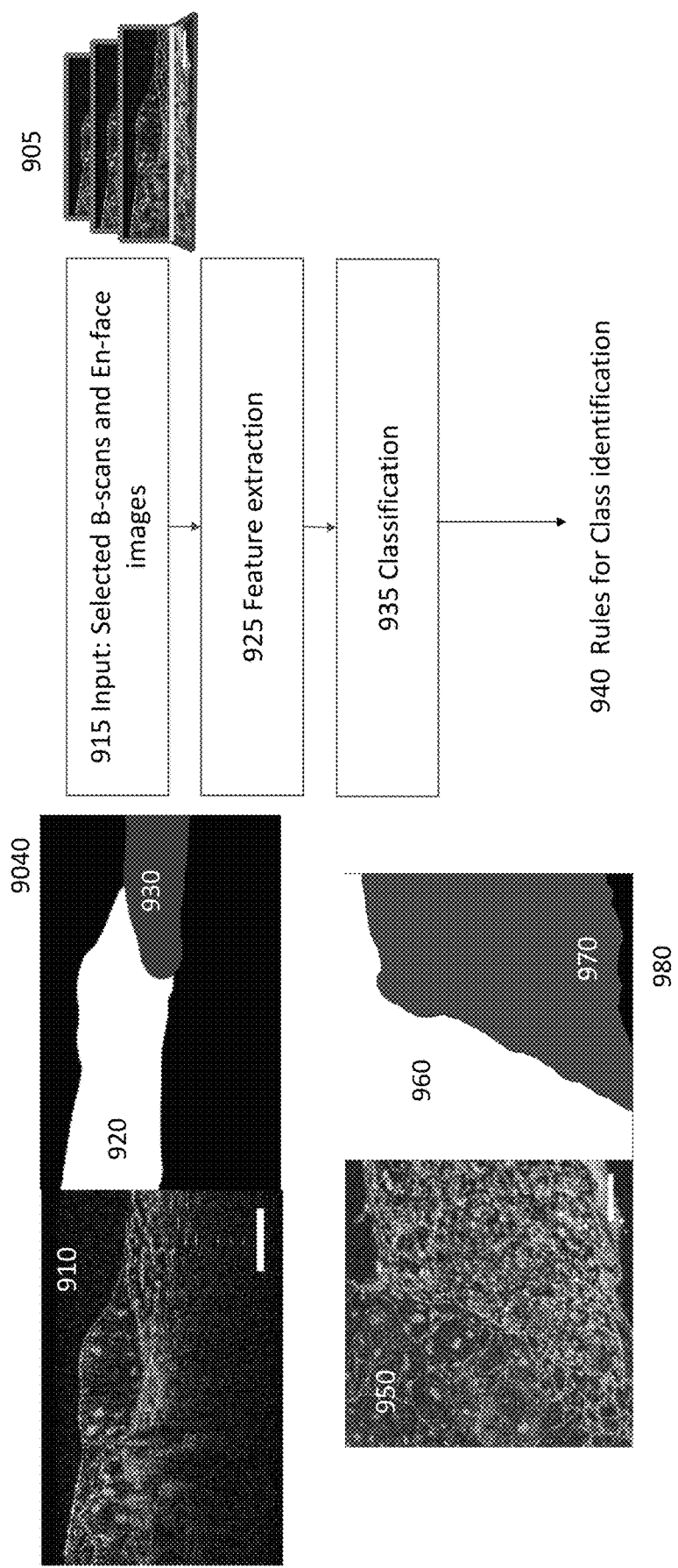
FIG. 9 is a set of training images for a classification procedure and a flow diagram of the exemplary classification procedure according to an exemplary embodiment of the present disclosure.

FIG. 9 shows a set of training images for a classification procedure and a flow diagram of the exemplary classification procedure according to an exemplary embodiment of the present disclosure. Inputs to the training procedure can include B-scans 910 and/or en face images 950. Individual pixels within the image (e.g., pixels 920, 930) and en face image (e.g., 960 and 970) can be labeled for a fully supervised procedure. The corresponding stitched OCT en face image that can be matched to the histology image for the can be given the same image based labels that can appear within the histology report. Exemplary images 960, 980 can be classified based off the highest risk feature within the image. Selected B-scans 905 and en face images, can be input at procedure 915 to the exemplary procedure, along with various labels. At procedure 925, feature extraction can be performed and then images can be classified at procedure 935 into classes. At procedure 940, the output from the training procedure can be or include the rules for classification. As shown in FIG. 9, the scale bar=about 500 μm.

Figure 10:
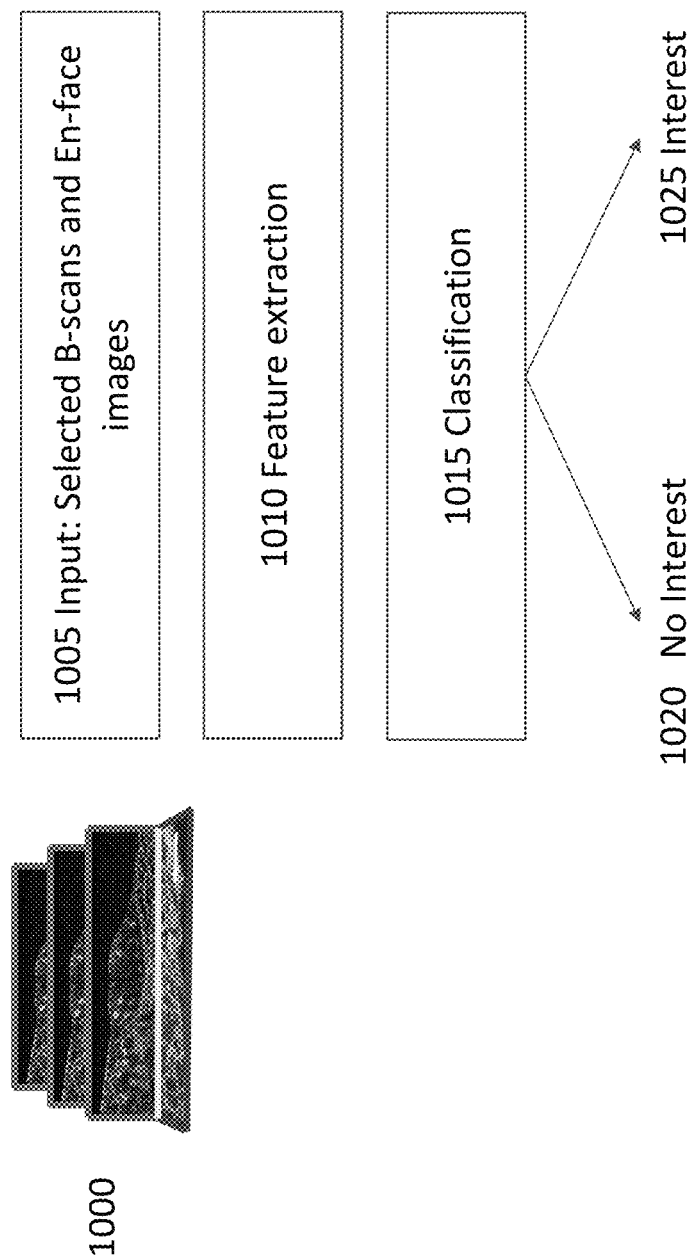
FIG. 10 is a set of volumetric images and method for an ensembling network according to an exemplary embodiment of the present disclosure.

FIG. 10 shows a set of volumetric images and a method for an ensembling network according to an exemplary embodiment of the present disclosure. OCT readers review both B-scan and en-face planes to interpret images. At procedure 1005, B-scan and en-face images 1000 can be input into the exemplary procedure. At procedure 1010, feature extraction can be performed, and an exemplary classification can be performed at procedure 1015 to identify areas of no interest 1020 and/or areas of interest 1025.

Figure 11:
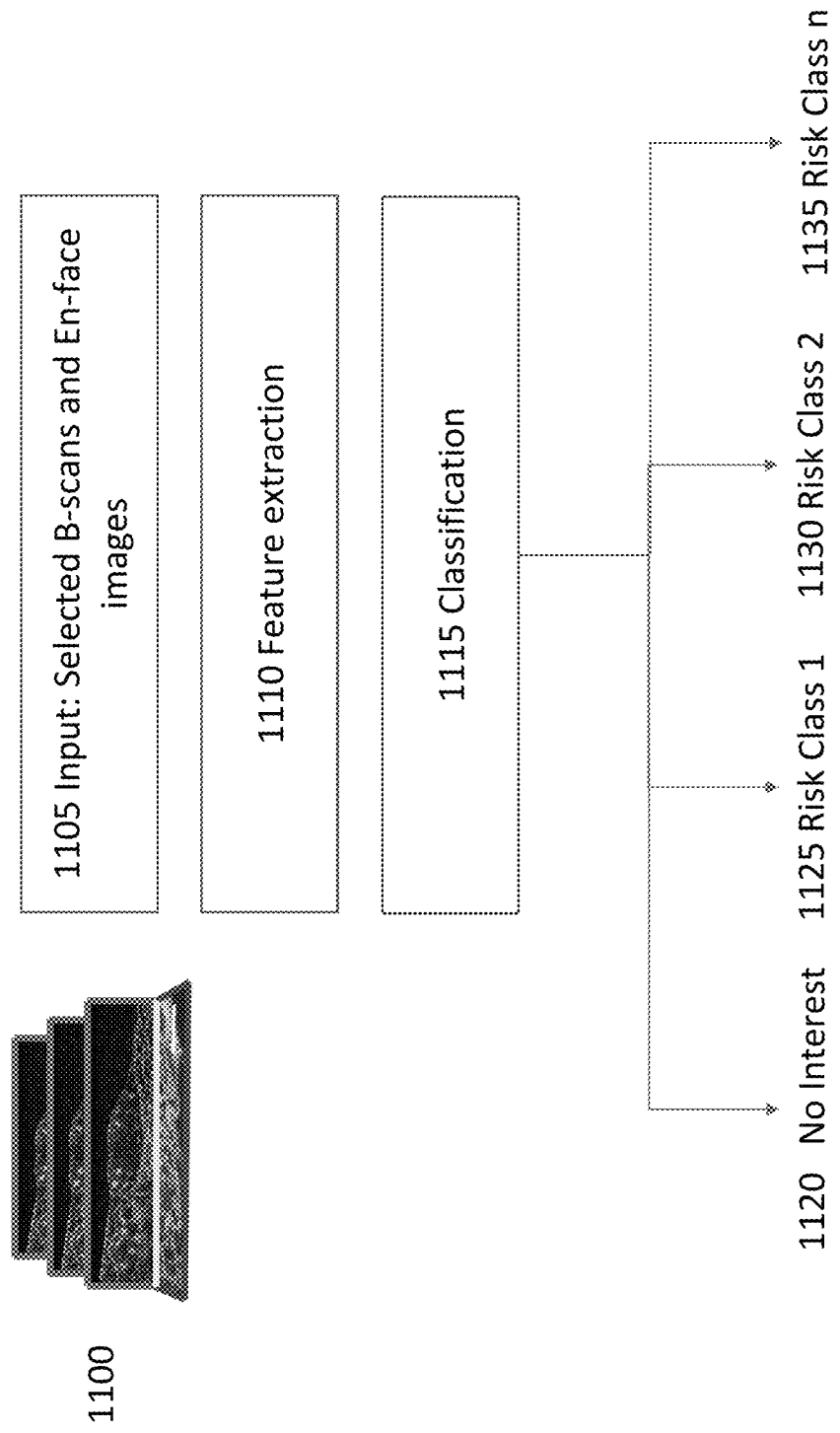
FIG. 11 is an exemplary flow diagram of a method for automated analysis of volumetric images according to an exemplary embodiment of the present disclosure.

FIG. 11 shows an exemplary flow diagram of a method for automated analysis of volumetric images according to an exemplary embodiment of the present disclosure. Automated analysis of volumetric images can be carried out to classify images as no interest 1120, risk class 1 1125, risk class 2 1130, or up to risk class n 1135. For example, for breast cancer, there can be 4 risk classes. Input b-scans and en-face images 1100 can be selected at procedure 1105. At procedure 1110, feature extraction can be performed. At procedure 1115, a classification procedure can be performed based on the training rules shown in FIG. 9.

Figure 12:
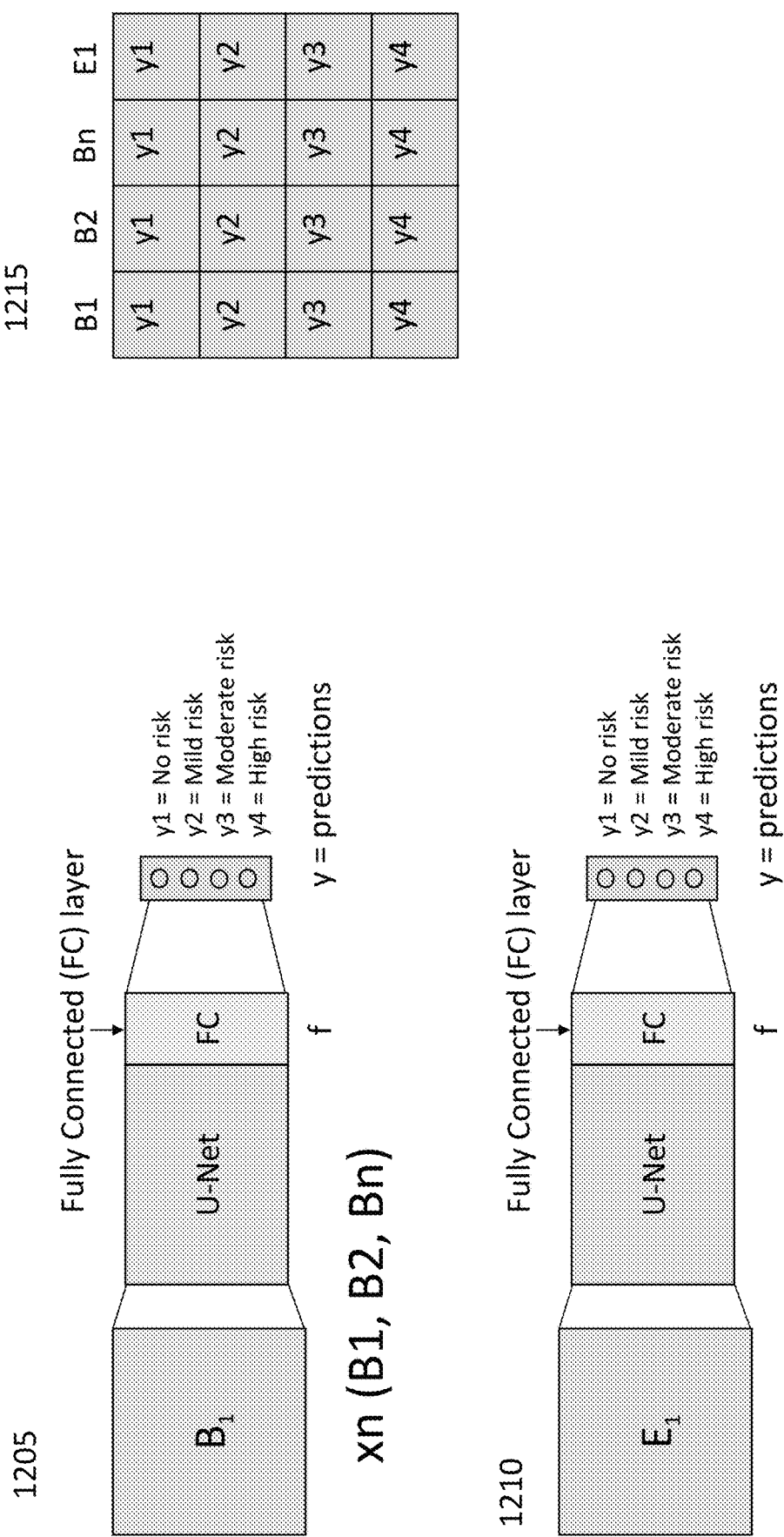
FIG. 12 is an exemplary diagram of an ensembling network according to an exemplary embodiment of the present disclosure.

FIG. 12 shows an exemplary diagram of an ensembling network according to an exemplary embodiment of the present disclosure. In particular, FIG. 12 shows an automated analysis of volumetric images is with ensembling network predictions. Networks can be determined developed individually to read selected B-scans 1205 and en face images 1210. B-scan+en-face networks can combine information from both planes to improve classification. Prior networks have focused only on B-scans. In contrast, the exemplary classification procedure can produce superior results by utilizing all of the information present in a volume to perform better than a single network trained on just B-scans. N B-scans can be included and M en face images can be included. In an exemplary embodiment, 3 B-scans and 1 en face image within the stitched 3D volume can be used. Linear predictors 1215 can be combined, and voting can be performed to classify the volume into one of the exemplary classes.

Figure 13:
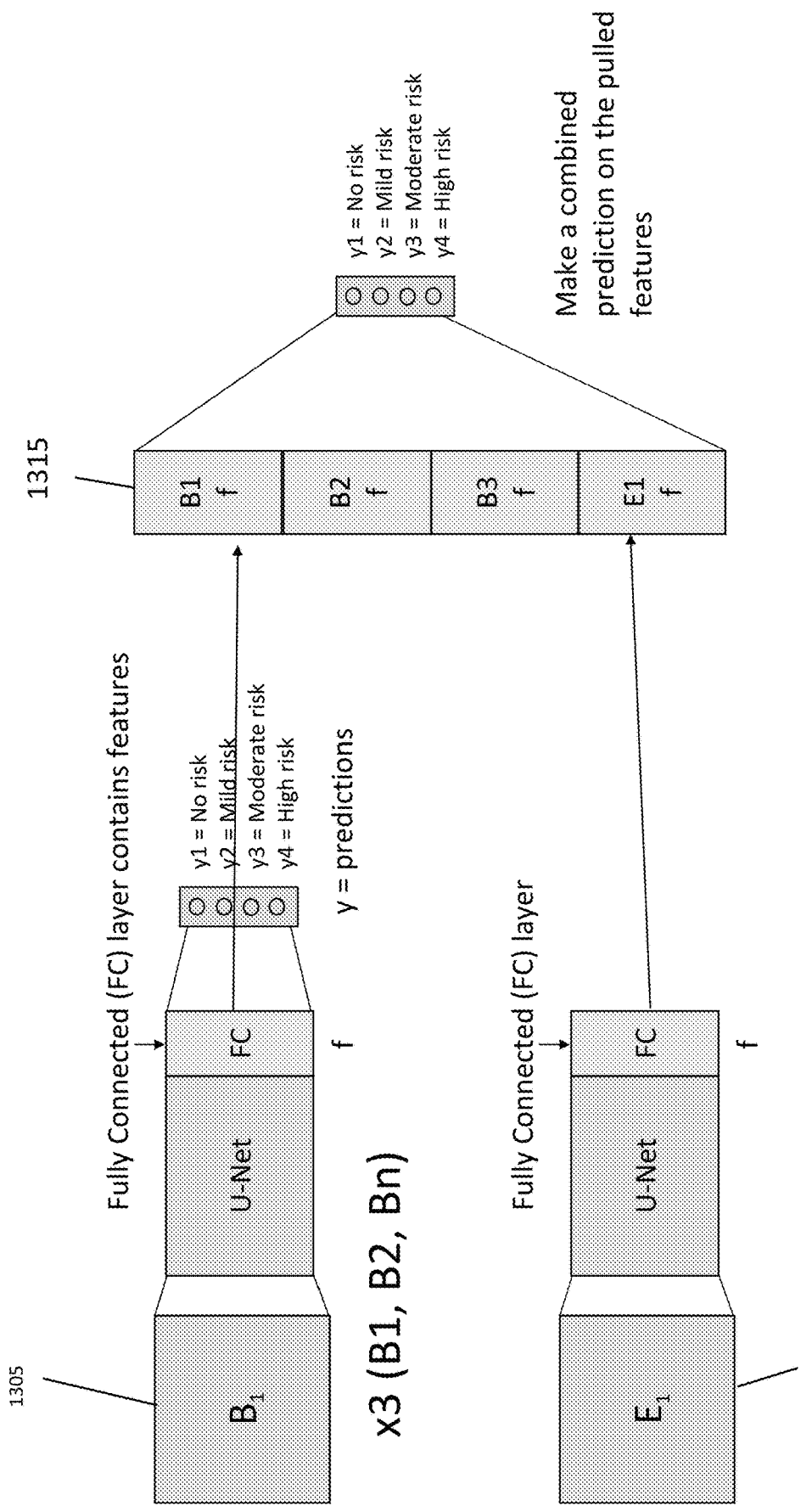
FIG. 13 is an exemplary diagram of an ensembling network containing features according to an exemplary embodiment of the present disclosure.

FIG. 13 illustrates an exemplary diagram of an ensembling network containing features according to an exemplary embodiment of the present disclosure. Ensembling the features can be beneficial by pulling features that can mesh the 2D features together to provide a superior 3D prediction. Networks can be developed individually to read selected B-scans 1305 and En face images 1310. B-scan+en-face networks can be generated that can combine information from both planes to improve classification. N B-scans can be included and M en face images can be included. In an exemplary embodiment, 3 B-scans and 1 en face image can be included within the stitched 3D volume. Linear predictors 1315 can be combined together as a feature vector to classify the volume into one of the classes.

Exemplary Three-Dimensional Compressed Sensing OCT using Predictive Coding

The exemplary system, method, and computer-accessible medium can utilize a novel approach to 3D CS OCT using a Denoising Predictive Coding ("DN-PC") approach to take advantage of the inherent structure in OCT volumes. By reconstructing the difference between adjacent b-scans in a volume, higher reconstruction accuracy can be achieved over traditional methods for a diverse collection of tissue samples including retina, cardiac tissue, uterine tissue, and ligament.

Exemplary Methods

The $\ell^1$ CS signal recovery can be a current approach, which can be expanded to predictive coding and the exemplary DN-PC. To initiate the exemplary CS signal recovery, vectorized images $x \in \mathbb{R}^N$ and $y \in \mathbb{R}^M$, which can be the full-resolution and undersampled images, respectively, can be used. The signal x can be recovered from y by solving, for example, the objective function:

$$\underset{x}{\operatorname{argmin}} \|y - Ax\|_2^2 + \|\Psi x\|_1 \qquad (1)$$

where $\Psi$ can be the sparse representation basis (e.g. DFT) and A can be an M×N matrix which can encode the undersampling pattern. Multiple methods exist for solving an objective function of this form such as Iterative Soft Thresholding ("IST") (see, e.g., Reference 25) or Alternating Directions Method of Multipliers ("ADMM"). (See, e.g., Reference 26).

For example, $x_t$ and $x_{t-1}$ can represent adjacent images in a volumetric scan and the difference image $\nabla x = x_t - x_{t-1}$. Thus, Eq. (1) can be modified to solve for $\nabla x$, for example, as follows:

$$\underset{\nabla x}{\operatorname{argmin}} \|y_t - (Ax_{t-1} + A\nabla x_t)\|_2^2 + \|\Psi \nabla x_t\|_1 \qquad (2)$$

$$\underset{\nabla x}{\operatorname{argmin}} \|(y_t - Ax_{t-1}) - A\nabla x_t\|_2^2 + \|\Psi \nabla x_t\|_1$$

$$\underset{\nabla x}{\operatorname{argmin}} \|\nabla y_t - A\nabla x_t\|_2^2 + \|\Psi \nabla x_t\|_1$$

This objective function can have the same form as Eq. (1). Thus, it can be solved using a similar, or an identical, solver. Speckle noise can be a source of corruption in OCT-generated images, degrading image quality and potentially hindering accurate CS reconstruction. As a result, it can improve reconstruction performance to incorporate de-noising into the objective function. For example, rather than using $\ell^1$ regularization on the difference image $\nabla x$, it can be used on the de-noised version through some de-noising function $D(x, \lambda)$ where $\lambda$ can be a denoising parameter. In this exemplary case, the objective function can become, for example, the following:

$$\underset{\nabla x}{\operatorname{argmin}} \|\nabla y_t - A\nabla x_t\|_2^2 + \|\Psi D(\nabla x_t, \lambda)\|_1 \qquad (3)$$

In this exemplary objective function, $\nabla x_t$ can be in the $\ell^2$ term and $D(\nabla x_t)\ell^1$ term so it may not be possible to solve using the same approach that can be employed to solve Eq. (2). Instead, an alternative procedure can be utilized for denoising image restoration (see, e.g., Reference 28), which can be used to solve Eq. (3) by decoupling the objective function into two subproblems. The subproblems of Eq. (3) can be defined, for example, as follows:

$$\nabla \hat{x}_i = \underset{\nabla x}{\operatorname{argmin}} \|\nabla y - A\nabla x\|_2^2 + \alpha \|\nabla x - \nabla x_{i-1}\|_1 \qquad (4)$$

$$\nabla x_i = \underset{\nabla x_i}{\operatorname{argmin}} \|D(\nabla x, \lambda) - \nabla \hat{x}_i\|_2^2 + \beta \|\Psi D(\nabla x, \lambda)\|_1 \qquad (5)$$

The iteration can initiate with an initial guess $\nabla x_{i-1}$ and can be penalized to agree with the observation y. The second equation can control the sparsity of the solution via the $\ell^1$ norm. Noting that the OCT image can be sparse when denoised and transformed to the Fourier basis, $\Psi D(\nabla x)$ can be penalized rather than $\nabla x$ itself. The change of basis can be beneficial to ensure incoherence between the representation and measurement domains. (See, e.g., Reference 8). For example, it was determined that using $D(\nabla x)$ as Gaussian filter was beneficial, although other denoising procedures (e.g., BM3D) can be used. (See, e.g., Reference 29). A rectangular filter size of [7×9] pixels was used to provide an appropriate level of denoising while mitigating possible vertical streaking due to a-line subsampling.

The first subproblem can be solved by taking the derivative, setting it equal to zero, and solving for $\nabla x$. Taking the derivative can provided, for example:

$$(A^H A + \alpha I)\nabla \hat{x}_i = A^H \nabla y + \alpha \nabla x_{i-1} \qquad (6)$$

where the A can be a matrix of "spikes" corresponding to the sampled a-lines of a given b-scan. $A^H A + \alpha I$ can be a diagonal matrix. In particular, the matrix $A^H A$ may only be non-zero at the diagonal elements $k \in \mathcal{K}$ that correspond to the sampled entries of $\nabla x$. From this assumption, the solution can be written as, for example:

$$\nabla \hat{x}_i = \begin{cases} \nabla x_{i-1} + \dfrac{1}{\alpha} A^H \nabla y & , \text{if } k \notin \mathcal{K} \\ \dfrac{\nabla x_{i-1} + A^H \nabla y}{1 + \alpha} & , \text{if } k \notin \mathcal{K} \end{cases} \qquad (7)$$

In this formulation, $\alpha$ can be a rough measure of the noise in observation y where $\alpha=0$ can correspond to the noiseless case. In these results $\alpha=0.1$ can be used.

The solution of the second equation can be found by using the proximity operator, which can be in the following exemplary form:

$$\Psi x_i = \operatorname{prox}_{\lambda \|\cdot\|_1}(\Psi D(\nabla \hat{x}_i, \lambda), \beta) \qquad (8)$$

where $\ell^1$ can be solved by performing element-wise soft-thresholding of the argument. The soft-thresholding operation soft( ) of matrix element $u_i$ by threshold $\beta$ can be defined for complex-valued entries as sign $(u_i)$ max $(|u_i|-\beta, 0)$.

This exemplary procedure can be referred to as DN-PC, which is shown in Procedure 1 below. An exemplary feature of the exemplary DN-PC can be the use of an adaptive denoising parameter $\lambda$. In contrast to previous approaches, more of the important image features can be recovered by first denoising strongly, and then iteratively decreasing the degree of denoising. In the exemplary DN-PC, A, can have two values $(\lambda_1, \lambda_2)$ which can represent the vertical and horizontal standard deviation of the 2-D Gaussian Filter D(•, $(\lambda_1, \lambda_2)$). The variability of $\lambda$ can be controlled by setting $\lambda_{max}$ and $\lambda_{min}$ such that $\lambda$ can decrease logarithmically over $\mathcal{T}$ iterations. $\lambda_{max}$ and $\lambda_{min}$ can be set differently for $\lambda_1$ and $\lambda_2$. The structure of the procedure can be to update over an inner and outer iteration. The inner iteration can solve subproblems for a fixed value of $\lambda$ until the update reaches max iteration I or the solution update becomes small (e.g., set using $\tau$), while the outer loop iterates $\mathcal{T}$ times over $\lambda$.

Procedure 1: Denoised Predictive Coding (DN-PC)

Input: $\nabla y_t$, $\alpha$, $\lambda_{max}$, $\lambda_{min}$, $\tau$
Output: $\nabla x_t$
Initialize: $\nabla x_t^0 = A^H \nabla y_t$;

Initialize: $\lambda^0 = \lambda_{max}$, $\delta = \exp\left(\dfrac{\log(\lambda_{max}) - \log(\lambda_{min})}{\mathcal{T} - 1}\right)$;

-continued

Procedure 1: Denoised Predictive Coding (DN-PC)

for j = 1, 2, ... T do
   while (i < I)&(update>U) do $$\nabla \hat{x}_{t,i} = \begin{cases} \nabla x_{t,i-1} + \dfrac{1}{\alpha} A^H \nabla y_t, & \text{if } k \notin \mathcal{K} \\ \dfrac{\nabla x_{t,i-1} + A^H \nabla y_t}{1 + \alpha}, & \text{if } k \notin \mathcal{K} \end{cases};$$

Figure 14:
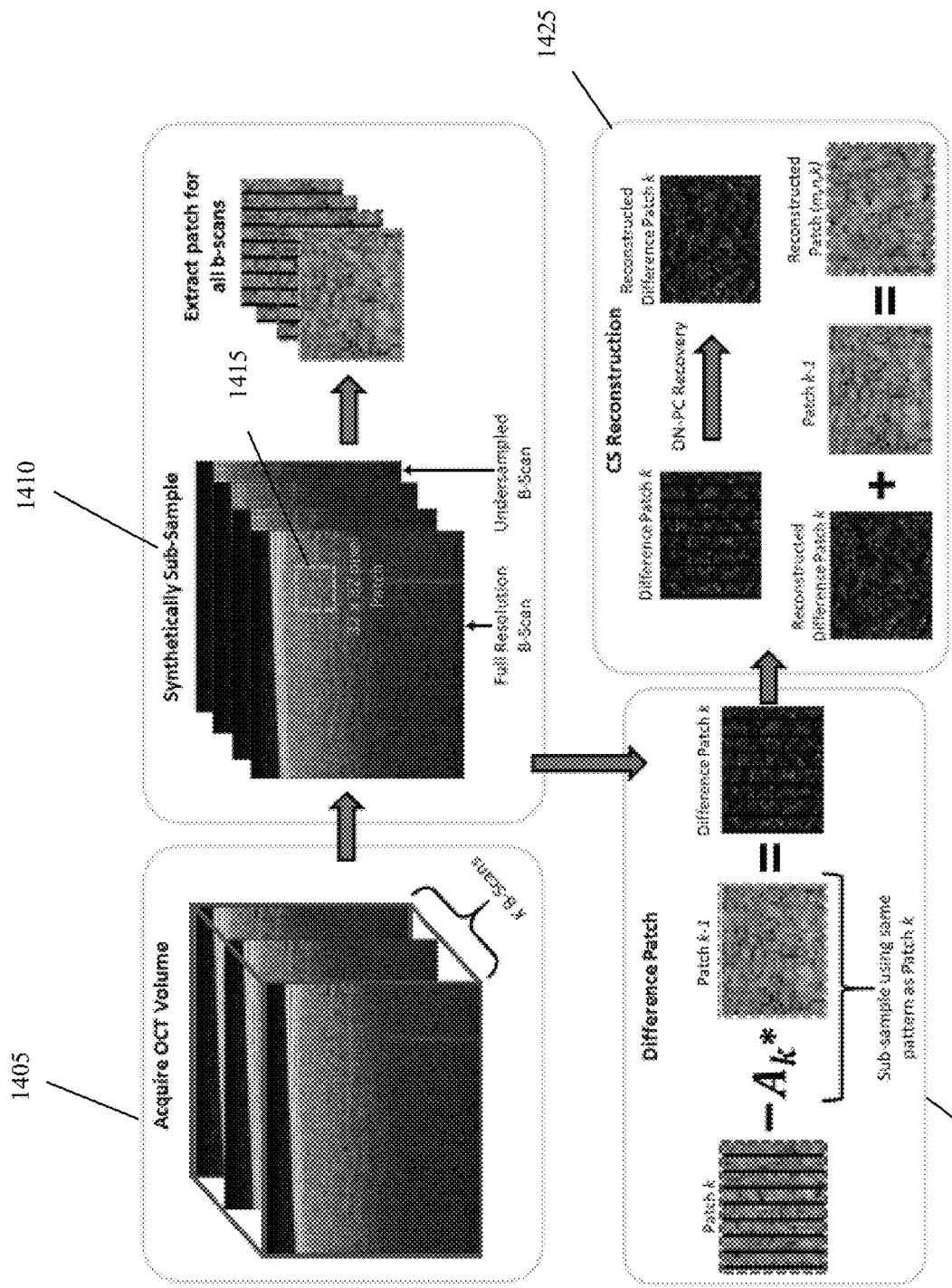
FIG. 14 is an exemplary flow diagram of an image recovery procedure according to an exemplary embodiment of the present disclosure.

$\Psi \nabla x_{t,i} = \text{soft}(\Psi D(\nabla \hat{x}_{t,i}, \lambda_j), \beta)$;
     $\nabla x_{t,i} = \Psi^{-1} \nabla x_{t,i}$;
     update = $\| \nabla x_{t,i} - \nabla x_{t,i-1} \|_2$;
     $U = \tau * (1 + \| \nabla x_{t,i-1} \|_2)$;
   end
   $\lambda^{j+1} = \lambda^j / \delta$;
end Exemplary Compressed Sensing Pipeline FIG. 14 is an exemplary flow diagram of an image recovery procedure according to an exemplary embodiment of the present disclosure. Undersampling of OCT volume 1405 can be simulated by omitting a-lines at a regular interval. Sparsely sampled OCT volume 1410 can be reconstructed by iterating over square pixel patches 1415 of each b-scan. An exemplary patch size can be 32×32 pixels. A given patch (m,n) can be reconstructed over all T b-scans before advancing to the next patch, where m and n are the row and column indices of the patch, respectively. To reconstruct patch (m,n) at b-scan t, the difference image can be acquired by first undersampling then subtracting patch (m,n) at b-scan t-1. Patch t-1 can be undersampled by multiplying it by the sampling matrix A. The exemplary DN-PC can generate a reconstruction of the difference patch 1420 which can then be added to the full resolution patch at (m,n,t-1) to get the reconstructed patch (m,n,t) 1425.

Reconstructing the difference image can benefit from the modifications to the exemplary imaging and reconstruction procedure. One problem can be that the reconstruction accuracy of a given patch can be dependent on that of the patch from the previous b-scan so errors from one can propagate through the entire volume. An exemplary unique sampling procedure can be used to mitigate this problem by using staggered sampling and periodic full-resolution acquisitions. A graphical depiction of the sampling strategy is shown in FIG. 15, which illustrates an exemplary diagram illustrating a-line sampling and sampling using a-line staggering and period full-resolution b-scan acquisitions according to an exemplary embodiment of the present disclosure.

Figure 15:
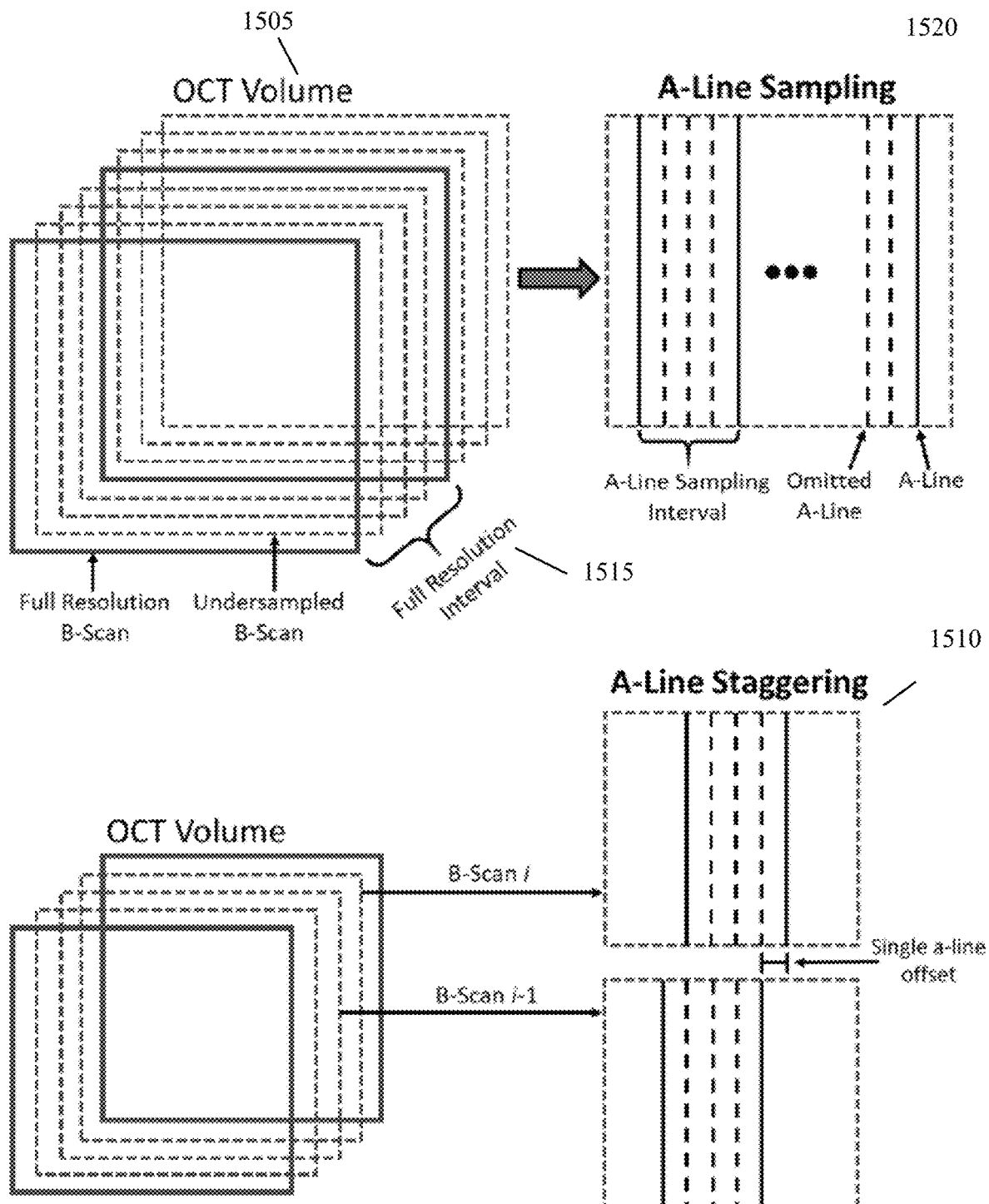
FIG. 15 is an exemplary diagram illustrating sampling using a-line staggering and period full-resolution b-scan acquisitions according to an exemplary embodiment of the present disclosure.

The diagram shown in FIG. 15 can facilitate denoising+predictive coding CS for OCT volumetric or time-lapsed datasets 1505. Sampling can be performed using A-line staggering and period full-resolution b-scan acquisitions. A challenge in reconstructing the difference image can be that the reconstruction accuracy can be dependent on the patch from the previous b-scan because errors from each b-scan can propagate through the entire volume. The exemplary system, method, and computer-accessible medium, according to an exemplary embodiment of the present disclosure, can be used to mitigate this problem by using staggered sampling and 1510 and periodic full-resolution acquisitions 1515. Staggered sampling includes shifted the sampling pattern by one a-line between adjacent b-scans so that the same a-lines are not omitted for the entire volume. Full-resolution b-scans can be acquired periodically to "reset" any error that still results from propagation.

Exemplary Sampling

Herein, "compression rate" $\eta_a$ can refer to the number of a-lines sampled in each image patch, (e.g., a 25% compression rate means that one in every four a-lines were acquired). The compression rate of a b-scan $\eta_b$ in units of pixels can be calculated, for example, as follows:

$$\eta_b = \frac{\text{floor}(\eta_{a^*} \sqrt{N_{patch}}) * \sqrt{N_{patch}}}{N_{patch}} \qquad (9)$$

where the operator floor( ) can round the argument down to the nearest integer value, and $N_{patch}$ can be the total number of pixels per image patch. Compression can be defined for volumes, which can take into account the periodically acquired full-resolution b-scans. This can be the true compression rate $\eta$ which can be a function of the full-resolution b-scan interval $I_b$. If a full-resolution b-scan can be acquired every ten b-scans in the volume, then $I_b$=10. The true compression rate $\eta$ can be calculated, for example, as follows:

$$\eta = \frac{(N_b * (T / I_b)) + (\eta_b * N_b * (T - T / I_b))}{N_{vol}} \qquad (10)$$

where $N_b$ can be the number of pixels per a full-resolution b-scan, $N_{vol}$ can be the number of pixels per a full-resolution volume, and T can be the number of b-scans in the volume.

Exemplary Experimental Methods

Successful reconstruction using the DN-PC method can be based on the assumption that sparsity can be improved over the raw image by taking the difference with an adjacent image in the OCT volume and applying mild denoising. This assumption can be first verified by examining pixel decay plots of an image compared with its difference image and a noise-only image.

The exemplary DN-procedure was evaluated on OCT volumetric datasets of five different tissue samples, which were acquired at full-resolution and then synthetically sub-sampled. Sampling strategies were evaluated by testing reconstruction accuracy at multiple a-line sampling rates and comparing staggered with uniform a-line sampling. Next, DN-PC performance was evaluated by reconstructing an OCT volume from each of the five tissue samples. The results were quantitatively evaluated and representative images were selected for visual comparison.

The performance of the exemplary DN-PC procedure was compared with two other procedures. Patch-based reconstruction of the raw OCT b-scan, iterating over all b-scans in the volume. The employed procedure, called YALL1, can be an optimized procedure for $\ell^1$ minimization (see, e.g., Reference 30), and can be used to solve Eq. (1). This exemplary procedure can be used to reconstruct an OCT volume by iterating the reconstruction over 32×32 pixel patches and each b-scan. The second method can also utilize a Predictive Coding approach, but with the exemplary implementation of TVL1 reconstruction based on RecPF. (See, e.g., Reference 31). This exemplary procedure can utilize a Total-Variation ("TV") regularization term, which can promote smoothness while also preserving edges, and can be used for CS-MRI. The exemplary implementation according to exemplary embodiment(s) of the present disclosure described herein can facilitate the exemplary system, method, and computer-accessible medium to be used on OCT volumes and in the Predictive Coding framework, which can be referred to as TVL1-PC. All three procedures were tested and implemented in MATLAB 2020a using a Windows 10 desktop with an Intel® Core™ i9-9900K CPU at 3.6 GHz and 128 GB of RAM.

Exemplary Parameters

Various exemplary procedures described herein were tested using reconstruction parameters which can effect end performance. These parameters were empirically determined empirically, the same ones were utilized in all tests unless otherwise specified. For DN-PC, $\alpha=0.1$, $\beta=1$, $\lambda_{max}=$ [3, 4], $\lambda_{min}=[0.2, 0.4]$, $\mathcal{T}=20$, I=20, and convergence threshold was $\tau=10^{-3}$. A filter size of 7×9 for the Gaussian denoising filter was used, which can be rectangular to smooth vertically streaking that can appear as a result of a-line sub sampling. For YALL1, the Discrete Cosine Transform ("DCT") was chosen as the sparsifying basis. The convergence tolerance was $5*10^{-4}$ and parameter $\rho=5*10^{-4}$. While staggered a-line sampling and periodic full-resolution may not be necessary to use with YALL1, they can be both employed in all cases for accurate comparison. For TVL1-PC, a level-3 Haar wavelet was used as the sparsifying basis, the anisotropic TV measure, and parameters $\mu=10^4$, $\beta=20$, $\tau=0.5$, and $\gamma=(\sqrt{5}+1)/8$.

Exemplary Datasets

For example, five different exemplary datasets were used. Each dataset contained OCT volumes of a different, structurally complex, tissue samples, which included: (i) human right atria (see, e.g., References 4 and 32), (ii) human uterus (see, e.g., Reference 5), (iii) human retina (see, e.g., Reference 33), (iv) bovine Anterior Cruciate Ligament ("ACL") (see, e.g., References 34 and 35), and (v) human breast. (See, e.g., Reference 36). The human retina data is a publicly available dataset. (See, e.g., Reference 33). The heart, uterus, ACL, and breast datasets were collected internally using a commercial TELESTO SD-OCT system (e.g., Thorlabs, GmbH, Germany) with 6.5 μm axial and 15 μm lateral resolution. All OCT volumes were cropped to a size of 512×800×800 pixels for consistent comparison with the exception of the retina volumes which have only 100 b-scans. Prior to reconstruction, all datasets can be converted double precision and pixel intensity can be scaled to a range of [0, 1].

Exemplary Metrics

Several quantitative metrics were used to assess and compare CS reconstruction performance. The first was Relative Error which measures the intensity differences between the true and reconstructed volumes. It can be defined as, for example:

$$\text{Relative Error} = \frac{\|x_{recon} - x\|_2}{\|x\|_2} \quad (11)$$

where x can be the vectorized original OCT volume and $x_{recon}$ can be the reconstructed version. When evaluating the relative error for images, the Frobenious norm can be used instead. The other metric used was the Structural Similarity Index ("SSIM") which uses luminance, contrast, and structure to evaluate the similarity between two images. (See, e.g., Reference 37). The SSIM of two images can be a value between 0 and 1 where an SSIM of 1 can indicate that the two images can be identical. Where SSIM can be reported for a volume, the average SSIM over all b-scans in the volume was provided. Because image volumes can be reconstructed, the 3-D Multi-Scale SSIM ("MULTI-SSIM 3D") was also measured. (See, e.g., Reference 38). This can be a variant of the SSIM metric for image volumes that can apply the same procedure at multiple scales and produces an aggregate score.

While measuring exact reconstruction error can be important, an analysis of the ability to reconstruct important tissue features independently from speckle noise and other noise sources can be beneficial. 2-D median filtering can be a popular and light-weight choice for OCT image denoising. Consequently, a [3×3] pixel median filter was applied to the reconstructed volumes before measuring relative error and SSIM to obtain a more honest assessment of the procedure's ability to reconstruct important tissue structures. Denoised metrics can be reported using the identifier ("DN"). (See Table 5 below).

Exemplary Results

Figure 16G:
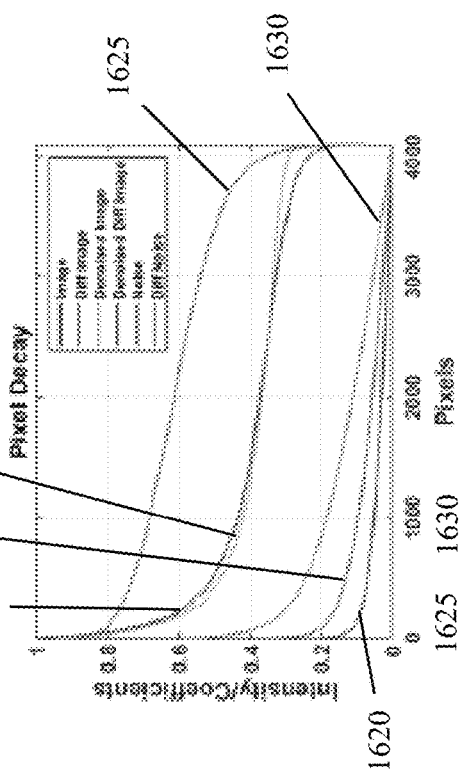
FIG. 16G is an exemplary graph illustrating pixel decay for images 16A-16F according to an exemplary embodiment of the present disclosure.
Figure 16H:
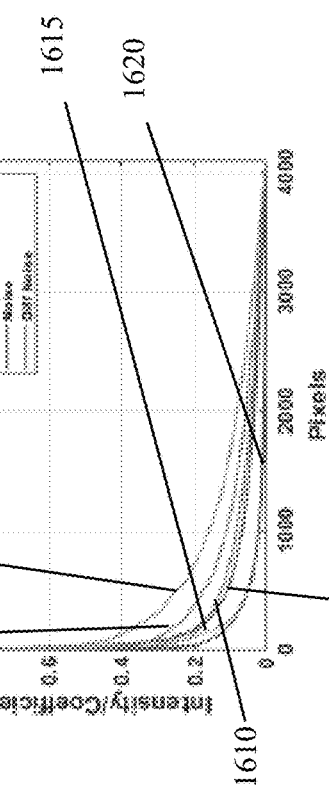
FIG. 16H is an exemplary graph illustrating pixel decay plots for the discrete cosine transformed DCT images of FIGS. 16A-16F according to an exemplary embodiment of the present disclosure.
Figure 16B:
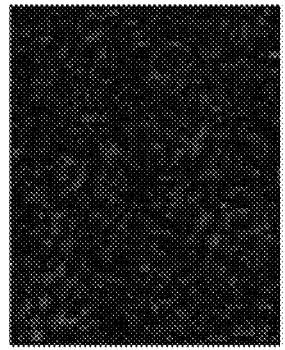
FIG. 16B is an exemplary raw difference image according to an exemplary embodiment of the present disclosure.
Figure 16D:
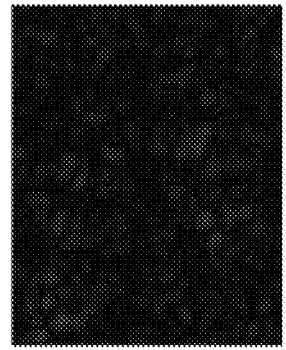
FIG. 16D denoised difference image according to an exemplary embodiment of the present disclosure.
Figure 16F:
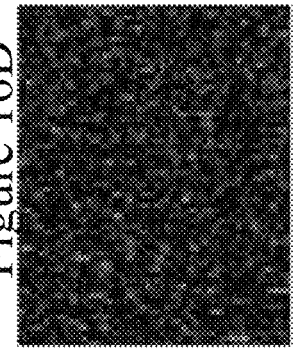
FIG. 16F is an exemplary noisy difference image according to an exemplary embodiment of the present disclosure.
Figure 16A:
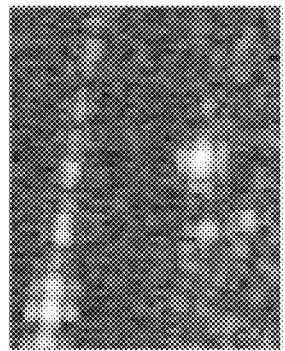
FIG. 16A is an exemplary raw OCT image patch according to an exemplary embodiment of the present disclosure.
Figure 16C:
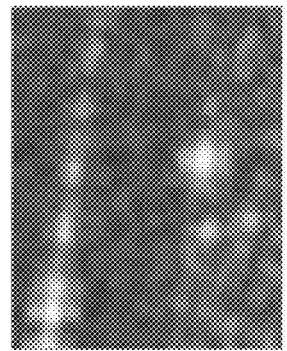
FIG. 16C is an exemplary denoised image according to an exemplary embodiment of the present disclosure.
Figure 16E:
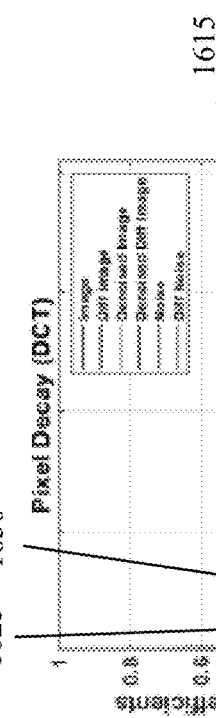
FIG. 16E is an exemplary speckle noise PCT image patch according to an exemplary embodiment of the present disclosure.

FIGS. 16A-16F show exemplary image patches from an OCT volume of a glass slide and their corresponding pixel decay plots. The pixel decay plots (e.g., shown in FIGS. 16G and 16H) were generated by vectorizing the image patch and sorting the pixels in descending order of intensity. Plots which decay to zero more quickly correspond to a sparser image. FIGS. 16A, 16C, and 16E are image patches while FIGS. 16B, 16D, and 16F are the corresponding difference images. FIG. 16A shown a patch of the cover slip, the same cover slip when denoised (e.g., FIG. 16C), and a patch of noise only (e.g., FIG. 16E). FIGS. 16G and 16H show the pixel decay plots for the six image patches in the image domain and Discrete Cosine domain, respectively (e.g., Image 1605, Diff Image 1610, Denoised image 1615, Denoised Diff image 1620, noise image 1625, and diff noise image 1630). The exemplary images shown in FIGS. 16A-16F illustrate that the difference operation can preserves noise, but denoising prior to taking the difference (see, e.g., FIGS. 16C and 16D) can isolate the structural differences of interest between adjacent b-scans. In the image domain, the noise patch can be the least sparse while the denoised difference image can be the most sparse. In all cases, the difference operation and denoising created sparser image patches than their counterparts.

Figures 17A, 17B:
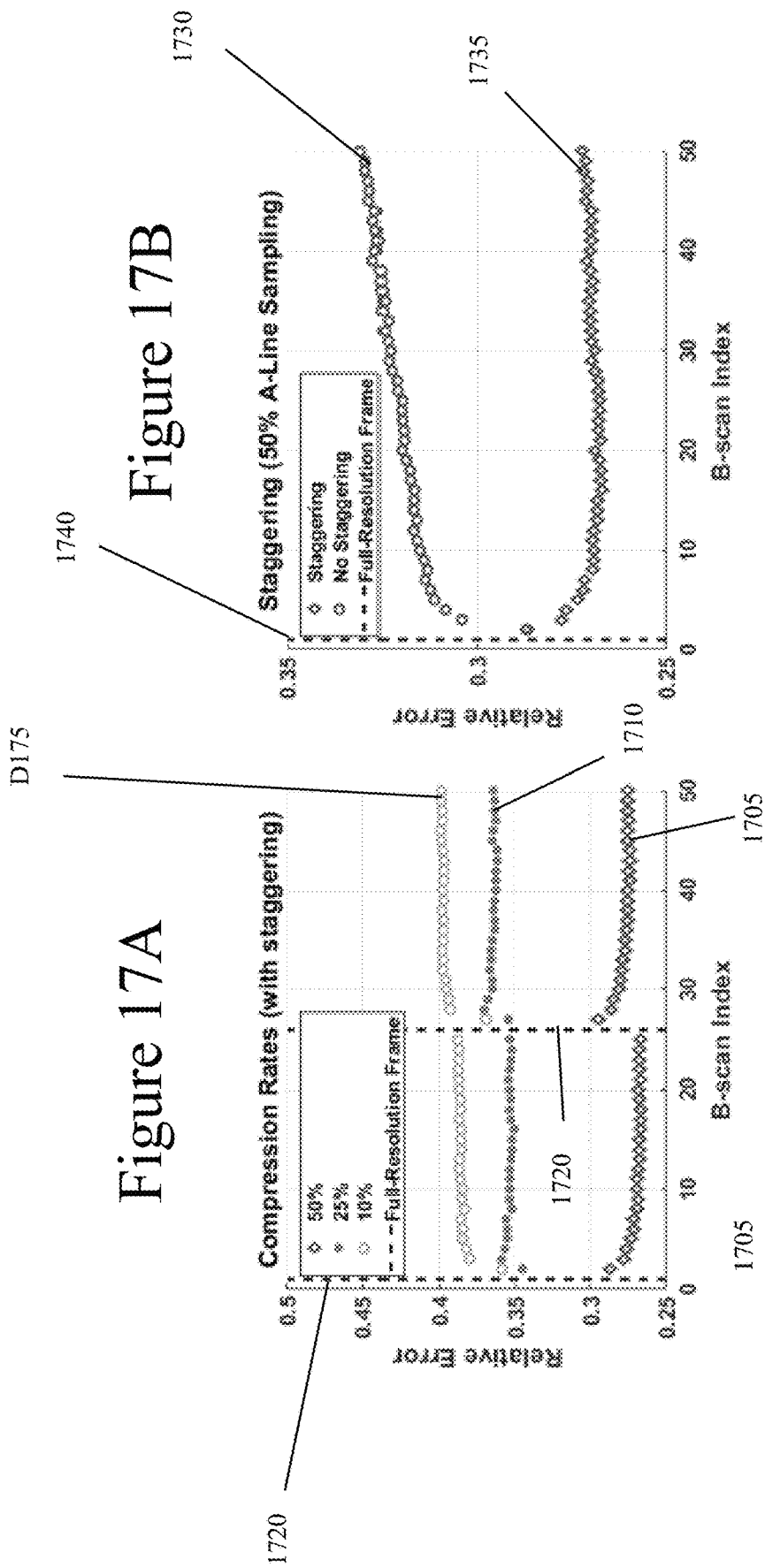
FIG. 17A is an exemplary graph illustrating relative reconstruction error for 50 b-scans at 3 a-line sampling rates using the exemplary system, method, and computer-accessible medium according to an exemplary embodiment of the present disclosure.
FIG. 17B is an exemplary graph illustrating relative reconstruction error with and without a-line staggering at 50% sampling with a 50 b-scan full-resolution interval according to an exemplary embodiment of the present disclosure.

The effects of different sampling parameters on reconstruction performance were tested to determine an optimal reconstruction configuration. FIGS. 17A and 17B show the relative error from reconstructing a 50 b-scan subset of an OCT heart volume. As shown in FIG. 17A, three different a-line sampling rates $\eta_a=50\%$ (e.g., shown by element 1705), 25% (e.g., shown by element 1710), and 10% (e.g., shown by element 1715) were tested using a full-resolution interval $I_b=25$ b-scans (e.g., dotted line 1720) and a-line staggering (e.g., Dotted line 1725). The staggering suppresses error as a function of distance from the last full-resolution b-scan, though a small linear increase in the error can be visible with 10% sampling. FIG. 17B demonstrates the effect of staggered sampling by comparing the relative error of the same reconstructed volume using $\eta_a=50\%$ but with and without staggering. In the "no staggering" case, the same a-lines can be omitted every b-scan. In both cases, the b-scan at index 1 can be fully sampled. As shown in FIG. 17B, without staggering (e.g., shown by element 1730), the error increases linearly from 0.3 to 0.33 over 50 b-scans. With staggering (e.g., shown by element 1735), the error dips initially and then plateaus to a value around 0.27. Not only did staggering lower the average error, but it also suppressed the rate of error as a function of distance from the last full-resolution b-scan (e.g., shown by dotted line 1740).

The exemplary effects of staggering shown in FIGS. 17A and 17B were quantitatively verified for a full OCT volume from the human cardiac dataset and reported in Table 4 below. Eight use-cases were tested with staggering on and off, using two a-line sampling rates $\eta_a$=50%, 25%, and using two full-resolution intervals $I_b$=10, 50. The OCT volume dimensions were 512×800×800 pixels and a patch size of 32×32 pixels was used. The "Full-Res B-Scans" column of the table shows the total number of full-resolution b-scans obtained for the two intervals. Similarly, the column "Sampled A-Lines/B-Scan" shows that 25% and 50% sampling resulted in acquisitions of 200 and 400 a-lines per b-scan, respectively. The true compression rate $\eta$ includes the full-resolution b-scans so it can be higher than the a-line sampling rate $\eta_a$ (see Eq. (10)), though the margin of increase can be larger for smaller sampling rates. In all cases, staggering improved the relative reconstruction error. The full-resolution interval trades off between relative error and $\eta$. For example, in the case of $\eta_a$=25% with staggering on, the relative error improved from 0.2810 to 0.2742 when $I_b$ is lowered from 50 to 10, but at the expense of raising $\eta$ from 26.5% to 32.5%.

TABLE 4

Quantitative summary of the effects of a-line sampling $\eta_a$, staggering, and the full-resolution interval $I_b$ on compression and relative error.

Staggering and Full-Resolution Interval Test

| A-Line Sampling $\eta_a$ (%) | Staggering | Full-Res. Interval $I_b$ | Full-Res. B-Scans | Sampled A-Lines/ B-Scan | Compression Rate $\eta$ (%) | Relative Error |
|---|---|---|---|---|---|---|
| 25 | On | 10 | 80 | 200 | 32.5 | 0.2742 |
|  |  | 50 | 16 | 200 | 26.5 | 0.2810 |
|  | Off | 10 | 80 | 200 | 32.5 | 0.2961 |
|  |  | 50 | 16 | 200 | 26.5 | 0.3172 |
| 50 | On | 10 | 80 | 400 | 55 | 0.2130 |
|  |  | 50 | 16 | 400 | 51 | 0.2146 |
|  | Off | 10 | 80 | 400 | 55 | 0.2395 |
|  |  | 50 | 16 | 400 | 51 | 0.2541 |

Exemplary Multiple Tissue Type Test

Figure 18:
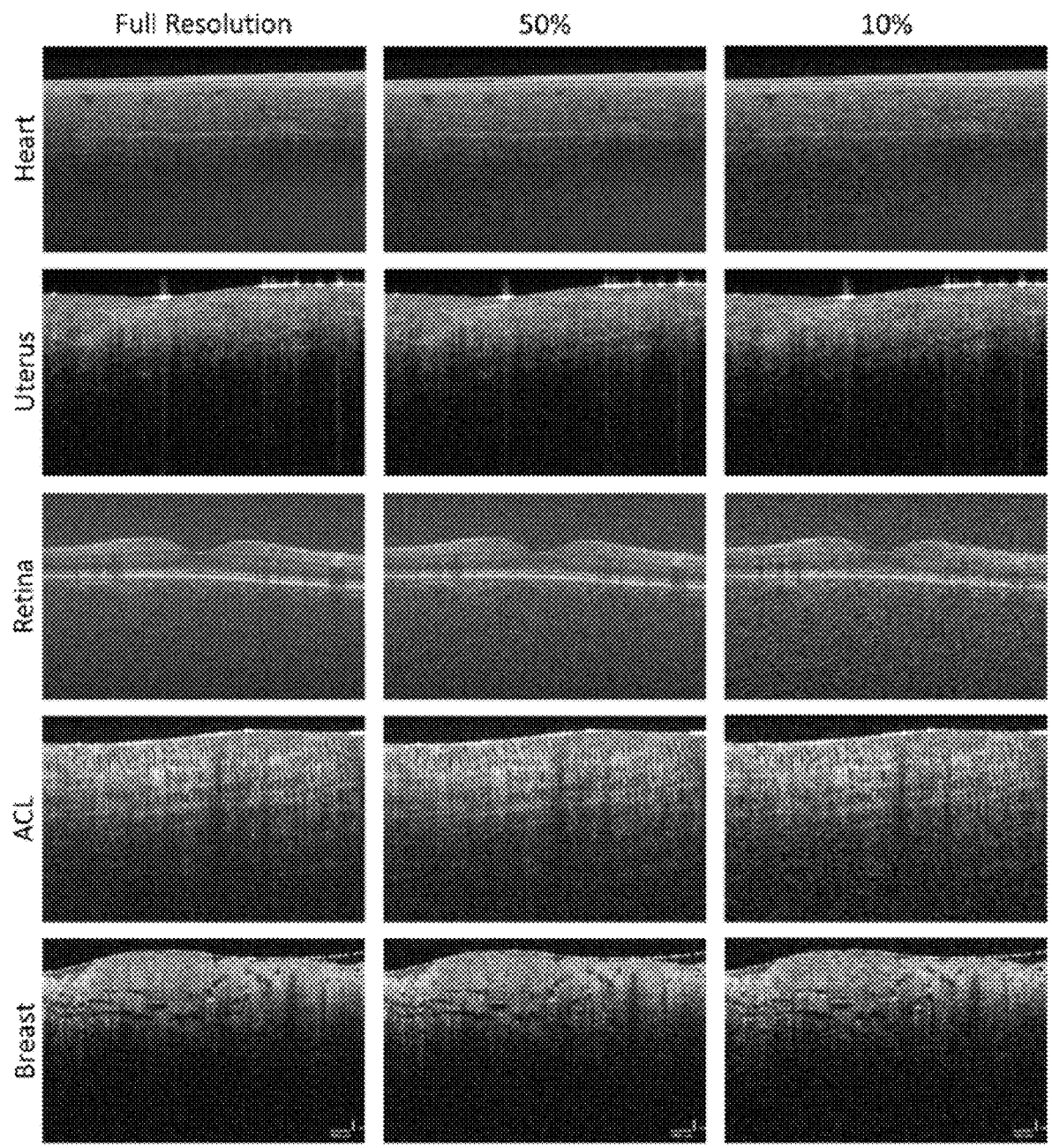
FIG. 18 is a set of images of B-scans according to an exemplary embodiment of the present disclosure.
Figure 19:
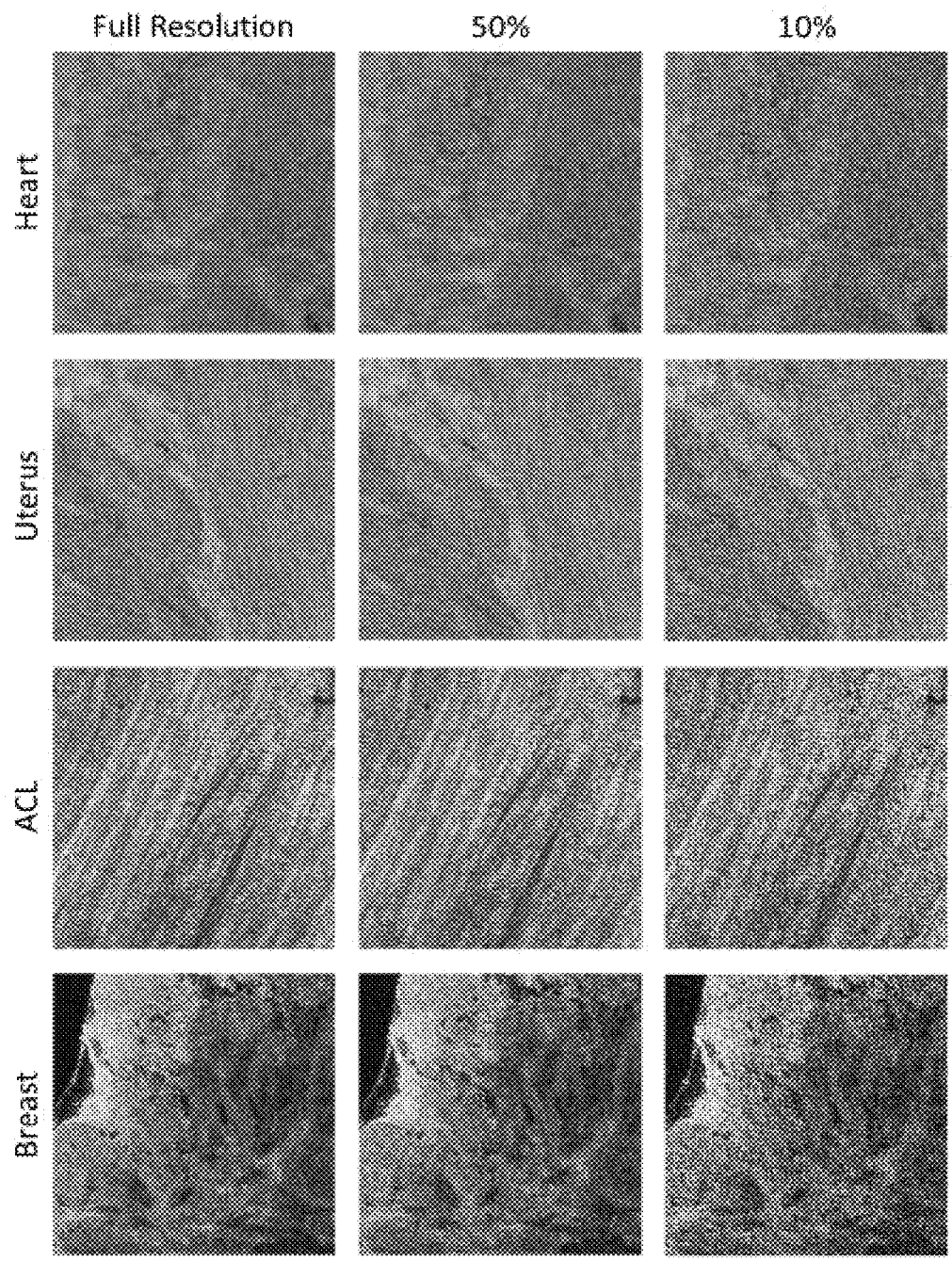
FIG. 19 is a set of exemplary en-face images produced using the exemplary system, method, and computer-accessible medium according to an exemplary embodiment of the present disclosure.

The exemplary DN-PC was used to reconstruct OCT volumes from five different tissue samples: (i) human heart, (ii) human uterus, (iii) human retina, (iv) bovine ACL, and (v) human breast tissue. Exemplary b-scans from each of the reconstructed volumes are shown in FIG. 18. The different tissue types are organized by row and the different sampling rates are organized by column. The different samples and images were chosen to showcase a variety of tissue structures, image textures, and noise environments. Qualitatively, the examples with 50% sampling can be nearly indistinguishable from the corresponding full-resolution b-scans, while the 10% samples appear noisier and fine features can be blurred. Exemplary en-face images from the same volumes are shown in FIG. 19. Similar degradation of image quality can be observed for 10% a-line sampling compared with 50%. Unlike in the b-scan images, horizontal streaking can be visible in the en-face images along the fast-scan axis, which can be artifacts from errors in reconstruction. The retina volumetric scans include only 100 b-scans so en-face images from those samples were omitted as they do not provide valuable information even in the full-resolution volume.

Reconstructed volumes from the uterus and ACL datasets were rendered in 3D to compare volumetric features with the full-resolution volumes. Figure GG shows images from the uterus volume rendering in the first row and the ACL volume in the second row. Sampling rates are organized by column. Collagen fibers were labelled and identified in the full-resolution volumes (e.g., first column) which can be visible in the reconstructions at both 50% and 25% a-line sampling. The 3D perspective shows how the exemplary DN-PC reconstructed volumes can preserve volumetric features visible in both the en-face and axial image planes.

The exemplary DN-PC volumetric reconstruction performance for 5 different tissue types was quantitatively measured and s in Table 5 which shows the relative error and average SSIM of each reconstruction. A representative OCT volume from each of the 5 tissue types was reconstructed at three a-line sampling rates $\eta_a$=50%, 25%, and 10% using staggering and $I_b$=10. Relative error and SSIM is reported with and without denoising (e.g., labelled DN) following reconstruction. The denoised results are improved over the raw data results across all test cases which indicates strong preservation of tissue structures. The exemplary DN-PC achieved the best performance for the cardiac volume, while the retina and breast volumes proved the most challenging.

Figure 20:
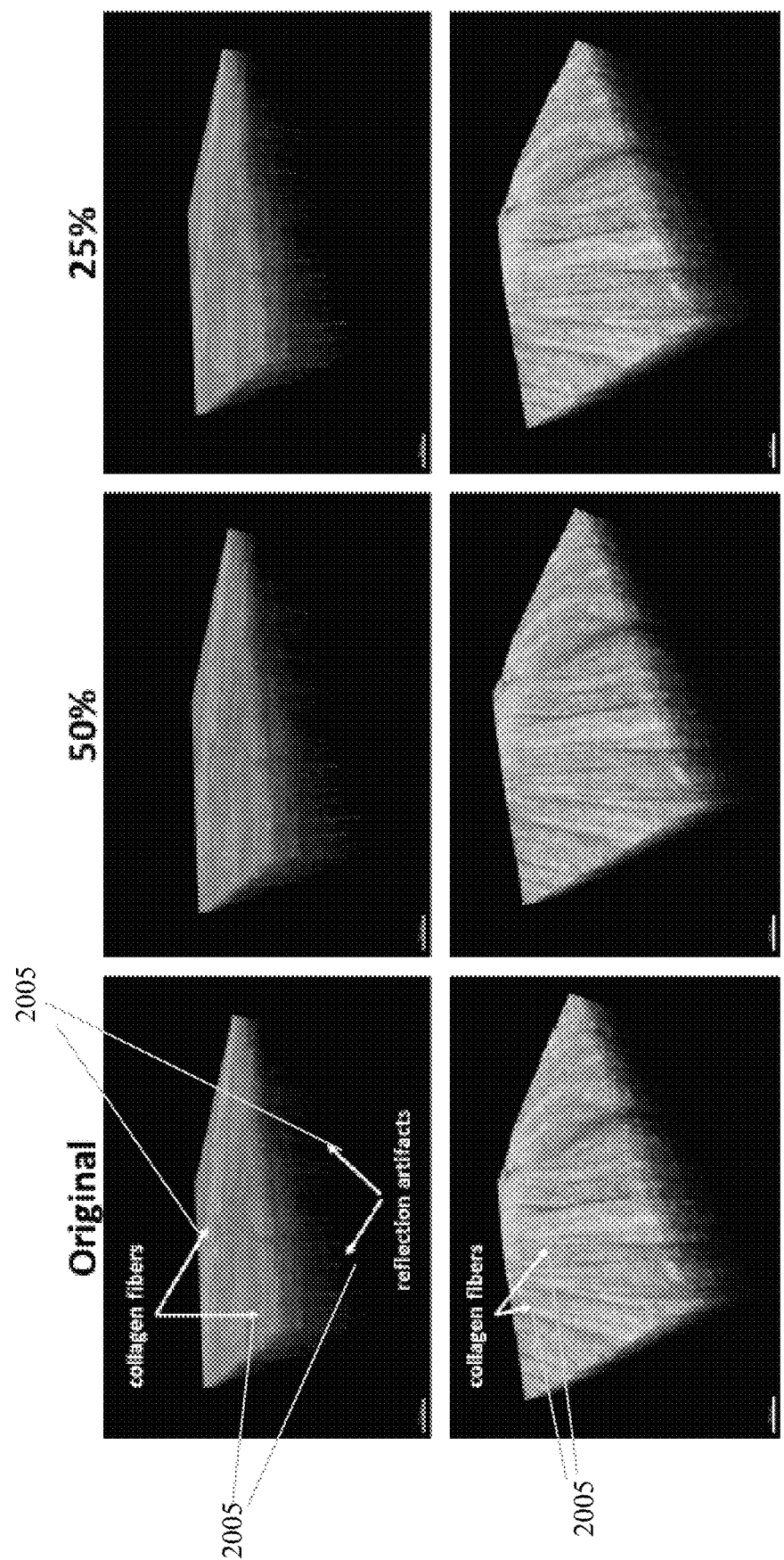
FIG. 20 is a set of exemplary 3-D reconstructions according to an exemplary embodiment of the present disclosure.
Figure 21:
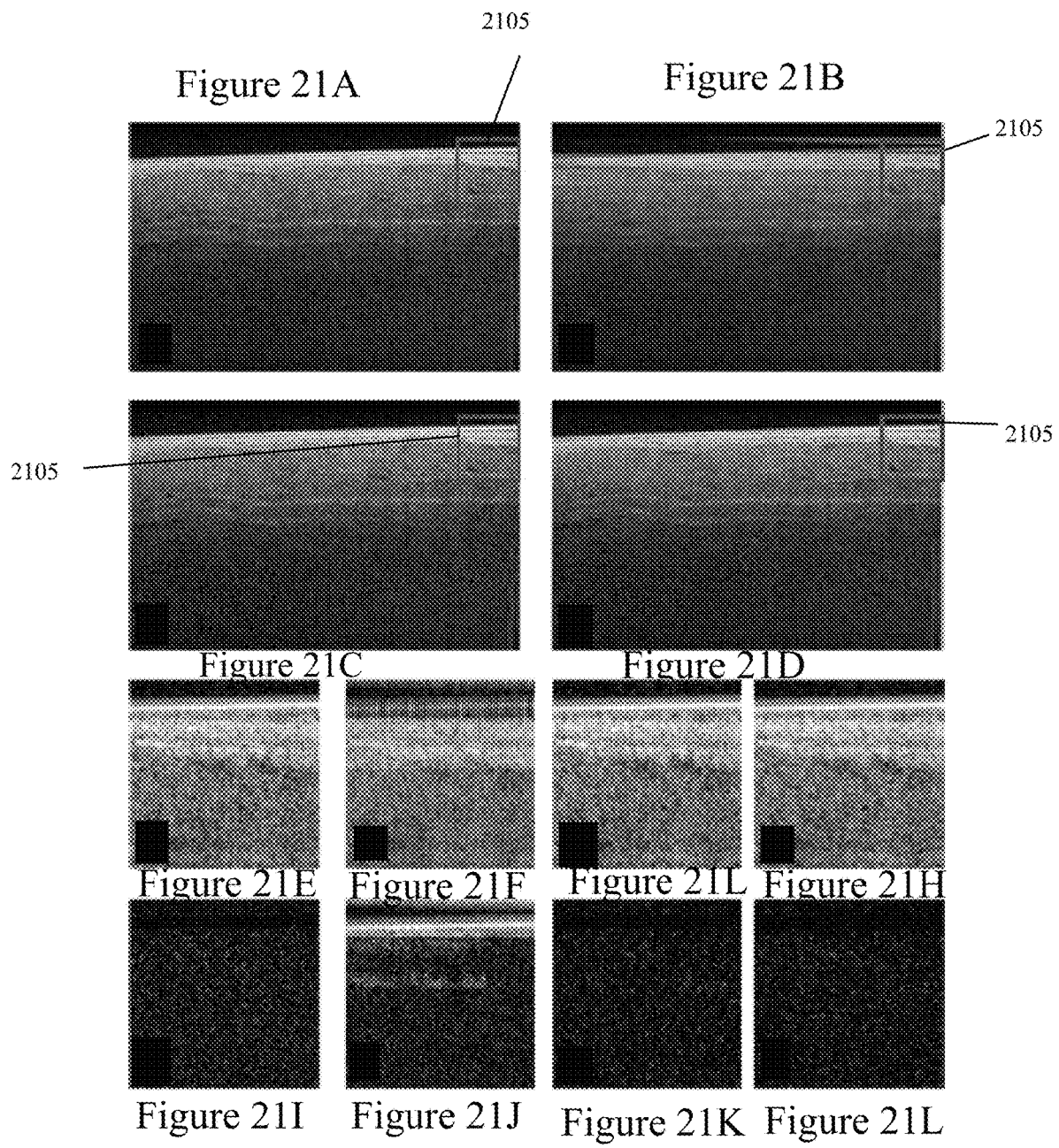
FIG. 21A is an exemplary non-reconstructed image according to an exemplary embodiment of the present disclosure.
FIG. 21B is an exemplary image reconstructed using the exemplary YALL1 reconstruction according to an exemplary embodiment of the present disclosure.
FIG. 21C is an exemplary image reconstructed using the exemplary TVL1-PC reconstruction according to an exemplary embodiment of the present disclosure.
FIG. 21D is an exemplary image reconstructed using the exemplary DN-PC reconstruction according to an exemplary embodiment of the present disclosure.
FIGS. 21E, 21F, 21G, and 21H are exemplary images of the insets from FIGS. 21A, 21B, 21C, and 21D, respectively, according to an exemplary embodiment of the present disclosure.
FIGS. 21I, 21J, 21K, and 21L are exemplary difference images from the insets from FIGS. 21A, 21B, 21C, and 21D, respectively, according to an exemplary embodiment of the present disclosure.

FIG. 20 shows a set of exemplary 3-D reconstructions according to an exemplary embodiment of the present disclosure. OCT volumes of a human uterus are illustrated in the first row, and bovine ACL is shown in the second row of FIG. 20. For example, both tissues were reconstructed using the DN-PC procedure. The first column is the full sampled volume, the second column was reconstructed with 50% a-line sampling, and the third column was reconstructed with 10% a-line sampling. Arrows 2005 point to tissue structures and artifacts of interest.

Exemplary Testing the Procedure

The exemplary DN-PC performance was compared with two other CS reconstruction methods, YALL1 and TV-L1 PC using 100 b-scan sub-volumes of all five tissue samples at $\eta_a$=50%. Staggering and $I_b$=10 were used in all cases for accurate comparison. In each case, relative error, average SSIM, MULTI-SSIM 3D, and computation time were recorded. Quantitative results are reported in Table 6.

FIGS. 21A-21L show exemplary b-scans from the heart dataset at full-resolution and reconstructed using each procedure at 50% A-line sampling. Images shown in FIGS. 21A, 21B, 21C, and 21D illustrate the full-resolution b-scan, YALL1 reconstruction, TVL1-PC reconstruction, and DN-PC reconstruction, respectively. Insets of a magnified portion of the full-resolution myocardial tissue surface are shown for each procedure in FIGS. 21E-21H, where the inset is marked by the rectangles 2105. Difference images at the same inset location are shown in FIGS. 21I-21L. The insets indicate that YALL1 can be susceptible to streaking artifacts from the a-line sampling. The TVL1-PC reconstruction can be of similar quality to the original image, however, the difference image reveals it can also be susceptible to streaking. The exemplary DN-PC procedure does not reconstruct the original image as precisely as TVL1-PC, but the difference image reveals that DN-PC can be more focused on reconstructing structural difference between frames rather than an exact noise pattern.

Comparing with the quantitative results in Table 6, it can be seen that the exemplary DN-PC can have similar relative error and worse SSIM score then TVL1-PC, yet it takes considerably less time to reconstruct. In the case of the heart sample, the 100 b-scan volume was reconstructed in 19.12 minutes with DN-PC and 616.46 minutes (e.g., over 10 hours) with TVL1-PC. Average SSIM tended to have a large discrepancy between the TVL1-PC and DN-PC results despite qualitatively appearing very similar. The MULTI-SSIM 3D metric gave much better scores for all the reconstructions and reflected the qualitative similarity between TVL1-PC and DN-PC reconstructions as observed in FIGS. 21A-21L.

TABLE 5

Quantitative summary relative error using DN-PC for 5 different tissue sample types at A-line sampling rates of 50%, 25%, and 10%.
DN-PC 3-D Reconstruction Results

| Sample Type | Sampling Rate $\eta_a$ (%) | Rel. Error | Rel. Error (DN) | Average SSIM | Average SSIM(DN) |
|---|---|---|---|---|---|
| Heart | 50 | 0.2130 | 0.1002 | 0.5397 | 0.7331 |
| | 25 | 0.2742 | 0.1377 | 0.3988 | 0.6068 |
| | 10 | 0.2961 | 0.1597 | 0.3507 | 0.5403 |
| Retina | 50 | 0.3818 | 0.1669 | 0.4465 | 0.5806 |
| | 25 | 0.4867 | 0.2237 | 0.2512 | 0.4017 |
| | 10 | 0.5163 | 0.2532 | 0.1808 | 0.3082 |
| Uterus | 50 | 0.2674 | 0.1439 | 0.5492 | 0.6876 |
| | 25 | 0.3570 | 0.2042 | 0.3502 | 0.5133 |
| | 10 | 0.4024 | 0.2548 | 0.2712 | 0.3969 |
| ACL | 50 | 0.2691 | 0.1456 | 0.5409 | 0.6845 |
| | 25 | 0.3626 | 0.2144 | 0.3223 | 0.4839 |
| | 10 | 0.4157 | 0.2768 | 0.2316 | 0.3503 |
| Breast | 50 | 0.3510 | 0.1836 | 0.4644 | 0.5945 |
| | 25 | 0.4615 | 0.2530 | 0.2761 | 0.4259 |
| | 10 | 0.5058 | 0.3027 | 0.2071 | 0.3232 |

Exemplary Discussion

It was determined that, e.g., the majority of CS-OCT studies used a single sample like a glass cover slip or onion cell that is not representative of the structures present in complex human or animal biology. The few CS-OCT studies that use human tissue are either of skin or the retina. (See, e.g., References 21 and 22). CS-OCT was evaluated using five different, clinically relevant tissue types, and the results of different procedural approaches were compared. When comparing quantitative results for each of these cases, it was found that tissue type did not affect reconstruction performance to the same degree as other parameters like sampling rate. However, two sample types, retina and breast, were more challenging to reconstruct than the others. It is likely that the retina dataset had higher reconstruction error because it was acquired using a different OCT system than the other four datasets. The noise variance was higher for the retina dataset, suggesting that denoising parameters like $\lambda_{max}$, $\lambda_{min}$ can be adjusted for image volumes collected with different OCT systems. The source of error in the breast sample can be less clear, but one explanation can be that adipose tissue can be a difficult feature to reconstruct. Adipose appears as small bubbles in OCT b-scans and because DN-PC excels at preserving the overall tissue structure it can be difficult when the tissue can be composed of mostly small, fine features. This problem could be mitigated by adjusting the denoising parameters to prevent potential blurring of the adipose edges.

TABLE 6

Reconstruction procedure comparison test.
Procedure Comparison Test

| Sample Type | Metric | Procedure | | |
|---|---|---|---|---|
| | | YALL1 | TVL1-PC | DN-PC |
| Heart | Rel. Error | 0.3518 | 0.2568 | 0.2768 |
| | SSIM | 0.5511 | 0.5762 | 0.4476 |
| | MULTI-SSIM 3D | 0.8075 | 0.8978 | 0.8806 |
| | Comp Time (min) | 48.79 | 616.46 | 19.12 |
| Retina | Rel. Error | 0.3244 | 0.3515 | 0.3806 |
| | SSIM | 0.5559 | 0.4971 | 0.3852 |
| | MULTI-SSIM 3D | 0.8158 | 0.8583 | 0.8481 |
| | Comp Time (min) | 50.67 | 593.2 | 20.17 |
| Uterus | Rel. Error | 0.3472 | 0.2323 | 0.2566 |
| | SSIM | 0.5403 | 0.6277 | 0.4891 |
| | MULTI-SSIM 3D | 0.8247 | 0.9272 | 0.9078 |
| | Comp Time (min) | 47.23 | 605.74 | 18.74 |
| ACL | Rel. Error | 0.3320 | 0.2343 | 0.2565 |
| | SSIM | 0.5250 | 0.6026 | 0.4876 |
| | MULTI-SSIM 3D | 0.7934 | 0.9096 | 0.8974 |
| | Comp Time (min) | 50.08 | 581.4 | 19.56 |
| Breast | Rel. Error | 0.3795 | 0.3264 | 0.3492 |
| | SSIM | 0.5426 | 0.5310 | 0.4063 |
| | MULTI-SSIM 3D | 0.8238 | 0.8874 | 0.8738 |
| | Comp Time (min) | 50.23 | 585.3 | 20.08 |

Reconstruction performance can be characterized by a relative error, SSIM, MULTI-SSIM 3D, and computation time. Because no gold standard metric exists to assess reconstruction accuracy, these metrics were determined under the assumption that they can be the most common and intuitive measures available. One area of ambiguity with regard to performance analysis can be the reconstruction of noisy images (e.g., which applies to all OCT-generated images). In Table 5, for example, the relative error of both raw reconstructions and reconstructions, was reported, which had been median filtered prior to denoising, and which found that this changed the results significantly. It was beneficial to include both measures because they inherently explain different aspects of the procedure performance. The denoised results measured the ability to reconstruct important tissue structures independently of noise, while the raw reconstruction results measured how closely the reconstruction exactly matches the raw image, which could be equally important in applications like Speckle Variance imaging. (See, e.g., Reference 2).

A challenge in any CS framework can be the formulation of a sampling strategy which works with the imaging hardware and facilitates high accuracy reconstruction of the undersampled data. Recent studies have proposed hardware procedures for undersampling using CCD camera masking materials (see, e.g., Reference 39) and masking spectral data within a DAQ (see, e.g., Reference 16), however, these methods only compress the signal without improving acquisition time. In order to compress and acquire volumes more quickly, modifications have to be made to the scanning method. Prior systems demonstrated this for an OCT endoscope by randomly changing the procedure-size during pull-back acquisition (see, e.g., Reference 40). However, this approach can be specific to pull-back endoscopes and cannot be applied to bench-top systems. A-line subsampling can be a better approach because it can be realized by simply over-driving the lateral scanning mechanism (e.g. galvo) to the desired undersampling rate. This modification can be applied to existing OCT systems with virtually no hardware changes. Furthermore, undersampling in such a manner can directly reduce scan time. For example, using the exemplary DN-PC with 25% a-line sampling and a full-resolution interval of 10 b-scans can reduce a one minute scan to 19.5 seconds. Thus, a reconstruction procedure specifically for a-line subsampling, rather than spectral subsampling, can be beneficial. Wide-spread use of a method to reduce scan time can have the potential to open new possibilities areas of OCT research such as whole organ (see, e.g., References 4, 41 and 42) and high-speed endoscopic imaging (see, e.g., References 43 and 44), and 4-D imaging. (See, e.g., References 6 and 45). With extension to time-lapse imaging, CS-OCT could impact additional application such as particle tracking (see, e.g., References 46 and 47), elastography (see, e.g., References 48-50), cilia and mucus movement (see, e.g., References 51 and 52), developmental biology (see, e.g., Reference 53), and Radio-Frequency Ablation ("RFA"). (See, e.g., References 54-56).

FIG. 22 shows an exemplary table illustrating quantitative summary of the effects of a-line sampling, staggering, and the full-resolution interval on compression and relative error according to an exemplary embodiment of the present disclosure. For example, eight use-cases were tested with staggering on and off, using two a-line sampling rates [0=50%. 25%], and using two full-resolution intervals 10 and 50. The OCT volume dimensions were 512×800×800 pixels, and a patch size of 32×32 pixels was used. The "Full-Res B-Scans" column shows the total number of full-resolution b-scans obtained for the two intervals. Similarly, the column labelled "Sampled A-Lines/B-Scan" shows 25% and 50% sampling results in acquisition of 200 and 400 a-lines per b-scan, respectively. The true compression rate includes the full-resolution b-scans so it is higher than the a-line sampling rate, though the margin of increase is larger for smaller sampling rates. In all cases, staggering improves the relative reconstruction error. Uniform sampling also performed better than random sampling.

FIGS. 23A and 23D show exemplary images generated using a prior OCT system. FIGS. 23B and 23E show exemplary images generated using the exemplary ultra-high speed OCT system according to an exemplary embodiment of the present disclosure. FIG. 23C shows an exemplary histopathological correlation for FIGS. 23A and 23D. FIG. 23F shows an exemplary histopathological correlation for FIGS. 23B and 23E according to an exemplary embodiment of the present disclosure.

Figure 24:
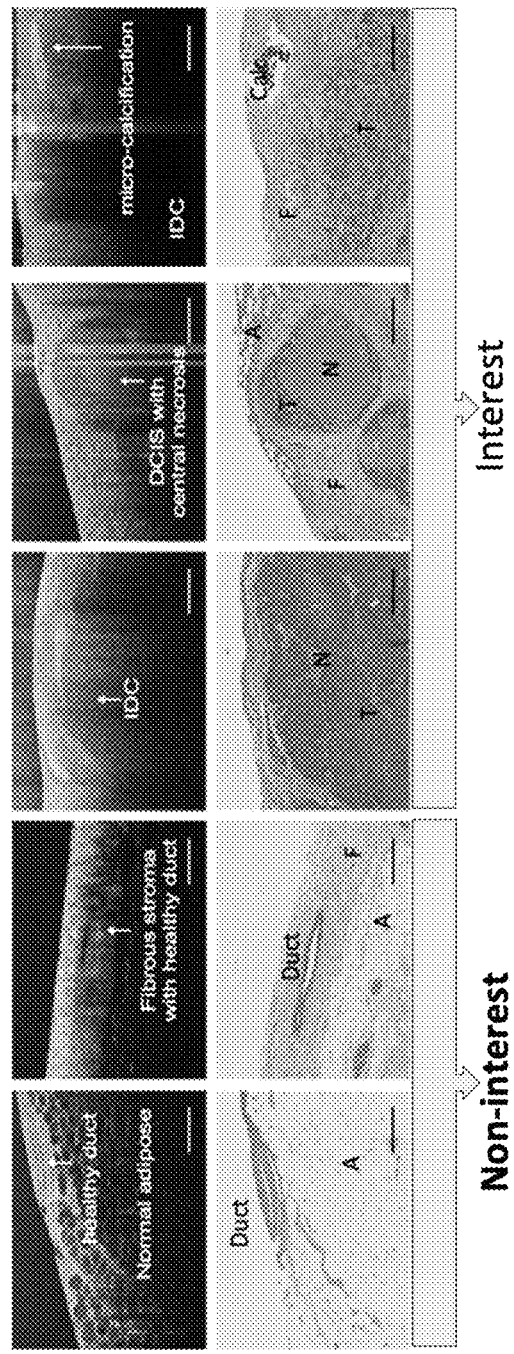
FIG. 24 is a set of Ultrahigh resolution OCT images of breast specimens including according to an exemplary embodiment of the present disclosure.
Figure 25:
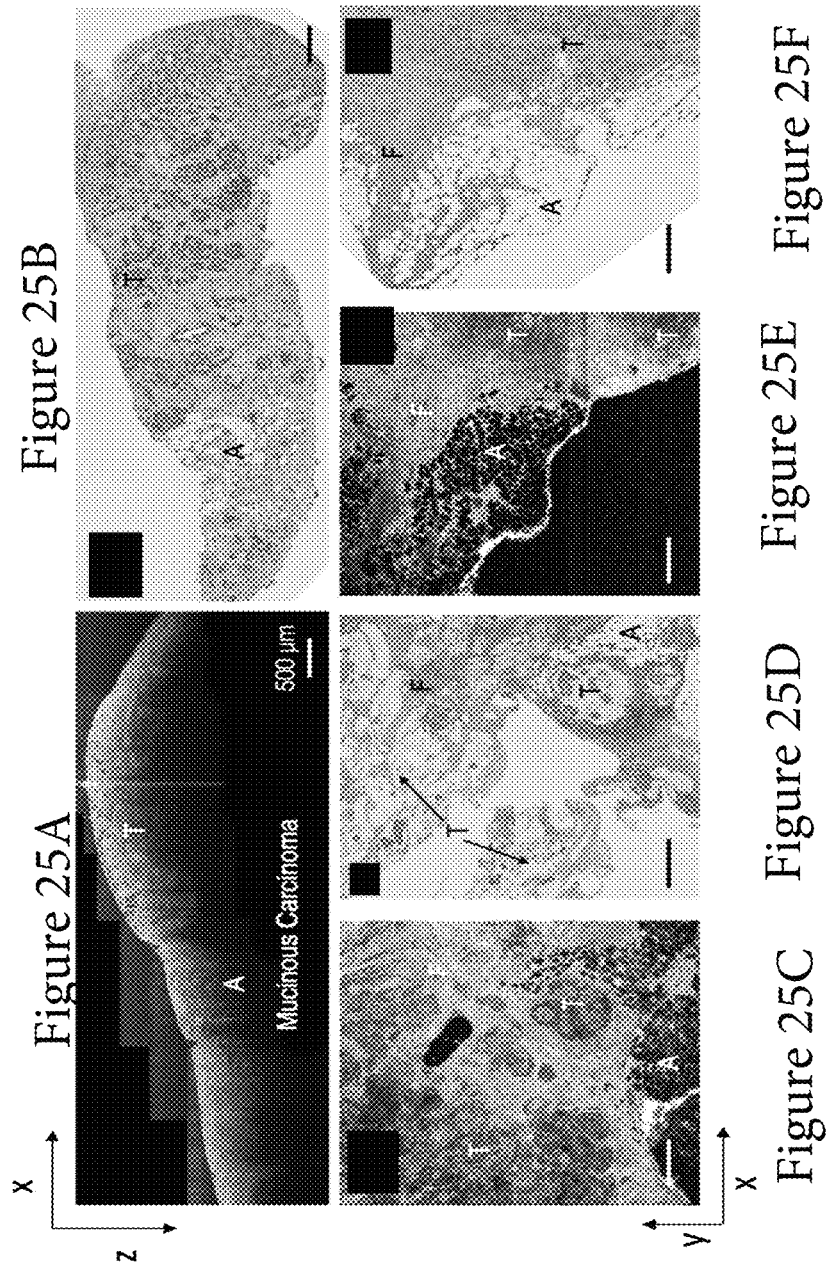
FIGS. 25A-25F is a set of exemplary stitched OCT volumes from ultrahigh resolution imaging according to an exemplary embodiment of the present disclosure.

FIG. 24 shows a set of ultra-high resolution OCT images of breast specimens including according to an exemplary embodiment of the present disclosure. FIGS. 25A-25F show exemplary stitched OCT volumes from ultra-high resolution imaging according to an exemplary embodiment of the present disclosure. In particular, FIG. 25A shows an exemplary stitched B-scan with a mucinous carcinoma and FIG. 25B shows the corresponding histology. FIGS. 25C and 25E show en face OCT images with the corresponding histology shown in FIGS. 25D and 25F. The scale bar is about 500 µm.

Figure 26:
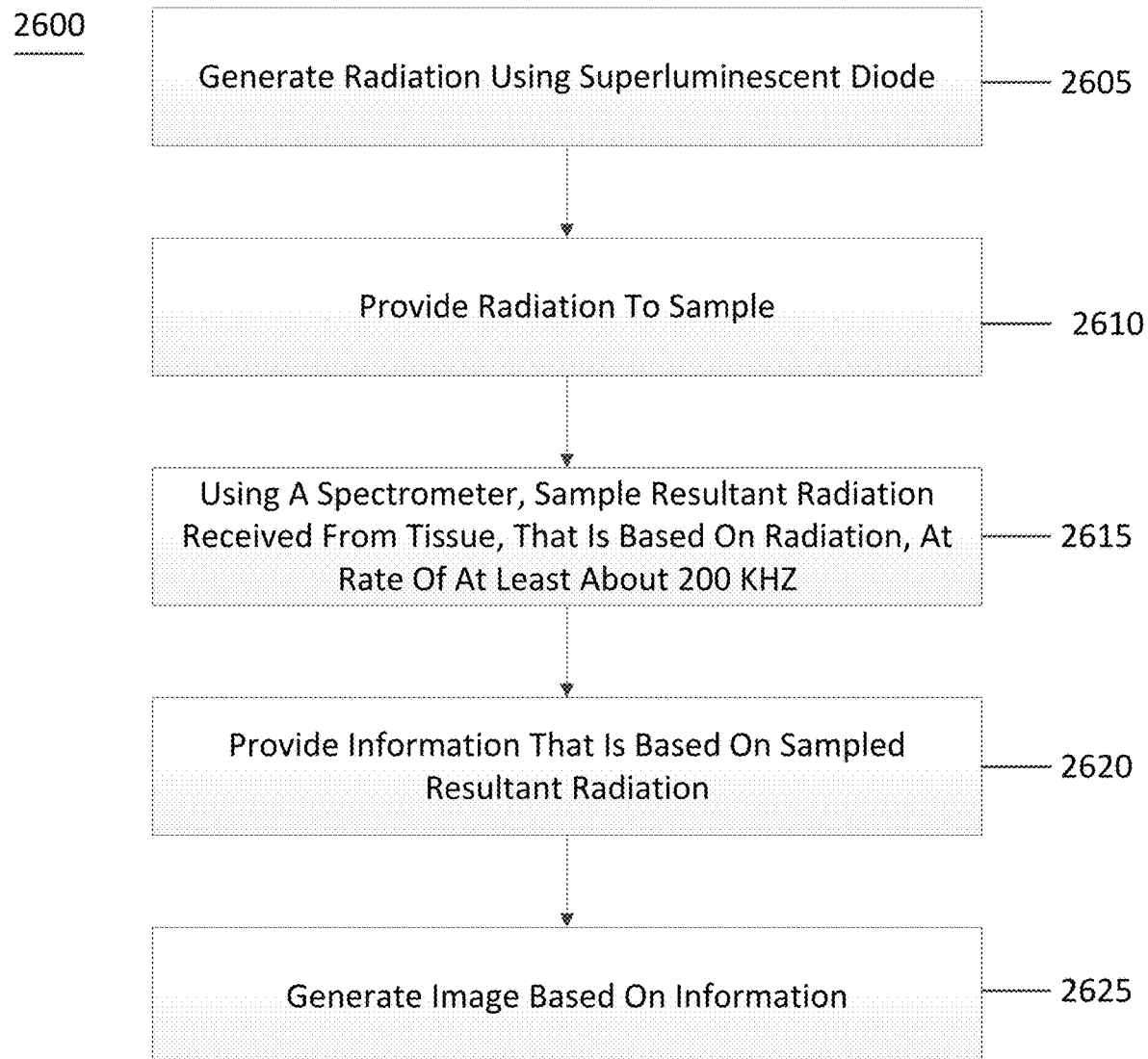
FIG. 26 is an exemplary flow diagram of a method for generating an image of a sample according to an exemplary embodiment of the present disclosure.

FIG. 26 shows an exemplary flow diagram of a method for generating an image of a sample according to an exemplary embodiment of the present disclosure. For example, at procedure 2605, a radiation can be generated using a superluminescent diode (SLD). At procedure 2610, the radiation can be provided to the sample. At procedure 2615, using a spectrometer, a resultant radiation received from the tissue, that is based on the radiation, at a rate of at least about 200 kHZ can be sampled. At procedure 2620, information that can be based on the sampled resultant radiation can be provided, and the image can be generated based on the information at procedure 2625.

Figure 27:
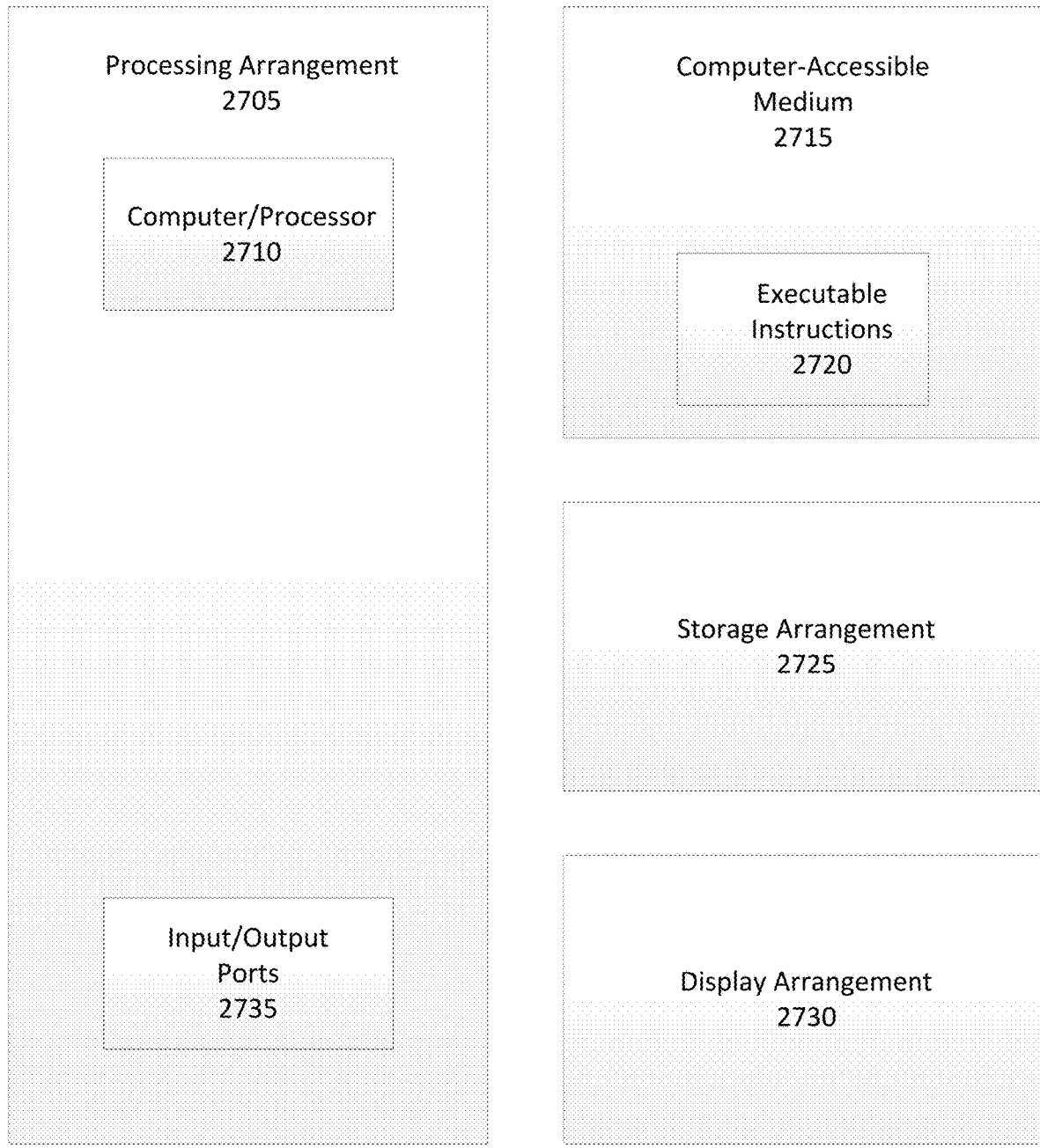
FIG. 27 is an exemplary block diagram of an exemplary system in accordance with certain exemplary embodiments of the present disclosure.

FIG. 27 shows a block diagram of an exemplary embodiment of a system according to the present disclosure, which can be utilized either in part or completely with any one or more of the exemplary embodiments of the present disclosure as provided in the enclosed Appendix. For example, exemplary procedures in accordance with the present disclosure described herein can be performed by a processing arrangement and/or a computing arrangement (e.g., computer hardware arrangement) 2705. Such processing/computing arrangement 2705 can be, for example entirely or a part of, or include, but not limited to, a computer/processor 2710 that can include, for example one or more microprocessors, and use instructions stored on a computer-accessible medium (e.g., RAM, ROM, hard drive, or other storage device).

As shown in FIG. 27, for example a computer-accessible medium 2715 (e.g., as described herein above, a storage device such as a hard disk, floppy disk, memory stick, CD-ROM, RAM, ROM, etc., or a collection thereof) can be provided (e.g., in communication with the processing arrangement 2705). The computer-accessible medium 2715 can contain executable instructions 2720 thereon. In addition or alternatively, a storage arrangement 2725 can be provided separately from the computer-accessible medium 2715, which can provide the instructions to the processing arrangement 2705 so as to configure the processing arrangement to execute certain exemplary procedures, processes, and methods, as described herein above, for example.

Further, the exemplary processing arrangement 2705 can be provided with or include an input/output ports 2735, which can include, for example a wired network, a wireless network, the internet, an intranet, a data collection probe, a sensor, etc. As shown in FIG. 27, the exemplary processing arrangement 2705 can be in communication with an exemplary display arrangement 2730, which, according to certain exemplary embodiments of the present disclosure, can be a touch-screen configured for inputting information to the processing arrangement in addition to outputting information from the processing arrangement, for example. Further, the exemplary display arrangement 2730 and/or a storage arrangement 2725 can be used to display and/or store data in a user-accessible format and/or user-readable format.

The foregoing merely illustrates the principles of the disclosure. Various modifications and alterations to the described embodiments will be apparent to those skilled in the art in view of the teachings herein. It will thus be appreciated that those skilled in the art will be able to devise numerous systems, arrangements, and procedures which, although not explicitly shown or described herein, embody the principles of the disclosure and can be thus within the spirit and scope of the disclosure. Various different exemplary embodiments can be used together with one another, as well as interchangeably therewith, as should be understood by those having ordinary skill in the art. In addition, certain terms used in the present disclosure, including the specification, drawings and claims thereof, can be used synonymously in certain instances, including, but not limited to, for example, data and information. It should be understood that, while these words, and/or other words that can be synonymous to one another, can be used synonymously herein, that there can be instances when such words can be intended to not be used synonymously. Further, to the extent that the prior art knowledge has not been explicitly incorporated by reference herein above, it is explicitly incorporated herein in its entirety. All publications referenced are incorporated herein by reference in their entireties.

EXEMPLARY REFERENCES

The following references are hereby incorporated by reference, in their entireties:

1. W. Wieser, W. Draxinger, T. Klein, S. Karpf, T. Pfeiffer, and R. Huber, "High definition live 3d-oct in vivo: design and evaluation of a 4d oct engine with 1 gvoxel/s," Biomed. Opt. Express 5, 2963-2977 (2014).
2. Y. Ling, X. Yao, U. A. Gamm, E. Arteaga-Solis, C. W. Emala, M. A. Choma, and C. P. Hendon, "Ex vivo visualization of human ciliated epithelium and quantitative analysis of induced flow dynamics by using optical coherence tomography," Lasers Surg. Med. 49, 270-279 (2017).
3. J. P. McLean, Y. Ling, and C. P. Hendon, "Frequency-constrained robust principal component analysis: a sparse representation approach to segmentation of dynamic features in optical coherence tomography imaging," Opt. Express 25, 25819-25830 (2017).
4. T. H. Lye, K. P. Vincent, A. D. McCulloch, and C. P. Hendon, "Tissue-Specific Optical Mapping Models of Swine Atria Informed by Optical Coherence Tomography," Biophys. J. 114, 1477-1489 (2018).
5. J. P. McLean, S. Fang, G. Gallos, K. M. Myers, and C. P. Hendon, "Three-dimensional collagen fiber mapping and tractography of human uterine tissue using OCT," Biomed. Opt. Express 11, 5518 (2020).
6. J. P. Kolb, W. Draxinger, J. Klee, T. Pfeiffer, M. Eibl, T. Klein, W. Wieser, and R. Huber, "Correction: Live video rate volumetric OCT imaging of the retina with multi-MHz A-scan rates," PLoS One 14, e0220829 (2019).
7. Y. Chen, Y.-J. Hong, S. Makita, and Y. Yasuno, "Three-dimensional eye motion correction by lissajous scan optical coherence tomography," Biomed. Opt. Express 8, 1783-1802 (2017).
8. D. L. Donoho and M. Elad, "Optimally sparse representation in general (nonorthogonal) dictionaries via 1 minimization," Proc. Natl. Acad. Sci. 100, 2197-2202 (2003).
9. H. Jung, K. Sung, K. S. Nayak, E. Y. Kim, and J. C. Ye, "K-t FOCUSS: A general compressed sensing framework for high resolution dynamic Mill," Magn. Reson. Medicine 61, 103-116 (2009).
10. R. Otazo, E. Candes, and D. K. Sodickson, "Low-rank plus sparse matrix decomposition for accelerated dynamic MRI with separation of background and dynamic components," Magn. Reson. Medicine 73, 1125-1136 (2015).
11. M. Lustig, D. Donoho, and J. M. Pauly, "Sparse MRI: The application of compressed sensing for rapid MR imaging," Magn. Reson. Medicine 58, 1182-1195 (2007).
12. X. Liu and J. U. Kang, "Compressive SD-OCT: the application of compressed sensing in spectral domain optical coherence tomography," Opt. Express 18, 22010 (2010).
13. D. Xu, N. Vaswani, Y. Huang, and J. U. Kang, "Modified compressive sensing optical coherence tomography with noise reduction," Opt. Lett. 37, 4209 (2012).
14. N. Zhang, T. Huo, C. Wang, T. Chen, J.-g. Zheng, and P. Xue, "Compressed sensing with linear-in-wavenumber sampling in spectral-domain optical coherence tomography," Opt. Lett. 37, 3075 (2012).
15. D. Xu, Y. Huang, and J. U. Kang, "Compressive sensing with dispersion compensation on non-linear wavenumber sampled spectral domain optical coherence tomography," Biomed. Opt. Express 4, 1519 (2013).
16. Y. Ling, W. Meiniel, R. Singh-Moon, E. Angelini, J.-C. Olivo-Marin, and C. P. Hendon, "Compressed sensing-enabled phase-sensitive swept-source optical coherence tomography," Opt. Express 27, 855 (2019).
17. E. Lebed, P. J. Mackenzie, M. V. Sarunic, and F. M. Beg, "Rapid Volumetric OCT Image Acquisition Using Compressive Sampling," Opt. Express 18, 21003 (2010).
18. D. Xu, Y. Huang, and J. U. Kang, "Real-time compressive sensing spectral domain optical coherence tomography," Opt. Lett. 39, 76 (2014).
19. D. Xu, Y. Huang, and J. U. Kang, "GPU-accelerated non-uniform fast Fourier transform-based compressive sensing spectral domain optical coherence tomography," Opt. Express 22, 14871 (2014).
20. D. Xu, Y. Huang, and J. U. Kang, "Volumetric (3D) compressive sensing spectral domain optical coherence tomography," Biomed. Opt. Express 5, 3921 (2014).
21. S. Schwartz, C. Liu, A. Wong, D. A. Clausi, P. Fieguth, and K. Bizheva, "Energy-guided learning approach to compressive FD-OCT," Opt. Express 21, 329 (2013).
22. L. Fang, S. Li, R. P. McNabb, Q. Nie, A. N. Kuo, C. A. Toth, J. A. Izatt, and S. Farsiu, "Fast acquisition and reconstruction of optical coherence tomography images via sparse representation," IEEE Transactions on Med. Imaging 32, 2034-2049 (2013).
23. S. Oshery, Z. Shiz, and W. Zhuy, "Low dimensional manifold model for image processing," SIAM J. on Imaging Sci. 10, 1669-1690 (2017).
24. E. J. Candes, X. Li, Y. Ma, and J. Wright, "Robust principal component analysis?" J. ACM 58, 1-37 (2011).
25. I. Daubechies, M. Defrise, and C. De Mol, "An iterative thresholding algorithm for linear inverse problems with a sparsity constraint," Commun. on Pure Appl. Math. 57, 1413-1457 (2004).
26. S. Boyd, "Distributed Optimization and Statistical Learning via the Alternating Direction Method of Multipliers," Foundations Trends Mach. Learn. 3, 1-122 (2010).
27. A. Majumdar, R. K. Ward, and T. Aboulnasr, "Compressed sensing based real-time dynamic MRI reconstruction," IEEE Transactions on Med. Imaging 31, 2253-2266 (2012).
28. Y.-W. Wen, M. K. Ng, and W.-K. Ching, "Iterative Algorithms Based on Decoupling of Deblurring and Denoising for Image Restoration," SIAM J. on Sci. Comput. 30, 2655-2674 (2008).
29. E. M. Eksioglu, "Decoupled Algorithm for MRI Reconstruction Using Nonlocal Block Matching Model: BM3D-MRI," J. Math. Imaging Vis. 56, 430-440 (2016).
30. J. Yang and Y. Zhang, "Alternating Direction Algorithms for $\ell^1$-Problems in Compressive Sensing," SIAM J. on Sci. Comput. 33, 250-278 (2011).
31. J. Yang, Y. Zhang, and W. Yin, "A fast alternating direction method for TVL1-L2 signal reconstruction from partial Fourier data," IEEE J. on Sel. Top. Signal Process. 4, 288-297 (2010).

32. Y. Gan, D. Tsay, S. B. Amir, C. C. Marboe, and C. P. Hendon, "Automated classification of optical coherence tomography images of human atrial tissue," J. Biomed. Opt. 21, 101407 (2016).
33. S. Farsiu, S. J. Chiu, R. V. O'Connell, F. A. Folgar, E. Yuan, J. A. Izatt, and C. A. Toth, "Quantitative classification of eyes with and without intermediate age-related macular degeneration using optical coherence tomography," Ophthalmology 121, 162-172 (2014).
34. J. P. McLean, Y. Gan, T. H. Lye, D. Qu, H. H. Lu, and C. P. Hendon, "High-speed collagen fiber modeling and orientation quantification for optical coherence tomography imaging," Opt. Express 27, 14457-14471 (2019).
35. D. Qu, P. J. Chuang, S. Prateepchinda, P. S. Balasubramanian, X. Yao, S. B. Doty, C. P. Hendon, and H. H. Lu, "Micro- and Ultrastructural Characterization of Age-Related Changes at the Anterior Cruciate Ligament-to-Bone Insertion," ACS Biomater. Sci. & Eng. 3, 2806-2814 (2017).
36. D. Mojahed, R. S. Ha, P. Chang, Y. Gan, X. Yao, B. Angelini, H. Hibshoosh, B. Taback, and C. P. Hendon, "Fully Automated Postlumpectomy Breast Margin Assessment Utilizing Convolutional Neural Network Based Optical Coherence Tomography Image Classification Method," Acad. Radiol. 27, e81-e86 (2020).
37. Z. Wang, A. C. Bovik, H. R. Sheikh, and E. P. Simoncelli, "Image quality assessment: From error visibility to structural similarity," IEEE Transactions on Image Process. 13, 600-612 (2004).
38. Z. Wang, E. Simoncelli, and A. Bovik, "Multiscale structural similarity for image quality assessment," in The Thirty-Seventh Asilomar Conference on Signals, Systems & Computers, 2003, vol. 2 (IEEE, 2016), pp. 1398-1402.
39. W. Liao, J. Hsieh, C. Wang, W. Zhang, S. Ai, Z. Peng, Z. Chen, B. He, X. Zhang, N. Zhang, B. Tang, and P. Xue, "Compressed sensing spectral domain optical coherence tomography with a hardware sparse-sampled camera," Opt. Lett. 44, 2955 (2019).
40. J. Wang, Y. Hu, and J. Wu, "Three-dimensional endoscopic OCT using sparse sampling with a miniature magnetic-driven scanning probe," Appl. Opt. 57, 10056 (2018).
41. Y. Gan, T. H. Lye, C. C. Marboe, and C. P. Hendon, "Characterization of the human myocardium by optical coherence tomography," J. Biophotonics pp. 1-10 (2019).
42. C. P. Hendon, T. H. Lye, X. Yao, Y. Gan, and C. C. Marboe, "Optical coherence tomography imaging of cardiac substrates," Quant. Imaging Medicine Surgery; Publ. Ahead Print 9, 882-904 (2019).
43. J. Mavadia-Shukla, P. Fathi, W. Liang, S. Wu, C. Sears, and X. Li, "High-speed, ultrahigh-resolution distal scanning oct endoscopy at 800 nm for in vivo imaging of colon tumorigenesis on murine models," Biomed. Opt. Express 9, 3731-3739 (2018).
44. W. Yuan, D. Chen, R. Sarabia-Estrada, H. Guerrero-Cazares, D. Li, A. Quiñones-Hinojosa, and X. Li, "Theranostic OCT microneedle for fast ultrahigh-resolution deep-brain imaging and efficient laser ablation in vivo," Sci. Adv. 6, 1-10 (2020).
45. L. M. Peterson, M. W. Jenkins, S. Gu, L. Barwick, M. Watanabe, and A. M. Rollins, "4D shear stress maps of the developing heart using Doppler optical coherence tomography," Biomed. Opt. Express 3, 3022 (2012).
46. K. K. Chu, D. Mojahed, C. M. Fernandez, Y. Li, L. Liu, E. J. Wilsterman, B. Diephuis, S. E. Birket, H. Bowers, G. Martin Solomon, B. S. Schuster, J. Hanes, S. M. Rowe, and G. J. Tearney, "Particle-Tracking Microrheology Using Micro-Optical Coherence Tomography," Biophys. J. 111, 1053-1063 (2016).
47. T. Tang, E. Deniz, M. K. Khokha, and H. D. Tagare, "Gaussian process post-processing for particle tracking velocimetry," Biomed. Opt. Express 10, 3196 (2019).
48. E. V. Gubarkova, A. A. Sovetsky, V. Y. Zaitsev, A. L. Matveyev, D. A. Vorontsov, M. A. Sirotkina, L. A. Matveev, A. A. Plekhanov, N. P. Pavlova, S. S. Kuznetsov, A. Y. Vorontsov, E. V. Zagaynova, and N. D. Gladkova, "Oct-elastography-based optical biopsy for breast cancer delineation and express assessment of morphological/molecular subtypes," Biomed. Opt. Express 10, 2244-2263 (2019).
49. B. F. Kennedy, X. Liang, S. G. Adie, D. K. Gerstmann, B. C. Quirk, S. A. Boppart, and D. D. Sampson, "In vivo three-dimensional optical coherence elastography," Opt. Express 19, 6623 (2011).
50. K. V. Larin and D. D. Sampson, "Optical coherence elastography-oct at work in tissue biomechanics [invited]," Biomed. Opt. Express 8, 1172-1202 (2017).
51. Y. He, Y. Qu, J. C. Jing, and Z. Chen, "Characterization of oviduct ciliary beat frequency using real time phase resolved doppler spectrally encoded interferometric microscopy," Biomed. Opt. Express 10, 5650-5659 (2019).
52. H. M. Leung, M. L. Wang, H. Osman, E. Abouei, C. MacAulay, M. Follen, J. A. Gardecki, and G. J. Tearney, "Imaging Intracellular Motion with Dynamic Micro-Optical Coherence Tomography," Biomed. Opt. Express 11, 2768-2778 (2020).
53. S. Bhat, I. V. Larina, K. V. Larin, M. E. Dickinson, and M. Liebling, "4D reconstruction of the beating embryonic heart from two orthogonal sets of parallel optical coherence tomography slice-sequences," IEEE Transactions on Med. Imaging 32, 578-588 (2013).
54. X. Zhao, X. Fu, C. Blumenthal, Y. T. Wang, M. W. Jenkins, C. Snyder, M. Arruda, and A. M. Rollins, "Integrated rfa/psoct catheter for real-time guidance of cardiac radio-frequency ablation," Biomed. Opt. Express 9, 6400-6411 (2018).
55. X. Yu, R. P. Singh-Moon, and C. P. Hendon, "Real-time assessment of catheter contact and orientation using an integrated optical coherence tomography cardiac ablation catheter," Appl. Opt. 58, 3823-3829 (2019).
56. C. P. Fleming, H. Wang, K. J. Quan, and A. M. Rollins, "Real-time monitoring of cardiac radio-frequency ablation lesion formation using an optical coherence tomography forward-imaging catheter," J. Biomed. Opt. 15, 1-3 (2010).

What is claimed is:

1. A system for generating at least one image of at least one sample, comprising:
   an interferometric imaging arrangement, comprising:
      a superluminescent diode (SLD) configured to generate at least one radiation to be provided to the at least one sample, and
      a spectrometer configured to (i) sample an A-line, (ii) receive a resultant radiation from the at least one sample, and (iii) generate information based on the resultant radiation; and
   a computer hardware arrangement configured to:
      generate the at least one image of the at least one sample based on the information received from the spectrometer,
      facilitate a plurality of b-scan acquisitions of the at least one sample, facilitate the b-scan acquisitions in order to generate the at least one image, and sample the b-scan acquisitions using an A-line staggering procedure and at least one full-resolution b-scan.

2. The system of claim 1, wherein the interferometric imaging arrangement is an optical coherence tomography imaging (OCT) arrangement.

3. The system of claim 1, wherein the computer hardware arrangement is further configured to:

extract a plurality of first features from a b-scan of the at least one sample, extract a plurality of second features from an en face scan of the at least one sample, and generate the at least one image by ensembling the first features and the second features.

4. The system of claim 1, wherein the spectrometer has an a-line sampling rate of at least about 250 kHZ.

5. The system of claim 1, wherein the SLD is a multiplexed SLD.

6. The system of claim 1, wherein the SLD has (i) a central wavelength of about 850 nm, and (ii) a bandwidth of about 100 nm 3 db.

7. The system of claim 1, wherein the spectrometer has (i) a bandwidth of about 180 nm, and (ii) a spectral resolution of less than about 0.09 nm.

8. The system of claim 1, wherein the imaging arrangement has at least one of (i) an axial resolution about 5.5 µm, or (ii) a lateral resolution of about 5.5 µm.

9. The system of claim 1, wherein the imaging arrangement provides a field of view of at least about 10 cm by 10 cm.

10. The system of claim 1, wherein the computer hardware arrangement is further configured to analyze the at least one image using a deep learning procedure.

11. The system of claim 10, wherein the computer arrangement is further configured to train the deep learning procedure using at least one of (i) a plurality of b-scans of a plurality of further samples, or (ii) a plurality of en face images of the plurality of further samples.

12. The system of claim 1, further comprising a motorized scanning stage configured to move in at least two dimensions, wherein the motorized scanning stage is configured to receive the at least one sample thereon.

13. The system of claim 1, wherein the computer hardware arrangement is configured to generate the at least one image using a compressed sensing procedure.

14. A method for generating at least one image of at least one sample, comprising:

generating at least one radiation using a superluminescent diode (SLD), and providing the radiation to the sample;

using a spectrometer, sampling a resultant radiation received from the at least one tissue, that is based on the at least one radiation;

providing information that is based on the sampled resultant radiation;

generating the at least one image based on the information;

facilitating a plurality of b-scan acquisitions of the at least one sample;

facilitating the b-scan acquisitions in order to generate the at least one image, and sampling the b-scan acquisitions using an A-line staggering procedure and at least one full-resolution b-scan.

15. The method of claim 14, wherein the sampling of the resultant radiation includes sampling the resultant radiation at a rate of at least about 250 kHZ.

16. The method of claim 14, wherein the SLD is a multiplexed SLD.

17. The method of claim 14, wherein the generating of the at least one image includes generating the at least one image using a compressed sensing procedure.

* * * * *